(12) United States Patent
Pyun

(10) Patent No.: US 10,833,330 B1
(45) Date of Patent: *Nov. 10, 2020

(54) SULFUR COMPOSITES AND POLYMERIC MATERIALS FROM ELEMENTAL SULFUR

(71) Applicant: ARIZONA BOARD OF REGENTS ON BEHALF OF THE UNIVERSITY OF ARIZONA, Tucson, AZ (US)

(72) Inventor: Dong-Chul Pyun, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 271 days.

This patent is subject to a terminal disclaimer.

(21) Appl. No.: 15/287,118

(22) Filed: Oct. 6, 2016

Related U.S. Application Data

(63) Continuation of application No. 14/622,429, filed on Feb. 13, 2015, now Pat. No. 9,567,439, which is a (Continued)

(51) Int. Cl.
  *H01M 4/38* (2006.01)
  *H01M 4/60* (2006.01)
  (Continued)

(52) U.S. Cl.
  CPC .......... *H01M 4/608* (2013.01); *C04B 35/6303* (2013.01); *C04B 35/64* (2013.01); (Continued)

(58) Field of Classification Search
  CPC .... H01M 10/052; H01M 4/382; H01M 4/606; H01M 10/4235; H01M 4/364; (Continued)

(56) References Cited

U.S. PATENT DOCUMENTS 2,779,761 A * 1/1957 Kibler .................. C07C 313/00
  544/85
3,251,797 A * 5/1966 De Pugh ................ C08L 27/06
  524/296

(Continued)

FOREIGN PATENT DOCUMENTS

CN 104713968 A 6/2015
EP 0806451 A1 11/1997
(Continued)

OTHER PUBLICATIONS

Swenson, M. Synthesis and Characterization of [Fe Fe] Hydrogenase Mimics. The University of Arizona, 2013, pp. 1-157 online), [retrieved on Jan. 19, 2018]. Retrieved from the Internet <http://arizona.openrepository.com/arizona/handle/1 0150/294029>.

(Continued)

*Primary Examiner* — Michael A Salvitti
(74) *Attorney, Agent, or Firm* — Nguyen Tarbet

(57) ABSTRACT

Sulfur composites and polymeric materials having a high sulfur content and prepared from elemental sulfur as the primary chemical feedstock. The sulfur copolymers are prepared by the polymerization of elemental sulfur with one or more monomers of amines, thiols, sulfides, alkynylly unsaturated monomers, nitrones, aldehydes, ketones, thiiranes, ethylenically unsaturated monomers, or epoxides. The sulfur copolymers may be further dispersed with metal or ceramic composites or copolymerized with elemental carbon, photoactive organic chromophores, or reactive and solubilising/biocompatible moieties. The sulfur composites and polymeric materials feature the ability self-healing through thermal reformation. Applications utilizing the sulfur composites and polymeric materials may include electrochemical cells, optics, H$_2$S donors and antimicrobial materials.

11 Claims, 31 Drawing Sheets
(29 of 31 Drawing Sheet(s) Filed in Color)

Related U.S. Application Data continuation-in-part of application No. 14/237,659, filed as application No. PCT/US2012/050602 on Aug. 13, 2012, now Pat. No. 9,306,218.

(60) Provisional application No. 62/039,561, filed on Aug. 20, 2014, provisional application No. 62/039,588, filed on Aug. 20, 2014, provisional application No. 62/017,750, filed on Jun. 26, 2014, provisional application No. 61/940,102, filed on Feb. 14, 2014, provisional application No. 61/685,847, filed on Mar. 26, 2012, provisional application No. 61/574,957, filed on Aug. 12, 2011, provisional application No. 61/574,903, filed on Aug. 11, 2011.

(51) Int. Cl.

| | | |
|---|---|---|
| *C04B 35/63* | (2006.01) | |
| *C04B 35/64* | (2006.01) | |
| *C08G 75/16* | (2006.01) | |
| *H01M 4/66* | (2006.01) | |
| *H01M 4/04* | (2006.01) | |
| *H01M 4/58* | (2010.01) | |

(52) U.S. Cl.
CPC .......... *C08G 75/16* (2013.01); *H01M 4/0404* (2013.01); *H01M 4/5815* (2013.01); *H01M 4/664* (2013.01); *C04B 2235/9653* (2013.01)

(58) Field of Classification Search
CPC ........ H01M 4/38; H01M 4/5815; H01M 4/62; H01M 4/628; C08J 2381/04
See application file for complete search history.

(56) References Cited

U.S. PATENT DOCUMENTS

| | | | |
|---|---|---|---|
| 3,290,266 A | 12/1966 | Barnes et al. | |
| 3,542,701 A | 11/1970 | van Raamsdonk | |
| 3,767,613 A | 10/1973 | Dix et al. | |
| 3,892,686 A | 7/1975 | Woo | |
| 4,000,347 A * | 12/1976 | Ranney .................. | C03C 17/30 156/329 |
| 4,094,751 A | 6/1978 | Nozik | |
| 4,238,585 A * | 12/1980 | Bertozzi ............ | C08G 18/6453 525/535 |
| 4,346,191 A * | 8/1982 | Blount ............... | C08G 59/4085 524/710 |
| 4,382,846 A | 5/1983 | Gratzel et al. | |
| 4,568,435 A | 2/1986 | Shelnutt | |
| 4,606,798 A | 8/1986 | Sasse et al. | |
| 4,671,896 A | 6/1987 | Hasegawa et al. | |
| 4,749,347 A | 6/1988 | Valavaara | |
| 4,833,048 A | 5/1989 | DeJonghe et al. | |
| 5,115,060 A | 5/1992 | Grey | |
| 5,121,329 A | 6/1992 | Crump | |
| 5,279,910 A | 1/1994 | Sasaki et al. | |
| 5,371,176 A | 6/1994 | Bezwada et al. | |
| 5,362,493 A | 11/1994 | Skotheim et al. | |
| 5,811,470 A | 9/1998 | Prindle et al. | |
| 5,929,202 A | 7/1999 | Arita et al. | |
| 6,011,094 A | 1/2000 | Planche et al. | |
| 6,072,026 A * | 6/2000 | Kawase ............... | C08G 61/122 429/122 |
| 6,111,030 A * | 8/2000 | Hartman ............... | C08G 59/54 525/420 |
| 9,306,218 B2 * | 4/2016 | Pyun ..................... | H01M 4/382 |
| 9,463,597 B2 | 10/2016 | Van De Vrie et al. | |
| 9,567,439 B1 * | 2/2017 | Pyun ....................... | C01B 17/96 |
| 2001/0047043 A1 * | 11/2001 | Okoroafor ............ | C08G 75/08 522/31 |
| 2001/0047403 A1 | 11/2001 | Okoroafor et al. | |
| 2002/0039680 A1 * | 4/2002 | Hwang ................. | H01M 4/136 429/218.1 |
| 2007/0010600 A1 | 1/2007 | Goodman et al. | |
| 2007/0253772 A1 | 11/2007 | Kubo et al. | |
| 2008/0038645 A1 * | 2/2008 | Kolosnitsyn ............ | H01M 4/40 429/338 |
| 2010/0029163 A1 | 2/2010 | Ogle et al. | |
| 2011/0245360 A1 | 10/2011 | Hahn et al. | |
| 2011/0263755 A1 | 10/2011 | Mohamed et al. | |
| 2012/0264837 A1 | 10/2012 | Eberstaller et al. | |
| 2013/0040197 A1 * | 2/2013 | Liu ......................... | C08F 34/00 429/213 |
| 2013/0064904 A1 | 3/2013 | Gojon-Romanillos et al. | |
| 2014/0110881 A1 * | 4/2014 | Keledjian ............... | B32B 15/08 264/241 |
| 2014/0199592 A1 * | 7/2014 | Pyun ..................... | H01M 4/382 429/213 |
| 2015/0203638 A1 | 7/2015 | Sivanandan et al. | |
| 2018/0079865 A1 * | 3/2018 | Pyun ..................... | H01M 4/606 |
| 2018/0105649 A1 * | 4/2018 | Pyun ..................... | H01M 4/606 |

FOREIGN PATENT DOCUMENTS

| | | |
|---|---|---|
| EP | 1882713 | 1/2008 |
| EP | 2093605 | 8/2009 |
| EP | 2896644 A1 | 7/2015 |
| GB | 1203577 A | 8/1970 |
| GB | 1516554 A | 7/1978 |
| WO | WO1995018652 A1 | 7/1995 |
| WO | WO2007076067 A3 | 7/2007 |
| WO | WO2009158385 A2 | 12/2009 |
| WO | WO2013/023216 A1 | 2/2013 |
| WO | WO2013155038 A1 | 10/2013 |
| WO | WO2014052255 A1 | 4/2014 |
| WO | WO2014179100 A1 | 11/2014 |
| WO | WO2015/123552 A1 | 8/2015 |

OTHER PUBLICATIONS

Chung, W.J. et al., "Elemental Sulfur as a Reactive Medium for Gold Nanoparticles and Nanocomposite Materials", Angewandte Chemie International Edition, 2011, 50, 11409-11412.

Colquhoun, Howard M., "Materials that heal themselves", Nature Chemistry, Jun. 2012, vol. 4, 435-436.

Yang, Ying and Urban Marek W., "Self-healing polymeric materials", Chem. Soc. Rev., 2013, 42, 7446-7467.

Hasegawa, Urara and Van Der Vlies, André J., "Design and Synthesis of Polymeric Hydrogen Sulfide Donors", Bioconjugate Chemistry, 2014, 25 (7), 1290-1300.

Foster, Jeffrey C., et al., "S-Aroylthiooximes: A Facile Route to Hydrogen Sulfide Releasing Compounds with Structure-Dependent Release Kinetics", Organic Letters. 2014, 16, 1558-1561.

Wurthner, F., "Perylene bisimide dyes as versatile building blocks for functional supramolecular architectures", Chem. Commun. 2004, 1564-1579.

Chung, W.-. et al., "The use of elemental sulfur as an alternative feedstock for polymeric materials", Nature Chemistry 2013, vol. 5, 518-524.

Simmonds, A.G. et al., "Inverse Vulcanization of Elemental Sulfur to Prepare Polymeric Electrode Materials for Li—S Batteries", ACS Macro Lett. 2014, 3, 229-232.

Liu, G. et al., "α-Sulfur Crystals as a Visible-Light-Active Photocatalyst", J. Am. Chem. Soc. 2012, 134, 9070-9073.

Asmus, K.-D., "Pulse Radiolysis Methodology", Methods in Enzymology 1984, 105, 167-178.

Nishide, et al., "Toward Flexible Batteries", (2008) Science, vol. 319, 737-738.

Nishide, et al., "Emerging N-Type Redox-Active Radical Polymer for a Totally Organic Polymer-Based Rechargeable Battery", (2009), Adv Mater, 21, 1627-1630.

Tarascon, et al., "Key challenges in future Li-battery research", (2010) Phil Trans R Soc A, 368, 3227.

Rotinjanz, et al. (1908) Z. Physik Chem, 62, 609.

Bacon, et al., "The Viscosity of Sulfur", (1943) J Am Chem Soc, 65, 639.

(56) References Cited

OTHER PUBLICATIONS

Eyring, et al., "The Properties of Liquid Sulfur", (1943) J Am Chem 65, 648.
Tobolsky, A. V. et al., "Equilibrium Polymerization of Sulfur", Am. Chem. Soc.1959, 81, 780.
Penczek, et al. (1974) Nature, 273, 738.
Nazar, et al., "A highly ordered nanostructured carbon-sulphur cathode for lithium-sulphur batteries", Nature Mater. 2009, 8, 500-506.
Scrosati, et al., "A High-Performance Polymer Tin Sulfur Lithium Ion Battery", Angew. Chem. In!. Ed. 2010, 49, 2371-2374.
Then, et al., J. Phys. Chem. C 2011, 115, 6057-6063.
Yang, et al., ACS Nano 2011, 5, 9187-9193.
Bartlett, et al., (1956) J Am Chern Soc, 78, 3710.
McGrath, et al. (2006) Polymer, 47, 4042.
Ueda, et al., (2009) J Mater Chem, 19, 8907.
Trofimov, et al. (2002) "Sulfur-rich copolymers of sulfur with 5-vinylbicyclo hept-2-ene and tricyclo deca-3,8-diene as prospective cathode materials for lithium cells," Sufur Letters, 25: 219-227.
Ning, et al., (2004) "Novel cathode material based on chloropolystyrene," PMSE Preprints, American Chemical Society 90: 396-397.
Nang, et al., Nano Lett. 2011, 11, 2644-2647.
Meng, et al., Nano Lett. 2011, 11, 4462-4467.
Li, et al., Proc. Nail. Acad. Sci. U.S.A. 2013, 110, 7148-7153.
Zheng, et al., Nano Lett. 2013, 13, 1265-1270.
Zhou, et al., ACS Nano 2013, 7, 8801-8808.
Seh, et al., Nat. Commun. 2013, 4.
Li, et al., Nano Lett. 2013, 13, 5534.
Liu, et al., Nat. Nanolech. 2014, 9, 187.
Pyun, J. Angew. Chem Int. Ed., 2011, 50, 11409-11412.
Scrosati, et al. Angew. Chem. Int Ed., 2010, 49, 2371-2374.
Chung, et al., Nature Chemistry. Jun. 2013. vol. 5, pp. 518-524. Published online Apr. 14, 2013.
Suzuki et al. Hydrogen generation using water-insoluble polymer-bound ruthenium(ii) Complexes. Chemical Communications, 1997, Issue 2, p. 227.
Suzuki et al. Photoinduced hydrogen generation from water-insoluble polymer photosensitizer films. Polymer, 1998, vol. 39, Issue 8, p. 1539-1543.
Suzuki et al. Photoinduced hydrogen generation using polymer photosensitizers. Macromolecular Chemistry and Physics, Jun. 1998, vol. 199, Issue 6.
Wang et al. A metal-free polymeric photocatalyst for hydrogen production from water under visible light. Nature Materials 8, 76-80 (2009).
Goldsmith et al. Discovery and High-Throughput Screening of Heteroleptic Iridium Complexes for Photoinduced Hydrogen Production. J. Am. Chem. Soc., 2005, 127 (20), pp. 7502-7510.
Tinker et al. Visible Light Induced Catalytic Water Reduction without an Electron Relay. Chemistry—A European Journal, 2007, vol. 13, Issue 31, pp. 8726-8732.
Happ et al. Towards Hydrogen Evolution Initiated by LED Light: 2-(1 H-1,2,3-Triazol-4-yl)pyridine containing Polymers as Photocatalyst. Macromolecular Rapid Communications, Apr. 2015, vol. 36, Issue 7, 671-677.
Aguirre De Carcer et al. Active-Site Models for Iron Hydrogenases: Reduction Chemistry of Dinuclear Iron Complexes. Inorg. Chem., 2006, 45 (20), pp. 8000-8002.
Alongia et al. Caseins and hydrophobins as novel green flame retardants for cotton fabrics. Polymer Degradation and Stability vol. 99, Jan. 2014, pp. 111-117.
Beom-Young Ryu and Todd Emrick. Thermally Induced Structural Transformation of Bisphenol-1,2,3-triazole Polymers: Smart, Self-Extinguishing Materials. Angew. Chem. Int. Ed. 2010, 49, 9644-9647.
Laufer et al. Clay-Chitosan Nanobrick Walls: Completely Renewable Gas Barrier and Flame-Retardant Nanocoatings. ACS Appl. Mater. Interfaces 2012, 4, 1643-1649.
Laufer et al. Exceptionally Flame Retardant Sulfur-Based Multilayer Nanocoating for Polyurethane Prepared from Aqueous Polyelectrolyte Solutions. ACS Macro Lett., 2013, 2 (5), pp. 361-365.
Li et al. Intumescent All-Polymer Multilayer Nanocoating Capable of Extinguishing Flame on Fabric. Adv. Mater. 2011, 23, 3926-3931.
Ding et al. Photoelectrocatalytic Water Splitting: Significance of Cocatalysts, Electrolyte, and Interfaces, ACS Catal. 2017, 7, 675-688.

* cited by examiner

Controlled # of S-S bonds and C-H bonds

Amorphous, high refractive index copolymer

SULFUR COMPOSITES AND POLYMERIC MATERIALS FROM ELEMENTAL SULFUR

CROSS REFERENCE

This application is a continuation of and claims priority to U.S. patent application Ser. No. 14/622,429, filed Feb. 13, 2015, which claims priority to U.S. Provisional Patent Application No. 62/039,588, filed Aug. 20, 2014, U.S. Provisional Patent Application No. 62/039,561, filed Aug. 20, 2014, U.S. Provisional Patent Application No. 62/017,750, filed Jun. 26, 2014, and U.S. Provisional Patent Application No. 61/940,102, filed Feb. 14, 2014, the specification(s) of which is/are incorporated herein in their entirety by reference.

Further, U.S. patent application Ser. No. 14/622,429 is a continuation-in-part of and claims priority to U.S. patent application Ser. No. 14/237,659, filed Mar. 11, 2014, now U.S. Pat. No. 9,306,218, which is a 371 of International Application No. PCT/US12/50602 filed on Aug. 13, 2012, which claims priority to U.S. Provisional Patent Application No. 61/685,847, filed Mar. 26, 2012, U.S. Provisional Patent Application No. 61/574,957, filed Aug. 12, 2011, and U.S. Provisional Patent Application No. 61/574,903, filed Aug. 11, 2011, the specification(s) of which is/are incorporated herein in their entirety by reference.

GOVERNMENT SUPPORT

This invention was made with government support under Grant No. CHE1305773 awarded by NSF. The government has certain rights in the invention.

FIELD OF THE INVENTION

The present invention relates to sulfur composites and polymeric materials having a high sulfur content, in particular, sulfur copolymers that are polymerized with epoxides or dispersed with metal or ceramic composites; electrochemical cells utilizing the sulfur composites and polymeric materials; photoactive sulfur copolymers; sulfur polymer nanoparticles as hydrogen sulfide (H2S) donors; and methods of repairing sulfur polymeric materials by self-healing.

BACKGROUND OF THE INVENTION

An incredible abundance of elemental sulfur, nearly 7-million tons is generated as a waste byproduct from hydrodesulfurization of crude petroleum feedstocks, which converts alkanethiols and other (organo) sulfur compounds into $S_8$ as described in Chung and which is hereby incorporated herein by reference in its entirety. Before the invention of the inverse vulcanization process, there were only a limited number of synthetic methods available to utilize and modify elemental sulfur. Current industrial utilization of elemental sulfur is centered around sulfuric acid, agrochemicals, and vulcanization of rubber. For example, elemental sulfur is used primarily for sulfuric acid and ammonium phosphate fertilizers, where the rest of the excess sulfur is stored as megaton-sized, above ground sulfur towers.

While sulfur feedstocks are plentiful, sulfur is difficult to process. In its original form, elemental sulfur consists of a cyclic molecule having the chemical formulation $S_8$. Elemental sulfur is a brittle, intractable, crystalline solid having poor solid state mechanical properties, poor solution processing characteristics, and there is a limited slate of synthetic methodologies developed for it. Hence, there is a need for the production of new materials that offers significant environmental and public health benefits to mitigate the storage of excess sulfur in powder, or brick form.

Elemental sulfur has been explored for use in lithium-sulfur electrochemical cells. Sulfur can oxidize lithium when configured appropriately in an electrochemical cell, and is known to be a very high energy-density cathode material. The poor electrical and electrochemical properties of pure elemental sulfur, such as low cycle stability and poor conductivity) have limited the development of this technology. For example, one key limitation of lithium-sulfur technology is the ability to retain high charge capacity for extended numbers of charge-discharge cycles ("cycle lifetimes"). Cells based on present lithium ion technology has low capacity (180 mAh/g) but can be cycled for 500-1000 cycles. Lithium-sulfur cells based on elemental sulfur have very high initial charge capacity (in excess of 1200 mAh/g, but their capacity drops to below 400 mAh/g within the first 100-500 cycles. Hence, the creation of novel copolymer materials from elemental sulfur feedstocks would be tremendously beneficial in improving sustainability and energy practices. In particular, improved battery technology and materials that can extend cycle lifetimes while retaining reasonable charge capacity will significantly impact the energy and transportation sectors and further mitigate US dependence on fossil fuels.

There have been several recent attempts to form sulfur into nanomaterials for use as cathodes in lithium-sulfur electrochemical cells, such as impregnation into mesoporous carbon materials, encapsulation with graphenes, encapsulation into carbon spheres, and encapsulation into conjugated polymer spheres. While these examples demonstrate that the encapsulation of elemental sulfur with a conductive colloidal shell in a core/shell colloid can enhance electrochemical stability, these synthetic methods are challenging to implement to larger scale production required for industrial application. Hence, a new family of inexpensive, functional materials obtained by practical methods is desirable.

Polymeric materials and structures commonly experience physical damage or structure failure due to factors affecting their physical properties, such as environmental exposure or mechanical or thermal stress. According to Colquhoun, which is hereby incorporated herein by reference in its entirety, there is a growing interest in developing new polymers that have the ability to repair themselves in order to enhance and prolong the life of these polymers. However, these new polymers require external energy or agents for repair. Hence, there is a desire to develop polymeric materials capable of self-healing that also require little to no external intervention.

Elemental sulfur is inherently insulating and poorly photoactive. One key challenge is to understand the synthetic chemistry necessary for modification of sulfur to prepare photoactive materials, especially materials that act as photo-semiconductors. However, by utilizing the inverse vulcanization process to enable the synthesis of modified sulfur polymers, the waste sulfur can be transformed from an insulator into a photoelectrochemically active material.

Aside from using sulfur to form nanomaterials for use in a variety of applications, such as cathodes in lithium-sulfur electrochemical cells, optics and weapon production, another particular field of interest is the use of sulfur polymer nanoparticles as hydrogen sulfide ($H_2S$) donors. According to Hasegawa, which is hereby incorporated herein by reference in its entirety, $H_2S$ has been recognized as a third gaseous transmitter produced endogenously from cysteine and other enzymes for signaling purposes. Nitric oxide (NO) and carbon monoxide (CO) are also examples of signaling gases. Although considered a toxic compound, $H_2S$ gas has beneficial effects on human organs and biological processes at low concentrations. Examples of these benefits include cardioprotection, inflammation regulation, cell protection during ischemia reperfusion and neuro-inflammation, and vasodilation, as described in Foster and which is hereby incorporated herein by reference in its entirety. Furthermore, unlike NO and CO, $H_2S$ gas does not emit reactive oxygen species that could affect certain cell functions. Limited studies have been performed on $H_2S$ as a signaling gas and identifying potential $H_2S$ donors. Previous studies utilized salts such as $NaHS/Na_2S$, which have demonstrated uncontrolled release profiles (Hasegawa). Hence, there is a need to develop $H_2S$ donors capable of slowly and continuously releasing $H_2S$ gas.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention features a sulfur polymer composition comprising sulfur monomers polymerized with one or more amine monomers, thiol monomers, sulfide monomers, alkynylly unsaturated monomers, nitrone monomers, aldehyde monomers, ketone monomers, thiirane monomers, and ethylenically unsaturated monomers. The sulfur polymer composition may be further polymerized with one or more epoxide monomers, wherein the epoxide monomers may be varying epoxide compounds, resulting in novel thermosetting and thermoplastic polymers. The present invention also features a novel composite material produced from elemental sulfur and a metal or ceramic composite. Liquid sulfur is utilized to prepare the sulfur composite materials that are based on metal carbides, metal sulfides and other chalcogenides, along with metal nitrides to form enhanced electroactive cathode materials. This sulfur composite material may be further copolymerized with the sulfur polymer composition or with the modified sulfur polymer composition polymerized with the epoxide monomers(s). The present invention further features an improved electrochemical cell utilizing any of the above sulfur containing materials as a cathode for the electrochemical cell.

These novel sulfur containing polymeric compositions and composite materials have the ability to self-heal. Without wishing to limit the present invention to any particular theory or mechanism, it is believed that the self-healing property of these materials are due to their reversible S—S bonds, which allows for broken S—S bonds to be reconnected by methods such as heat processing. A substrate constructed from these materials may be reworkable or repairable.

The present invention also features the use of sulfur to make a new class of photoactive sulfur polymers. The polymers can be used as a new solar fuel in which photochemical processes generate useful chemicals for clean energy and commodity chemicals.

The present invention features hydrogen sulfide donating sulfur containing polymers and methods of preparing said polymers. The present invention also features methods of treating biological conditions and inhibiting microbial growth using $H_2S$ gas. In some embodiments, the present invention utilizes sulfur containing polymers prepared via a variety of synthetic processes, such as inverse vulcanization and other existing synthetic chemical methods to prepare molecules, polymers, nanomaterials, and nanocomposites that can deliver $H_2S$ under biological conditions.

BRIEF DESCRIPTION OF THE DRAWINGS

This patent application contains at least one drawing executed in color. Copies of this patent or patent application publication with color drawing(s) will be provided by the Office upon request and payment of the necessary fee.

FIG. 32b also shows a lead sulfide (PbS) product.

DESCRIPTION OF PREFERRED EMBODIMENTS

Figure 1:
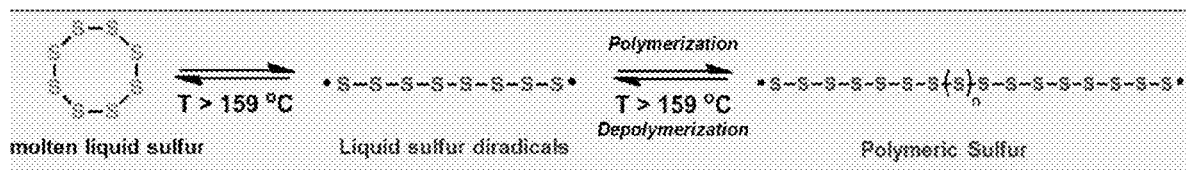
FIG. 1 shows a reaction schematic of a sulfur ring (Se) opening and polymerizing.
Figure 2:
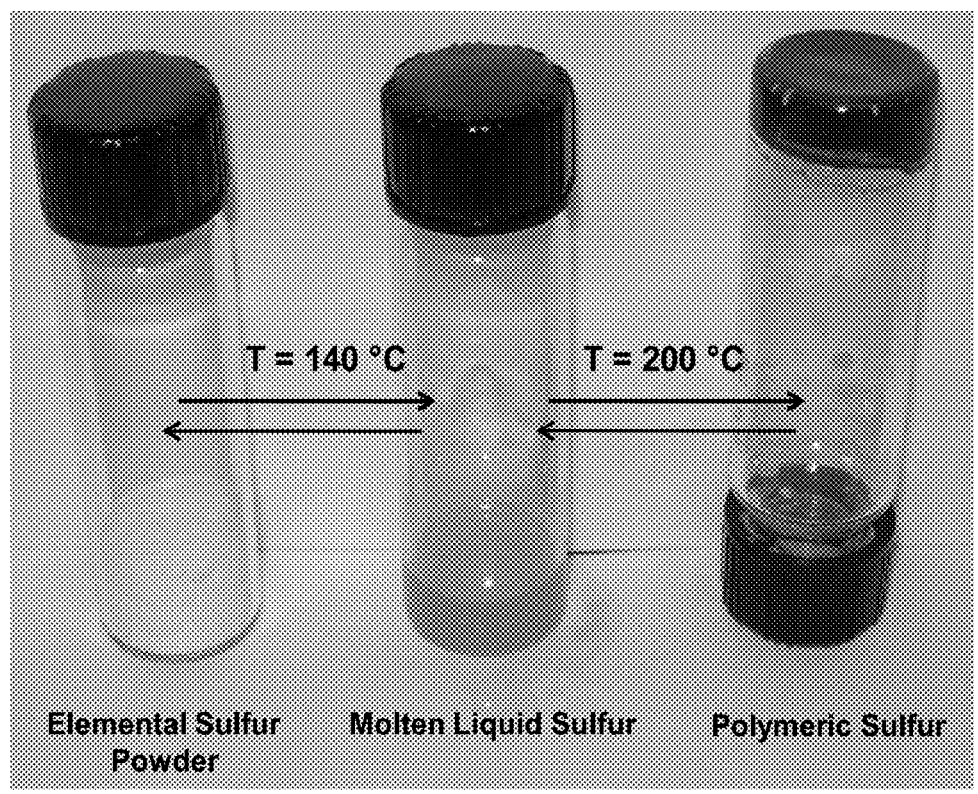
FIG. 2 shows lab samples of an elemental sulfur powder, a molten liquid sulfur, and a polymerized sulfur.
Figure 3:
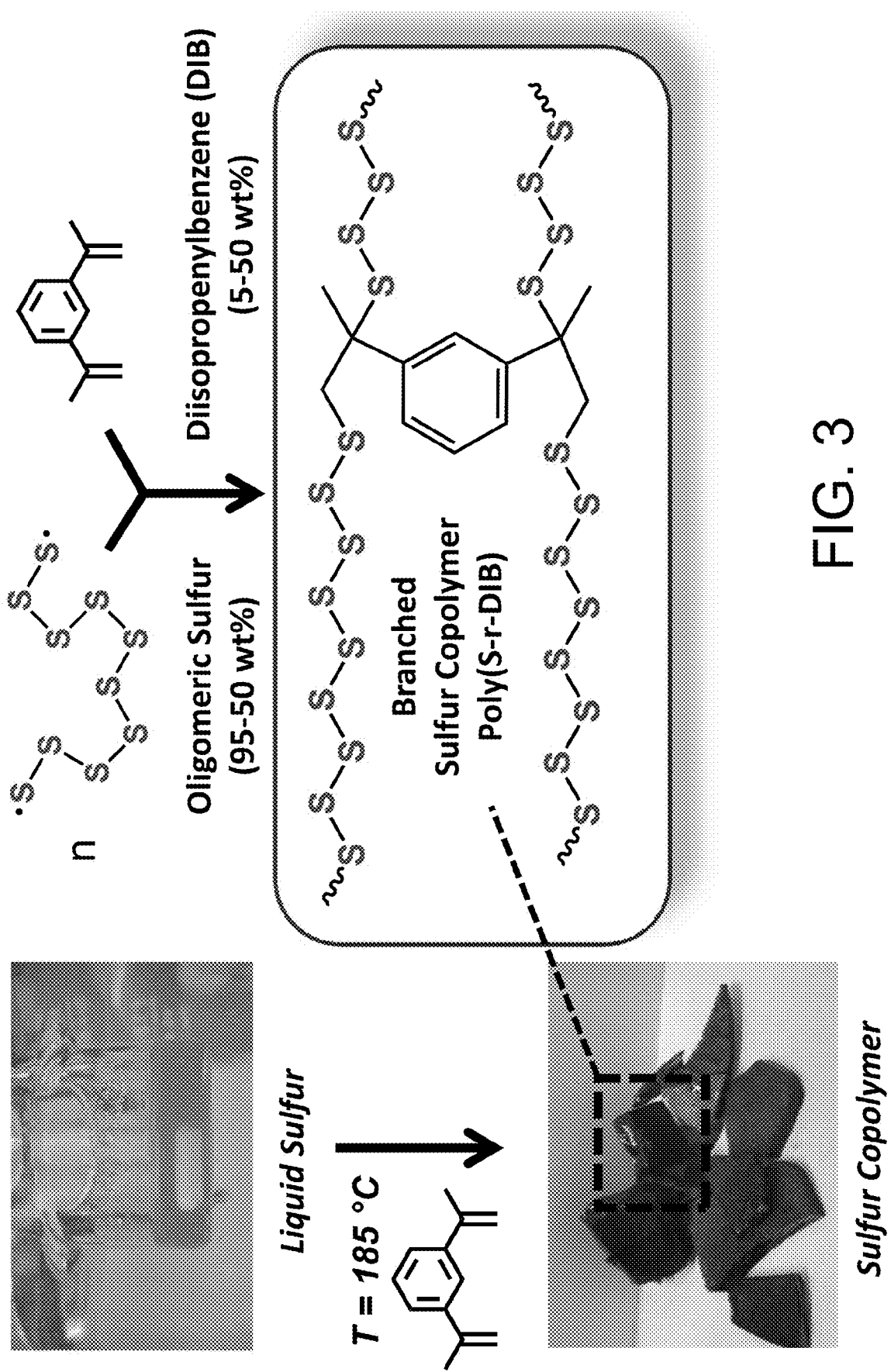
FIG. 3 shows a reaction schematic of a sulfur copolymer and a lab sample of a sulfur copolymer.
Figure 4:
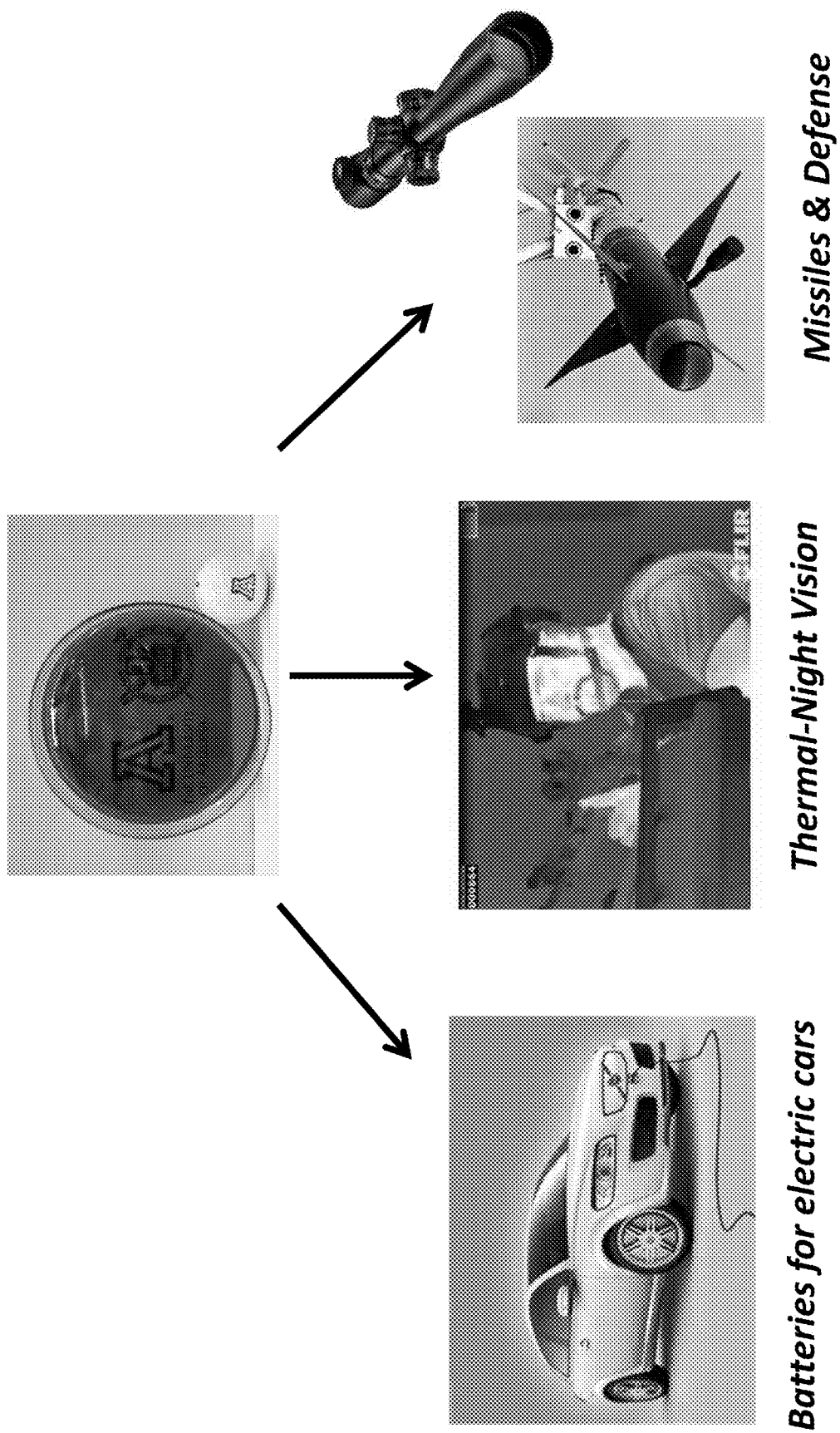
FIG. 4 shows non-limiting exemplary applications utilizing the sulfur copolymer.

As used herein, the term "amine monomer" is a monomer that is polymerizable through its amine groups. In one embodiment, aromatic amines and multi-functional amines may be used. Amine monomers include, but are not limited to, m-phenylenediamine, and p-phenylenediamine. The various types of phenylenediamines are inexpensive reagents due to their wide-spread use in the preparation of many conventional polymers, e.g., polyurethanes, polyamides. In the reaction of 1,3-phenylenediamine with $S_8$ a surprising substitution of the aromatic ring with sulfur groups in the copolymerization. Furthermore, the resulting sulfur copolymer carried reactive amine moieties that were further reacted with comonomers, such as, isocyanates, acid chlorides, epoxides, carboxylic acids, esters, amides, alkyl halides, or acrylates to either modify the sulfur copolymer, or make new copolymeric materials, such as, polyamides, polyurethanes, polyamides, and polyethers.

As used herein, the term "thiol monomer" is a monomer that is polymerizable through its thiol groups. Thiol monomers include, but are not limited to, 4,4'-thiobisbenzenethiol and the like. The term "sulfide monomers" are those that are polymerizable through its sulfide groups.

As used herein, an alkynylly unsaturated monomer is a monomer that is polymerizable through its alkynyl unsaturation (i.e., its triple bond). The term "alkynylly unsaturated monomer" does not include compounds in which the alkynyl unsaturation is part of a long chain alkyl moiety (e.g., unsaturated fatty acids, or carboxylic salts, or esters such as oleates, and unsaturated plant oils). In one embodiment, aromatic alkynes, both internal and terminal alkynes, multi-functional alkynes may be used. Examples of alkynylly unsaturated monomers include, but are not limited to, ethynylbenzene, 1-phenylpropyne, 1,2-diphenylethyne, 1,4-diethynylbenzene, 1,4-bis(phenylethynyl)benzene, and 1,4-diphenylbuta-1,3-diyne.

As used herein, the term "nitrone monomer" is a monomer that is polymerizable through its nitrone groups. In one embodiment, nitrones, dinitrones, and multi-nitrones may be used. Examples include, but are not limited to, N-benzylidene-2-methylpropan-2-amine oxide.

As used herein, the term "aldehyde monomer" is a monomer that is polymerizable through its aldehyde groups. In one embodiment, aldehydes, dialdehydes, and multi-aldehydes may be used.

As used herein, the term "ketone monomer" is a monomer that is polymerizable through its ketone groups. In one embodiment, ketones, diketones, and multi-ketones may be used.

As used herein, the term "epoxide monomer" is a monomer that is polymerizable through its epoxide group(s). Non-limiting examples of such monomers include, generally, mono- or polyoxiranylbenzenes, mono- or polyglycidylbenzenes, mono- or polyglycidyloxybenzenes, mono- or polyoxiranyl(hetero)aromatic compounds, mono- or polyglycidyl(hetero)aromatic compounds, mono- or polyglycidyloxy(hetero)aromatic compounds, diglycidyl bisphenol A ethers, mono- or polyglycidyl(cyclo)alkyl ethers, mono- or polyepoxy(cyclo)alkane compounds and oxirane-terminated oligomers. In one preferred embodiment, the epoxide monomers may be benzyl glycidyl ether and tris(4-hydroxyphenyl)methane triglycidyl ether. In certain embodiments, the epoxide monomers may include a (hetero)aromatic moiety such as, for example, a phenyl, a pyridine, a triazine, a pyrene, a naphthalene, or a polycyclic (hetero)aromatic ring system, bearing one or more epoxide groups. For example, in certain embodiments, the one or more epoxide monomers are selected from epoxy(hetero)aromatic compounds, such as styrene oxide and stilbene oxide and (hetero)aromatic glycidyl compounds, such as glycidyl phenyl ethers (e.g., resorcinol diglycidyl ether, glycidyl 2-methylphenyl ether), glycidylbenzenes (e.g., (2,3-epoxypropyl)benzene) and glycidyl heteroaromatic compounds (e.g., N-(2,3-epoxypropyl)phthalimide). In certain desirable embodiments, an epoxide monomer will have a boiling point greater than 180° C., greater than 200° C., or even greater than 230° C. at the pressure at which polymerization is performed (e.g., at standard pressure, or at other pressures).

As used herein, the term "thiirane monomer" is a monomer that is polymerizable through its thirane group(s). Non-limiting examples of thiirane monomers include, generally, mono- or polythiiranylbenzenes, mono- or polythiiranylmethylbenzenes, mono- or polythiiranyl(hetero)aromatic compounds, mono- or polythiiranylmethyl(hetero)aromatic compounds, dithiiranylmethyl bisphenol A ethers, mono- or polydithiiranyl (cyclo)alkyl ethers, mono- or polyepisulfide(cyclo)alkane compounds, and thiirane-terminated oligomers. In some embodiments, thiirane monomers may include a (hetero)aromatic moiety such as, for example, a phenyl, a pyridine, a triazine, a pyrene, a naphthalene, or a poly cyclic (hetero)aromatic ring system, bearing one or more thiirane groups. In certain desirable embodiments, a thiirane monomer will have a boiling point greater than 180° C., greater than 200° C., or even greater than 230° C. at the pressure at which polymerization is performed (e.g., at standard pressure).

As used herein, an ethylenically unsaturated monomer is a monomer that is polymerizable through its ethylenic unsaturation (i.e., its double bond). The term "ethylenically unsaturated monomer" does not include cyclopentadienyl species such as cyclopentadiene and dicyclopentadiene. The term "ethylenically unsaturated monomer" does not include compounds in which the ethylenic unsaturation is part of a long chain alkyl moiety (e.g. unsaturated fatty acids such as oleates, and unsaturated plant oils).

In certain embodiments, the one or more ethylenically unsaturated monomers are selected from the group consisting of vinyl monomers, (meth)acryl monomers, unsaturated hydrocarbon monomers, and ethylenically-terminated oligomers. Examples of such monomers include, generally, mono- or polyvinylbenzenes, mono- or polyisopropenylbenzenes, mono- or polyvinyl(hetero)aromatic compounds, mono- or polyisopropenyl(hetero)aromatic compounds, alkylene di(meth)acrylates, bisphenol A di(meth)acrylates, benzyl (meth)acrylates, phenyl(meth)acrylates, heteroaryl (meth)acrylates, terpenes (e.g., squalene) and carotene. As molten sulfur is non-polar in character, in certain desirable embodiments the one or more ethylenically unsaturated monomers are non-polar. For example, in certain embodiments, the one or more ethylenically unsaturated monomers include a (hetero)aromatic moiety such as, for example, phenyl, pyridine, triazine, pyrene, naphthalene, or a polycyclic (hetero)aromatic ring system, bearing one or more vinylic, acrylic or methacrylic substituents. Examples of such monomers include benzyl (meth)acrylates, phenyl (meth)acrylates, divinylbenzenes (e.g., 1,3-divinylbenzene, 1,4-divinylbenzene), isopropenylbenzene, styrenics (e.g., styrene, 4-methylstyrene, 4-chlorostyrene, 2,6-dichlorostyrene, 4-vinylbenzyl chloride), diisopropenylbenzenes (e.g., 1,3-diisopropenylbenzene), vinylpyridines (e.g., 2-vinylpyridine, 4-vinylpyridine), 2,4,6-tris((4-vinylbenzyl)thio)-1,3,5-triazine and divinylpyridines (e.g., 2,5-divinylpyridine). In certain embodiments, the one or more ethylenically unsaturated monomers (e.g., including an aromatic moiety) bears an amino (i.e., primary or secondary) group, a phosphine group or a thiol group. One example of such a monomer is vinyldiphenylphosphine. While not intending to be bound by theory, the inventors surmise that the amino or thiol group will undergo a ring-opening nucleophilic attack on an $S_8$ ring, thus incorporating a short sulfide chain that promotes solubility in molten sulfur. Of course, a person of skill in the art will identify other ethylenically unsaturated monomers that can be used in forming the copolymers described herein. In certain desirable embodiments, an ethylenically unsaturated monomer will have a boiling point greater than 180° C., greater than 200° C., or even greater than 230° C. at the pressure at which polymerization is performed (e.g., at standard pressure).

As used herein, an "elemental carbon material" is a material that is primarily formed as an allotrope of carbon, with a minor amount of chemical modification. For example, graphene, graphene oxide, graphite, carbon nanotubes, fullerenes, carbon black, carbon flakes and carbon fibers are examples of elemental carbon materials. Such materials can be made, for example, by first dispersing the elemental carbon material in molten sulfur, then copolymerizing the molten sulfur with one or more monomers (e.g., one or more polyfunctional monomers). As a general guideline for the person of skill in the art to use in formulating such materials, up to about 15 wt % elemental carbon material can be dispersed in sulfur at temperatures high enough that the sulfur is molten, but low enough that significant ring opening and polysulfide polymerization does not occur (e.g., at temperatures in the range of about 120° C. to about 160° C.). Higher loadings of elemental carbon materials in sulfur can be achieved by pre-dissolution of the sulfur and dispersion of the elemental carbon material into a suitable solvent (e.g., carbon disulfide) followed by removal of the solvent under reduced pressure to yield a blended composite powder which can be melted and allowed to with the one or more monomers. To induce curing of the dispersed carbon, or other nanoindusions with the sulfur matrix, direct heating of the dispersion above T=160° C., typically below 200° C. affords a polymerized nanocomposite.

As used herein, the term "self-healing" is defined as to enable a material to repair damage with minimum intervention[2]. In some embodiments, mechanisms and techniques to enable self-healing may include covalent bonding, supramolecular chemistry, H-bonding, ionic interactions, π-π stacking, chemo-mechanical repairs focusing on encapsulation, remote self-healing, or shape memory assisted polymers[2]. In one preferred embodiment, self-healing utilizes thermal reformation. As used herein, thermal reformation involves the use of heat to reform the bonds or cross-links of a polymeric material.

As used herein, the term "photoactive" is defined as having the ability for significant absorption of solar, visible or near-infrared radiation As used herein, the term "biocompatible" and any of it analogues are defined as the ability of to be in contact with living tissues without producing any undesirable local or systemic effects, such as toxicity. As used herein, the term "soluble" and any of its analogues are defined as being capable of dissolving in another medium, such as a solid, a liquid, or gas.

As defined herein, the terms "therapeutically effective amount" means the amount of a compound that, when administered to a mammal for treating a condition, is sufficient to effect such treatment for the condition. The "therapeutically effective amount" will vary depending on the compound, the condition and its severity and body factors such as age, weight, etc., of the mammal to be treated.

As used herein, the term "slow and continuous release" is defined as the ability to maintain a controlled presence of a chemical in the body without any sudden increases, decreases, or stops in the amount of the chemical that may cause toxicity or hinder the therapeutic effectiveness of the chemical in the body.

As defined herein, the terms "Treating" or "treatment" of a condition includes: (1) preventing the condition, i.e., causing the clinical symptoms of the condition not to develop in a mammal that may be exposed to or predisposed to the condition but does not yet experience or display symptoms of the condition; (2) inhibiting the condition, i.e., arresting or reducing the development of the condition or its clinical symptoms; or (3) relieving the condition, i.e., causing regression of the condition or its clinical symptoms.

As used herein, the terms "those defined above" and "those defined herein" when referring to a variable incorporates by reference the broad definition of the variable as well as any narrow and/or preferred, more preferred and most preferred definitions, if any.

Copolymer Material

The synthesis of copolymer materials via the copolymerization of elemental sulfur with comonomers is taught. The copolymer material comprises comonomers of sulfur, ethylenically unsaturated monomers (e.g., vinylic, divinylic, multi-vinylic comonomers, substituted alkenes, and functional alkenes), alkynylly unsaturated monomer (e.g., alkynes, dialkynes, and multi-alkynes), amine monomers (e.g., amines, diamines, and multi-amines), thiol monomer (e.g., thiols, dithiols, multi-functional thiols), nitrone and nitroso monomers (e.g., nitrones, dinitrones, and multinitrones), aldehyde monomers (e.g., aldehydes, dialdehydes, and multi-aldehydes), and ketone monomers.

New types of copolymers incorporated conjugated polymers with sulfur based materials and copolymers were prepared by the copolymerization of elemental sulfur with vinylic compounds carrying thiophene, or amine, or pyrrole side chain groups, where subsequent oxidative or electrochemical polymerization affords the new copolymer material. Vinylic monomers, utilizing groups, such as, styrenics, incorporating thiophene groups, such as, 3,4-alkylenedioxythiophenes and 3,4-propylenedioxythiophenes (ProDOT) are examples of these functional monomers.

New conjugated materials are also demonstrated by the copolymerization of elemental sulfur with amines e.g., phenylenediamines that can be oxidatively copolymerized with aniline to prepare polyaniline-sulfur copolymer materials.

A new material prepared by post-modification of the amine, thiol, or other functional groups may be incorporated into the sulfur copolymer described to either modify the chemical functionality of the copolymer, crosslink the copolymer, or form other new copolymers, such as, polyethers via epoxide copolymerizations, polyurethanes and polyamides.

In one embodiment, the copolymer material with sulfur is prepared via distinct synthesis and post-functionalization methods to introduce conjugated polymers, such as, polythiophenes, polyanilines, or polypyrroles. Methods include, but are not limited to, the copolymerization of a vinylic comonomer carrying a pendant thiophene that forms the polythiophene phase after an oxidative, or electrochemical polymerization. Other methods include copolymerization of sulfur with diamines that carry free reactive amines that can copolymerize with monomers, such as, aniline, and then oxidative or electrochemical polymerization to form the polyaniline phase.

In some embodiments, the present invention features a polymeric composition comprising a sulfur copolymer. The sulfur copolymer comprises one or more sulfur monomers, at a level in the range of at least about 50 wt % of the sulfur copolymer, and one or more monomers selected from a group consisting of amine monomers, thiol monomers, sulfide monomers, alkynylly unsaturated monomers, nitrone monomers, aldehyde monomers, ketone monomers, thiirane monomers, epoxide monomers, and ethylenically unsaturated monomers at a level in the range of about 0.1 wt % to about 50 wt % of the sulfur copolymer. In some embodiments, the ethylenically unsaturated monomers are present as copolymers with at least one additional monomer. Non-limiting examples of other monomers are described in U.S. Provisional Patent Application No. 61/940,102, filed Feb. 14, 2014, which are incorporated herein by reference.

In some embodiments, the one or more monomers are one or more amine monomers. The amine monomer may be an m-phenylenediamine or p-phenylenediamine. In some embodiments, the one or more monomers are one or more thiol monomers. The thiol monomer may be 4,4'-thiobis(benzenethiol). In some embodiments, the one or more monomers are a combination of one or more amine monomers and one or more thiol monomers. In other embodiments, the one or more monomers are one or more alkynylly unsaturated monomers. The alkynylly unsaturated monomer may be 1-phenylpropyne.

In some embodiments, the sulfur copolymer of any polymeric composition, copolymer material, or composite material mentioned herein comprises one or more sulfur monomers at a level in the range of about 5 to about 99 wt % of the sulfur copolymer, and one or more monomers at a level in the range of about 1 wt % to about 95 wt % of the sulfur copolymer. In another embodiment, the sulfur copolymer comprises one or more sulfur monomers at a level in the range of about 50 to about 97.5 wt % of the sulfur copolymer, and one or more monomers at a level in the range of about 2.5 wt % to about 50 wt % of the sulfur copolymer, or one or more sulfur monomers at a level in the range of about 50 to about 95 wt % of the sulfur copolymer, and one or more monomers at a level in the range of about 5 wt % to about 50 wt % of the sulfur copolymer.

In some embodiments, the sulfur copolymer of any polymeric composition, copolymer material, or composite material mentioned herein comprises one or more sulfur monomers at a level of at least about 5 wt % of the sulfur copolymer. The sulfur copolymer may comprise one or more sulfur monomers at a level of at least about 10 wt %, or at least about 20 wt %, or at least about 30 wt %, or at least about 40 wt %, or at least about 50 wt %, or at least about 60 wt %, or at least about 70 wt %, or at least about 80 wt %, or at least about 90 wt % of the sulfur copolymer.

In some embodiments, the sulfur copolymer of any polymeric composition, copolymer material, or composite material mentioned herein comprises one or more sulfur monomers at a level in the range of about 5 to about 10 wt % of the sulfur copolymer. The sulfur copolymer may comprise one or more sulfur monomers at a level in the range of about 10 to 20 wt %, or in the range of about 20 to 30 wt %, or in the range of about 30 to 40 wt %, or in the range of about 40 to 50 wt %, or in the range of about 50 to 60 wt %, or in the range of about 60 to 70 wt %, or in the range of about 70 to 80 wt %, or in the range of about 80 to 90 wt %, or in the range of about 90 to 95 wt % of the sulfur copolymer.

In some embodiments, the sulfur copolymer of any polymeric composition, copolymer material, or composite material mentioned herein comprises one or more monomers at a level of at least 0.1 wt % of the sulfur copolymer. The sulfur copolymer may comprise one or more monomers at a level of at least about 0.5 wt %, or at least about 1 wt %, or at least about 5 wt %, or at least about 10 wt %, or at least about 20 wt %, or at least about 30 wt %, or at least about 40 wt %, or at least about 50 wt %, or at least about 60 wt %, or at least about 70 wt %, or at least about 80 wt %, or at least about 90 wt %, or at least about 95 wt % of the sulfur copolymer.

In some embodiments, the sulfur copolymer of any polymeric composition, copolymer material, or composite material mentioned herein comprises one or more monomers at a level in the range of about 0.1 wt % to 0.5 wt % of the sulfur copolymer. The sulfur copolymer may comprise one or more monomers at a level in the range of about 0.5 wt % to 1 wt %, or about 1 wt % to 5 wt %, or about 5 wt % to 15 wt %, or about 15 wt % to 25 wt %, or about 25 wt % to 35 wt %, or about 35 wt % to 45 wt %, or about 45 wt % to 55 wt %, or about 55 wt % to 65 wt %, or about 65 wt % to 75 wt %, or about 75 wt % to 85 wt %, or about 85 wt % to 95 wt % of the sulfur copolymer.

In some embodiments, the polymeric composition may be in the form of a polymeric composite comprising the sulfur copolymer and an elemental carbon material dispersed in the copolymer at a level in the range of up to about 50 wt % of the composition. In some embodiments, the polymeric composition may comprise the sulfur and comonomers at a level in the range of about 10 to 20 wt %, or in the range of about 20 to 30 wt %, or in the range of about 30 to 40 wt %, or in the range of about 40 to 50 wt %, or in the range of about 50 to 60 wt %, or in the range of about 60 to 70 wt %, or in the range of about 70 to 80 wt %, or in the range of about 80 to 90 wt %, or in the range of about 90 to 95 wt % of the polymeric composition. In some embodiments, the polymeric composition may comprise the elemental carbon material at a level in the range of about 10 to 20 wt %, or in the range of about 20 to 30 wt %, or in the range of about 30 to 40 wt %, or in the range of about 40 to 50 wt %, or in the range of about 50 to 60 wt %, or in the range of about 60 to 70 wt %, or in the range of about 70 to 80 wt %, or in the range of about 80 to 90 wt %, or in the range of about 90 to 95 wt % of the polymeric composition.

In some embodiments, the present invention features a method for making any of the aforementioned polymeric compositions. The method comprises heating a mixture comprising sulfur and one or more monomers at a temperature in the range of about 120° C. to about 230° C.

In some embodiments, an article is made from any of the aforementioned polymeric compositions. The method of forming the article comprises heating a mixture comprising sulfur and one or more monomers at a temperature in the range of about 160° C. to about 230° C. to form a prepolymer, forming the prepolymer into the shape of the article, to yield a formed prepolymer shape, and heating the formed prepolymer shape to yield the article.

In another embodiment, a method of forming the article comprises admixing the polymeric composition in a nonpolar organic solvent, forming the admixed polymeric composition into the shape of the article, and removing the solvent from the polymeric composition to yield the article.

In some embodiments, the prepolymer is provided as a mixture with a solvent for forming. In other embodiments, the prepolymer is coated and cured as a thin film on a substrate. In still other embodiments, the prepolymer is shaped and cured using a mold.

In some embodiments, an oil-in-water emulsion comprises the polymeric composition as the colloidal phase suspended in aqueous solution with, or without the presence of a surfactant.

In some embodiments, any of the polymeric composition can be modified by reacting an available reactive functional group on the polymeric composition with a second comonomer to form a new copolymer material. The technique of reacting may be oxidative coupling, polymerization, or copolymerization.

In some embodiments, the reactive functional group is an amine or a thiol. The second comonomer may comprise an epoxide, isocyanate, acid chloride, carboxylic acid, ester, or alkyl halide group. In some embodiments, when the reactive functional group is an amine, the new copolymer material is a polyurethane or a polyamide. In some embodiments, when the reactive functional group is an aniline or a phenylenediamine, and the new copolymer material contains oligo- or polyaniline segments. In some embodiments, the reactive functional group is a thiophene and the new copolymer material contains oligo- or polythiophene segments.

EXAMPLES

Example 1. General Procedure for the Inverse Vulcanization of Sulfur with Alkynes A 5 mL vial equipped with a magnetic stir bar was loaded with sulfur (800 mg, 3.125 mmol) and 1-phenylpropyne (0.20 mL, 1.72 mmol). The mixture was stirred at 175° C. for 7 min yielding a very viscous red transparent fluid. The reaction was quenched by cooling to −78° C. The resulting poly(sulfur-co-phenylpropyne) was then recovered from the vial yielding a reddish brown solid (949 mg, 96%).

Monoalkyne Examples

Scheme

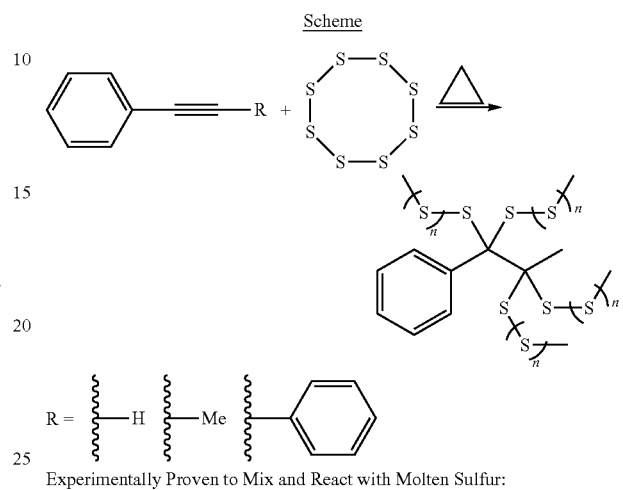

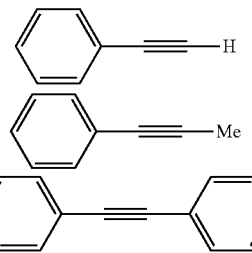

Experimentally Proven to Mix and React with Molten Sulfur:

Dialkyne Examples

Scheme

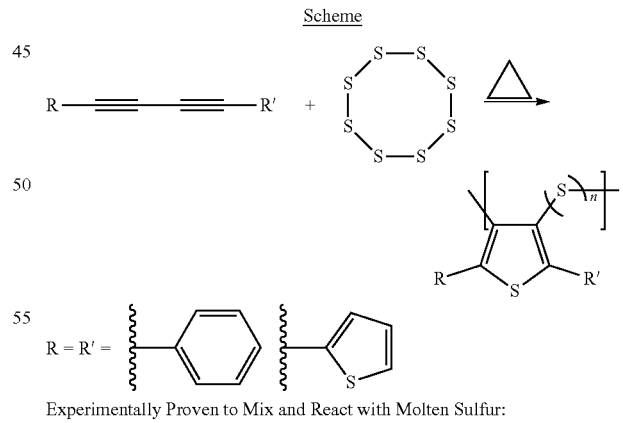

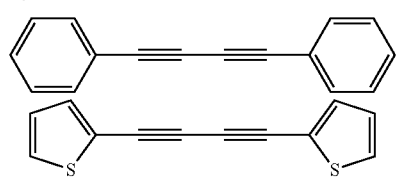

Experimentally Proven to Mix and React with Molten Sulfur:

Multi-Alkyne Examples

Scheme

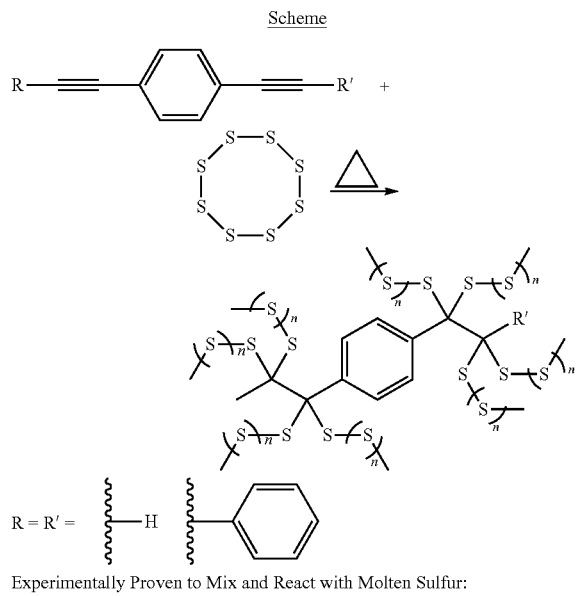

Experimentally Proven to Mix and React with Molten Sulfur:

Example 2. General Procedure for the High Temperature Preparation of Poly(Sulfur-Random-(m-Phenylenediamine) (Poly(S-r-m-PDA)) Copolymers To a 24 mL glass vial equipped with a magnetic stir bar were added sulfur ($S_8$, masses detailed below) and m-phenylenediamine (m-PDA, masses detailed below). The reaction was heated to about T=185° C. in a thermostat oil bath and the resulting mixture was stirred at about T=185° C. for 8-10 minutes, until bubbling ceased and vitrification of the reaction media occurred.

Preparation of poly(S-r-m-PDA) with 50-wt % m-PDA

The copolymerization was carried out by following the general method written above with $S_8$ (2.5 g, 9.75 mmol) and m-PDA (2.5 g, 23.13 mmol) to afford a blood red solid.

Preparation of poly(S-r-m-PDA) with 33.3-wt % m-PDA

The copolymerization was carried out by following the general method written above with $S_8$ (2.5 g, 9.75 mmol) and m-PDA (1.25 g, 11.56 mmol) to afford a blood red solid.

Preparation of poly(S-r-m-PDA) with 28.57-wt % m-PDA

The copolymerization was carried out by following the general method written above with $S_8$ (2.5 g, 9.75 mmol) and m-PDA (1.0 g, 9.25 mmol) to afford a blood red solid.

Preparation of poly(S-r-m-PDA) with 23.08-wt % m-PDA

The copolymerization was carried out by following the general method written above with $S_8$ (2.5 g, 9.75 mmol) and m-PDA (0.75 g, 6.94 mmol) to afford a blood red solid.

Preparation of poly(S-r-m-PDA) with 16.67-wt % m-PDA

The copolymerization was carried out by following the general method written above with $S_8$ (2.5 g, 9.75 mmol) and m-PDA (0.5 g, 4.63 mmol) to afford a blood red solid.

Preparation of poly(S-r-m-PDA) with 9.09-wt % m-PDA

The copolymerization was carried out by following the general method written above with $S_8$ (2.5 g, 9.75 mmol) and m-PDA (0.25 g, 2.31 mmol) to afford a blood red solid.

As shown in FIGS. 16a-16d, the copolymer made from $S_8$ and 1,3-phenylenediamine at T=185° C., or 135° C. is homogeneous red glasses, which exhibits characteristically different appearances than the starting materials ($S_8$ is yellow crystalline powder and 1,3-phenylenediamine is a white powder). Furthermore, the product of the copolymerization of $S_8$ and with other isomers of phenylenediamines, such as 1,4-phenylenediamine, afford a heterogeneous, chalk-like material composed of yellow and brown particulates.

Example 3. General Procedure for the High Temperature Preparation of poly(sulfur-random-(4,4'-thiobisbenzenethiol) (poly(S-r-TBBT)) Copolymers To a 24 mL glass vial equipped with a magnetic stir bar were added sulfur ($S_8$, masses detailed below) and 4,4'-thiobisbenzenethiol (TBBT, masses detailed below). The reaction was heated to T=185° C. in a thermostat oil bath and the resulting mixture was stirred at T=185° C. for 8-10 minutes, until bubbling ceased.

Preparation of poly(S-r-TBBT) with 50-wt % TBBT

The copolymerization was carried out by following the general method written above with $S_8$ (0.50 g, 1.95 mmol) and TBBT (0.5 g, 2.00 mmol) to afford a yellow solid.

Preparation of poly(S-r-p-PDA) with 33.3-wt % TBBT

The copolymerization was carried out by following the general method written above with $S_8$ (0.66 g, 2.57 mmol) and TBBT (0.33 g, 1.32 mmol) to afford a yellow solid.

Preparation of poly(S-r-p-PDA) with 28.57-wt % TBBT

The copolymerization was carried out by following the general method written above with $S_8$ (0.714 g, 2.78 mmol) and TBBT (0.286 g, 1.14 mmol) to afford a yellow solid.

Preparation of poly(S-r-p-PDA) with 23.08-wt % TBBT

The copolymerization was carried out by following the general method written above with $S_8$ (0.769 g, 3.00 mmol) and TBBT (0.231 g, 0.92 mmol) to afford a yellow solid.

Preparation of poly(S-r-p-PDA) with 16.67-wt % TBBT

The copolymerization was carried out by following the general method written above with $S_8$ (0.833 g, 3.25 mmol) and TBBT (0.166 g, 0.663 mmol) to afford a yellow solid.

Preparation of poly(S-r-p-PDA) with 9.09-wt % TBBT

The copolymerization was carried out by following the general method written above with $S_8$ (0.909 g, 3.54 mmol) and TBBT (0.091 g, 0.363 mmol) to afford a yellow solid.

Example 4. Nitrone Capping of Sulfur Copolymers

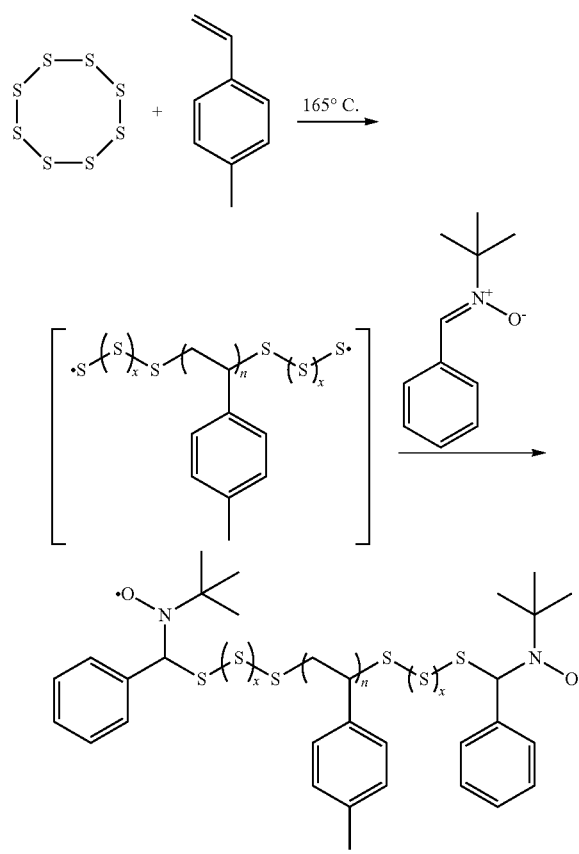

To a 5 mL vial equipped with a magnetic stir bar was added elemental sulfur (500 mg). The vial was heated to 165° C. until the sulfur completely melted. 4-methylstyrene (0.5 mL) was then added and the mixture was stirred at 165° C. for 50 min. N-tert-butyl-α-phenylnitrone (0.175 mg) was then added and the reaction was stirred for an additional 10 min at 165° C. The polymer was isolated by precipitation into an excess of rapidly stirred methanol and recovered via centrifugation as a yellow powder.

Reaction of other nitrones include, 5,5-dimethyl-1-pyrroline-N-oxide, difunctional aromatic nitrones and other aliphatic nitrones was demonstrated to copolymerize with sulfur

Example 5. Conjugated Polymers with Aniline, Diamines and Sulfur

Experimental

Figure 17:
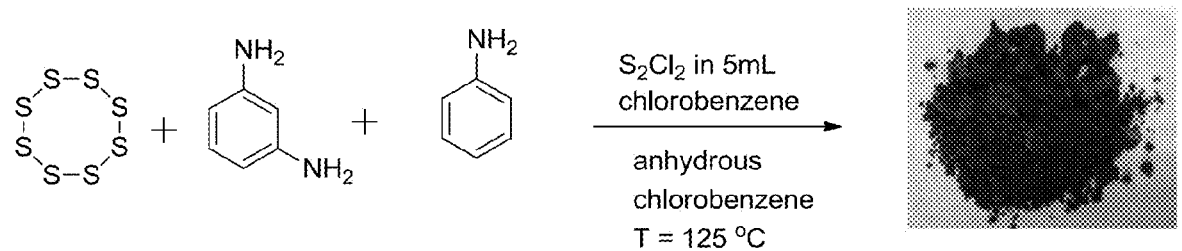
FIG. 17 shows a reaction scheme and final copolymer product.

To a 50 mL 3-neck RBF equipped with a magnetic stir bar and a condenser were added the sulfur (4.25 g, 16.858 mmol), m-phenylenediamine (0.25 g, 2.312 mmol), DIB (0.5 g, 0.54 mL, 3.160 mmol), aniline (0.215 g, 0.211 mL, 2.312 mmol), and chlorobenzene (10 mL). The other two necks were fitted with septa and placed in a thermostat controlled oil bath held at T=125° C. and once the reaction was homogenous it was run for 2 hours while stirring at 800 rpm. Into vial fitted with a rubber septum were added the sulfur monochloride (3.123 g, 1.85 mL, 23.125 mmol) and chlorobenzene (5 mL). After 2 hours the sulfur monochloride solution was injected into the stirring copolymer. The heat to the reaction was turned off and the reaction was run for an additional hour to homogenize and ensure complete reaction and removal of the HCl gas that is generated. After the reaction is complete the mixture was precipitated into stirring anhydrous ethanol. The precipitate was filtered and then washed with deionized (DI) $H_2O$ (3×25 mL), saturated sodium bicarbonate solution (3×25 mL), DI $H_2O$ once again to remove any salt products (2×25 mL), anhydrous ethanol (2×25 mL) and finally the sample was washed with a mixture of carbon disulfide and tetrahydrofuran (1:1 by volume) until the washings were clear. The product was then dried and weighed. A reaction scheme and final product is shown in FIG. 17.

Example 6. Conjugated Polymers with Sulfur and Thiophenes

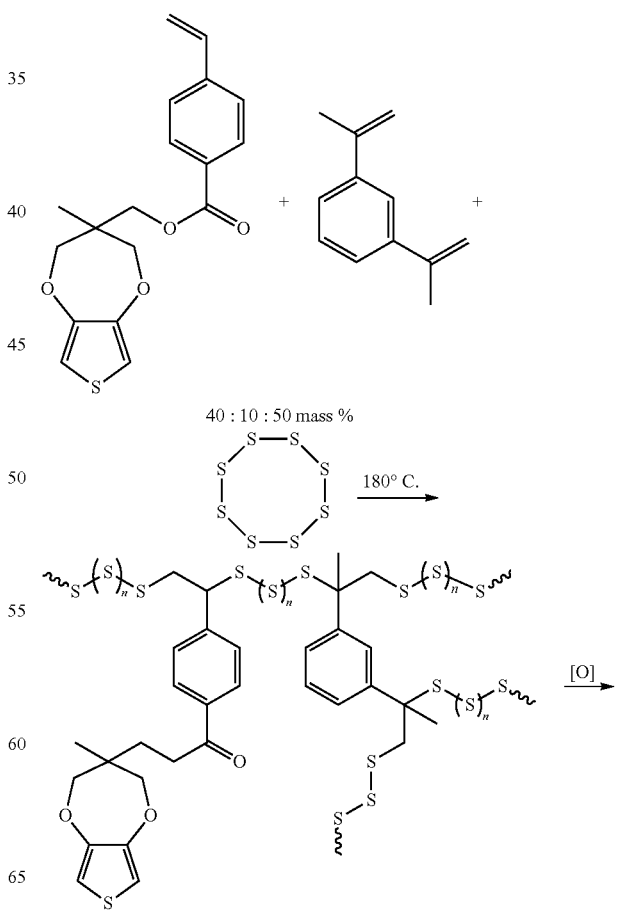

-continued

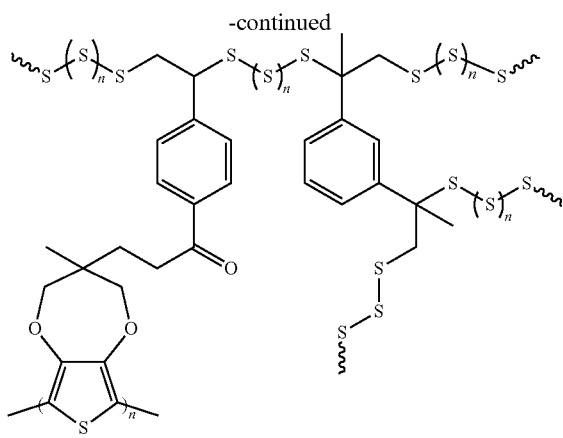

Preparation of poly(ProDOT-Sty-r-DIB-r-S) (ProDIBS)

To a 5 mL glass vial equipped with a magnetic stir bar was added elemental sulfur (500 mg, 1.95 mmol) and ProDOT-Sty (400 mg, 1.21 mmol). The mixture was heated to 180° C. with rapid stirring for 5 min to facilitate the oligomerization of sulfur and ProDOT-Sty yielding a viscous orange liquid. 1,3-Diisopropenyl benzene (100 mg, 108 μL, 0.63 mmol) was then injected and the reaction was allowed to stir at 180° C. until vitrification occurred (~5 additional minutes). The sample was cooled to −78° C. in a dry ice/acetone bath and extracted by breaking the glass vial yielding a dark red glass in quantitative yield. The copolymer of poly (ProDOT-Sty, 1,3-diisopropenylbenzene and sulfur is defined as poly(ProDIBS).

Oxidative Polymerization of Pendant ProDOT Groups in ProDIBS

In Solution (Chemical):

To a 20 mL scintillation vial were added poly(ProDOT-Sty-r-DIB-r-S) (ProDIBS) (450 mg) and anhydrous $CH_2Cl_2$ (5 mL). The mixture was mixed using a vortex mixer until a homogeneous reddish orange solution resulted. A 50 mL round bottom flask equipped with a magnetic stir bar was then loaded with phenyliodine bis(trifluoroacetate) (PIFA) (5.86 g, 13.63 mmol) and evacuated/backfilled with Ar. Anhydrous $CH_2Cl_2$ (12 mL) was added and the mixture was allowed to stir until the solution was saturated (~10 min). Borontrifluoride diethyletherate (3.36 mL, 27.25 mmol) was then slowly added to the PIFA/$CH_2Cl_2$ mixture under Argon yielding a homogeneous yellow solution. The PIFA/$BF_3.Et_2O$ solution was cooled to 0° C. in an ice bath and the ProDIBS solution was added drop wise. After addition of the ProDIBS was complete the reaction was allowed to come to room temperature and stirred under Ar for 2 hours. The dark purple/black solution was then slowly added to a 10 fold excess of rapidly stirred MeOH. The resulting precipitate was recovered via vacuum filtration, washed with additional MeOH and dried in vacuo at room temperature, yielding the polymer as a dark green powder (408 mg yield).

On Electrode (Electrochemical):

A thin film of ProDIBS (ca. 240 nm thickness) was deposited onto a freshly cleaned ITO coated glass substrate (2 cm×2 cm) by spin-coating from a solution of poly (ProDIBS) in volume mixed solvent system of toluene and $CH_2Cl_2$ (1:1 vol-ratio) (25 mg/mL) with a two-step spin-coating protocol (step 1: ramp at 400 rpm/s to 1500 rpm for a total of 15 s, step 2: ramp at 665 rpm/s from 1500 to 3500 rpm for an additional 15 s). The ProDIBS coated ITO was then placed in an electrochemical cell with a Pt counter electrode and 100 mM tetrabutylammonium hexafluorophosphate (TBAFP) in MeCN. The polymer film was incubated in the TBAFP solution for 5 min to allow for swelling of the polymer with electrolyte. Oxidative polymerization of the ProDOT moieties was then carried out by stepping the potential to 1.1 V vs. Ag/Ag$^+$.

Sulfur Copolymers with Sulfur and Sulfides

Non-limiting examples of sulfide monomers include 2,2'dipyridyldisulfides, functional 2,2'dipyridyldisulfides, 1,3-phenylenedimethanedithiol, and other dithiol isomers (e.g., 1,4 and 1,2 dithiols, and functional dithiols).

Preparation of the Sulfur Copolymer

The $S_8$ and the sulfide were mixed together is vessel equipped with a magnetic stir bar. The reaction was heated to a temperature between about T=120° C. to 200° C. in a thermostat oil bath and the resulting mixture was stirred about for 6-10 minutes to afford a sulfur copolymer material.

Sulfur Copolymers with Sulfur and Aldehydes

Non-limiting examples of aldehyde monomers include 4-vinylbenzaldehyde and phthalaldehyde.

Preparation of the Sulfur Copolymer

The $S_8$ and the aldehyde were mixed together is vessel equipped with a magnetic stir bar. The reaction was heated to a temperature between about T=120° C. to 200° C. in a thermostat oil bath and the resulting mixture was stirred about for 6-10 minutes to afford a sulfur copolymer material.

Sulfur Copolymers with Sulfur and Ketones

Non-limiting examples of ketone monomers include 1-(4-vinylphenyl)ethan-1-one.

Preparation of the Sulfur Copolymer

The $S_8$ and the ketone were mixed together is vessel equipped with a magnetic stir bar. The reaction was heated to a temperature between about T=120° C. to 200° C. in a thermostat oil bath and the resulting mixture was stirred about for 6-10 minutes to afford a sulfur copolymer material.

Preparation of the Sulfur Copolymer

The $S_8$ and the sulfide were mixed together is vessel equipped with a magnetic stir bar. The reaction was heated to a temperature between about T=120° C. to 200° C. in a thermostat oil bath and the resulting mixture was stirred about for 6-10 minutes to afford a sulfur copolymer material.

Self-Healing

Another feature of the present invention is a copolymer material comprising a sulfur copolymer at a level in the range of about 5 wt % to about 95 wt % of the copolymer material, and one or more epoxide monomers at a level in the range of about 5 wt % to about 95 wt % of the copolymer material. In some embodiments, the sulfur copolymer comprises one or more sulfur monomers, at a level at least about 50 wt % of the sulfur copolymer, and one or more comonomers each selected from a group consisting of amine monomers, thiol monomers, sulfide monomers, alkynylly unsaturated monomers, nitrone monomers, aldehyde monomers, ketone monomers, thiirane monomers, and ethylenically unsaturated monomers at a level in the range of about 0.1 wt % to about 50 wt % of the sulfur copolymer. In some embodiments, at least one epoxy functional group of the epoxide monomers is bonded to a functional group of the sulfur copolymer. Non-limiting examples of other monomers are described in U.S. Provisional Patent Application No. 62/039,561, filed Aug. 20, 2014, which are incorporated herein by reference.

In some embodiments, the one or more comonomers are one or more amine monomers. In some embodiments, the amine monomer is m-phenylenediamine or p-phenylenediamine. In some embodiments, the one or more comonomers are one or more thiol monomers. In some embodiments, the thiol monomer is 4,4'-thiobis(benzenethiol). In some embodiments, the one or more comonomers are a combination of one or more amine monomers and one or more thiol monomers. In some embodiments, the one or more comonomers are one or more alkynylly unsaturated monomers. In some embodiments, the alkynylly unsaturated monomer is 1-phenylpropyne. In some embodiments, the one or more comonomers are one or more thiirane monomers. In some embodiments, the thiirane monomer is propylene sulfide. In some embodiments, one or more of the epoxide monomers are benzyl glycidyl ether, tris(4-hydroxyphenyl)methane triglycidyl ether, or a combination thereof.

In some embodiments, the sulfur copolymer is at a level of at least about 5 wt %, or at least about 10 wt %, or at least about 20 wt %, or at least about 30 wt %, or at least about 40 wt %, or at least about 50 wt %, or at least about 60 wt %, or at least about 70 wt %, or at least about 80 wt %, or at least about 90 wt %, or at least about 95 wt % of the copolymer material. In some embodiments, the sulfur copolymer is at a level between about 5 and 10 wt %, or about 10 and 15 wt %, or about 15 and 20 wt %, or about 20 and 30 wt %, or about 30 and 40 wt %, or about 40 and 50 wt %, or about 50 and 60 wt %, or about 60 and 70 wt %, or about 70 and 80 wt %, or about 80 and 90 wt %, or about 90 and 95 wt % of the copolymer material.

In some embodiments, the epoxide monomer is at a level of at least about 1 wt % of the copolymer material. The epoxide monomer may be at a level of at least about 5 wt %, or at least about 10 wt %, or at least about 20 wt %, or at least about 30 wt %, or at least about 40 wt %, or at least about 50 wt %, or at least about 60 wt %, or at least about 70 wt %, or at least about 80 wt %, or at least about 90 wt %, or at least about 95 wt % of the copolymer material. In some embodiments, the epoxide monomer is at a level between about 1 and 5 wt %, or about 5 and 15 wt %, or about 15 and 25 wt %, or about 25 and 35 wt %, or about 35 and 45 wt %, or about 45 and 55 wt %, or about 55 and 65 wt %, or about 65 and 75 wt %, or about 75 and 85 wt %, or about 85 and 95 wt % of the copolymer material.

In some embodiments, the copolymer material is a thermoset. In some embodiments, the copolymer material is a thermoplastic. In some embodiments, the copolymer material is self-healing. In some embodiments, when one or more S—S bonds of the sulfur copolymer are broken, the S—S bonds are reconnected by thermal reforming.

In some embodiments, the present invention features a self-healing sulfur copolymer comprising one or more sulfur monomers, at a level at least about 50 wt % of the self-healing sulfur copolymer, and one or more comonomers each selected from a group consisting of amine monomers, thiol monomers, sulfide monomers, alkynylly unsaturated monomers, nitrone monomers, aldehyde monomers, ketone monomers, epoxide monomers, thiirane monomers, and ethylenically unsaturated monomers at a level in the range of about 0.1 wt % to about 50 wt % of the self-healing sulfur copolymer. In some embodiments, when one or more S—S bonds of the sulfur copolymer are broken, the S—S bonds are reconnected by thermal reforming.

In some embodiments, the present invention features a self-healing and reworkable epoxy resin comprising a sulfur copolymer at a level in the range of about 5 wt % to about 95 wt % of the epoxy resin, and one or more epoxide monomers at a level in the range of about 5 wt % to about 95 wt % of the epoxy resin. In some embodiments, sulfur copolymer at a level in the range of about 5 to 15 wt %, or about 15 to 25 wt %, or about 25 to 35 wt %, or about 35 to 45 wt %, or about 45 to 55 wt %, or about 55 to 65 wt %, or about 65 to 75 wt %, or about 75 to 85 wt %, or about 85 to 95 wt % of the epoxy resin. In some embodiments, the sulfur copolymer comprising one or more sulfur monomers, at a level at least about 50 wt %, or about 60 wt %, or about 70 wt %, or about 80 wt %, or about 90 wt % of the self-healing sulfur copolymer, and one or more comonomers each selected from a group consisting of amine monomers, thiol monomers, sulfide monomers, alkynylly unsaturated monomers, nitrone monomers, aldehyde monomers, ketone monomers, epoxide monomers, thiirane monomers, and ethylenically unsaturated monomers at a level in the range of about 0.1 wt % to 10 wt %, or about 10 wt % to 20 wt %, or about 20 wt % to 30 wt %, or about 30 wt % to 40 wt %, or about 40 wt % to 50 wt % of the self-healing sulfur copolymer. In some embodiments, at least one epoxy functional group of the epoxide monomers is bonded to a functional group of the sulfur copolymer. In some embodiments, when one or more S—S bonds of the sulfur copolymer are broken, the S—S bonds are reconnected by thermal reforming.

In some embodiments, the present invention features a method of repairing a polymeric substrate, said method comprising providing the polymeric substrate comprising a sulfur copolymer having one or more broken S—S bonds, and heat treating the polymeric substrate at a healing temperature for a period of time in order to reconnect the S—S bonds of the sulfur copolymer. In some embodiments, the sulfur copolymer comprises one or more sulfur monomers, at a level at least about 50 wt % of the self-healing sulfur copolymer, and one or more comonomers each selected from a group consisting of amine monomers, thiol monomers, sulfide monomers, alkynylly unsaturated monomers, nitrone monomers, aldehyde monomers, ketone monomers, epoxide monomers, thiirane monomers, and ethylenically unsaturated monomers at a level in the range of about 0.1 wt % to about 50 wt % of the self-healing sulfur copolymer. In some embodiments, the polymeric substrate further comprises one or more epoxide monomers at a level in the range of about 5 wt % to about 95 wt % of the polymeric substrate, wherein at least one epoxy functional group of the epoxide monomers is bonded to a functional group of the sulfur copolymer.

In some embodiments, the healing temperature is between about 80° C. and 100° C. In some embodiments, the healing temperature is between about 100° C. and 150° C. In some embodiments, the healing temperature is at or near the melting point of the polymeric substrate. In some embodiments, the period of time is between about 4 and 15 hours. In some embodiments, the period of time is between about 8 and 12 hours.

Metal Composites

In some embodiments, the present invention features a composite material comprising a sulfur at a level at least about 50 wt % of the composite material, and a metal or ceramic composite having a formula $M_xR_y$ and at a level between about 0.1 and about 50 wt % of the composite material. In some embodiments, M is selected from a group consisting of Ag, Al, As Au, B, Ba, Bi, Ca, Cd, Ce, Co, Cr, Cu, Eu, Fe, Ga, Gd, Ge, Hf, Hg, In, La, Li, Mg, Mn, Mo, Na, Nb, Nd, Ni, P, Pb, Pd, Pr, Sb, Se, Si, Sn, Sr, Ta, Ti, Tl, V, W, Y, Yb, Zn and Zr. In some embodiments, R is selected from a group consisting of C, N, and S. In some embodiments, x ranges between about 1 and about 30, or between about 1 and about 10, or between about 10 and about 20, or between about 20 and about 30. In some embodiments, y ranges between about 1 and about 5, or between about 5 and about 10, or between about 1 and about 10. In some embodiments, the metal or ceramic composite is dispersed in the sulfur.

In some embodiments, the sulfur is at a level at least about 20 wt % of the composite material. In other embodiments, the sulfur is at a level at least 30 wt %, or about 40 wt %, or about 50 wt %, or about 60 wt %, or about 70 wt %, or about 80 wt %, or about 90 wt % of the composite material. In some embodiments, the sulfur is at a level between about 30-40 wt %, or about 40-50 wt %, or about 50-60 wt %, or about 60-70 wt %, or about 70-80 wt %, or about 80-90 wt % of the composite material.

In some embodiments, the metal or ceramic composite is at a level at least about 10 wt % of the composite material. In other embodiments, the metal or ceramic composite is at a level at least about 20 wt %, or about 30 wt %, or about 40 wt %, or about 50 wt % of the composite material. In some embodiments, the metal or ceramic composite is at a level between about 0.1-5 wt % of the composite material. In other embodiments, the metal or ceramic composite is at a level between about 5-10 wt %, or between about 10-20 wt %, or between about 20-30 wt %, or between about 30-40 wt %, or between about 40-50 wt %, or between about 50-60 wt % of the composite material.

In some embodiments, when R is C, M is selected from a group consisting of Al, B, Ca, Cr, Hf, Mo, Nb, Si, Ta, Ti, V, W, Y, and Zr. In some embodiments, when R is N, M is selected from a group consisting of Al, B, Ba, Bi, Ca, Cr, Cu, Eu, Fe, Ga, Gd, La, Li, Mg, Mn, Nb, Nd, Pr, Si, Sr, Ta, Ti, V, Zn or Zr. In some embodiments, when R is S, M is selected from a group consisting of Ag, Al, As, Au, Ba, Bi, Cd, Ce, Co, Cu, Fe, Ga, Ge, Hg, In, Li, Mn, Mo, Na, Ni, P, Pb, Pd, Sb, Se, Sn, Sr, Ti, Tl, W, Yb, and Zn.

In some embodiments, the present invention features a composite material comprising a sulfur at a level at least about 50 wt % of the composite material, and a metal sulfur composite having a formula $P_xS_yM_z$ and at a level between about 0.1 and about 50 wt % of the composite material. In some embodiments, P is selected from a group consisting of Li and Na. In some embodiments, M is selected from a group consisting of Ag, Al, As Au, B, Ba, Bi, Ca, Cd, Ce, Co, Cr, Cu, Eu, Fe, Ga, Gd, Ge, Hf, Hg, In, La, Li, Mg, Mn, Mo, Na, Nb, Nd, Ni, P, Pb, Pd, Pr, Sb, Se, Si, Sn, Sr, Ta, Ti, Tl, V, W, Y, Yb, Zn and Zr. In some embodiments, x ranges between about 1 and about 10. In some embodiments, y ranges between about 1 and about 10. In some embodiments, z ranges between about 1 and about 30. In some embodiments, the metal sulfur composite is a uniform single phase. In some embodiments, the metal sulfur composite is dispersed in the sulfur.

In some embodiments, the sulfur is at a level at least about 40 wt %, or about 50 wt %, or about 60 wt %, or about 70 wt %, or about 80 wt %, or about 90 wt % of the composite material. In some embodiments, the sulfur is at a level between about 30-40 wt %, or about 40-50 wt %, or about 50-60 wt %, or about 60-70 wt %, or about 70-80 wt %, or about 80-90 wt % of the composite material.

In some embodiments, the metal sulfur composite is at a level at least about 10 wt % of the composite material. In other embodiments, the metal sulfur composite is at a level at least about 20 wt %, or about 30 wt %, or about 40 wt %, or about 50 wt % of the composite material. In some embodiments, the metal sulfur composite is at a level between about 0.1-5 wt %, or about 5-10 wt %, or about 10-20 wt %, or about 20-30 wt %, or about 30-40 wt %, or about 40-50 wt %, or about 50-60 wt % of the composite material.

In some embodiments, the composite material is copolymerized with a sulfur copolymer. In some embodiments, the sulfur copolymer comprises one or more sulfur monomers, at a level in the range of at least about 40 wt %, or at least about 50 wt %, or at least about 60 wt %, or at least about 70 wt %, or at least about 80 wt %, or at least about 90 wt % of the sulfur copolymer, and one or more comonomers each selected from a group consisting of amine monomers, thiol monomers, sulfide monomers, alkynylly unsaturated monomers, nitrone monomers, aldehyde monomers, ketone monomers, epoxide monomers, thiirane monomers, and ethylenically unsaturated monomers at a level in the range of about 0.1 wt % to 5 wt %, or about 5 wt % to 15 wt %, or about 15 wt % to 25 wt %, or about 25 wt % to 35 wt %, or about 35 wt % to 45 wt %, or about 45 wt % to 55 wt % of the sulfur copolymer. In some embodiments, the polymeric material further comprises one or more epoxide monomers at a level in the range of about 5 wt % to 15 wt %, or about 15 wt % to 25 wt %, or about 25 wt % to 35 wt %, or about 35 wt % to 45 wt %, or about 45 wt % to 55 wt %, or about 55 wt % to 65 wt %, or about 65 wt % to 75 wt %, or about 75 wt % to 85 wt %, or about 85 wt % to 95 wt % of the polymeric material, wherein at least one epoxy functional group of the epoxide monomers is bonded to a functional group of the sulfur copolymer.

In some embodiments, the composite material is copolymerized with a polymeric material comprising a sulfur copolymer and one or more epoxide monomers at a level in the range of about 5 wt % to about 95 wt % of the polymeric material. In some embodiments, the sulfur copolymer comprises one or more sulfur monomers, at a level in the range of at least about 50 wt % of the sulfur copolymer, and one or more comonomers each selected from a group consisting of amine monomers, thiol monomers, sulfide monomers, alkynylly unsaturated monomers, nitrone monomers, aldehyde monomers, ketone monomers, epoxide monomers, thiirane monomers, and ethylenically unsaturated monomers at a level in the range of about 0.1 wt % to about 50 wt % of the sulfur copolymer. In some embodiments, at least one epoxy functional group of the epoxide monomers is bonded to a functional group of the sulfur copolymer.

In some embodiments, the composite material is self-healing. In some embodiments, when one or more S—S bonds of the sulfur copolymer are broken, the S—S bonds are reconnected by thermal reforming.

In some embodiments, the present invention features a method of producing a sulfur copolymer, said method comprising providing elemental sulfur, heating the elemental sulfur into a molten sulfur, and adding one or more comonomers to the molten sulfur, thereby forming the sulfur copolymer. In some embodiments, the elemental sulfur is heated to a temperature of about 120 to 230° C. In some embodiments, the one or more comonomers are selected from a group consisting of amine monomers, thiol monomers, sulfide monomers, alkynylly unsaturated monomers, nitrone monomers, aldehyde monomers, ketone monomers, epoxide monomers, thiirane monomers, and ethylenically unsaturated monomers. In some embodiments, the elemental sulfur is at a level of at least about 50 wt % of the sulfur copolymer. In some embodiments, the one or more comonomers are at a level of about 1 to 50 wt % of the sulfur copolymer.

In some embodiments, the present invention features a method of producing a copolymer material, said method comprising providing a sulfur copolymer, mixing the sulfur copolymer with one or more epoxide monomers, melting the sulfur copolymer and epoxide mixture, mixing the melted sulfur copolymer and epoxide mixture, and adding an alcohol to the to the melted sulfur copolymer and epoxide mixture, thereby forming the copolymer material. In some embodiments, the method of providing a sulfur copolymer comprises providing elemental sulfur, heating the elemental sulfur into a molten sulfur, and adding one or more comonomers to the molten sulfur, thereby forming the sulfur copolymer.

In some embodiments, the elemental sulfur is heated to a temperature of about 120 to 230° C. In some embodiments, the sulfur copolymer and epoxide mixture is heated to a temperature of about 60 to 80° C. In some embodiments, the one or more comonomers are selected from a group consisting of amine monomers, thiol monomers, sulfide monomers, alkynylly unsaturated monomers, nitrone monomers, aldehyde monomers, ketone monomers, epoxide monomers, thiirane monomers, and ethylenically unsaturated monomers. In some embodiments, the sulfur copolymer is at a level in the range of about 5 wt % to about 95 wt % of the copolymer material. In some embodiments, the elemental sulfur is at a level of at least about 50 wt % of the sulfur copolymer. In some embodiments, the one or more comonomers are at a level of about 1 to 50 wt % of the sulfur copolymer. In some embodiments, the one or more epoxide monomers are at a level in the range of about 5 wt % to about 95 wt % of the copolymer material.

In some embodiments, the present invention features a method of producing a composite material, said method comprising providing elemental sulfur, mixing a metal or ceramic composite with the elemental sulfur to form a mixture, and heating the mixture until vitrification, thereby forming the composite material. In some embodiments, the mixture is heated to a temperature of about 160 to 200° C. In some embodiments, the elemental sulfur is at a level of at least about 50 wt % of the composite material. In some embodiments, the metal or ceramic composite is at a level of about 1 to 50 wt % of the composite material.

In some embodiments, the metal or ceramic composite has a formula $M_xR_y$. In some embodiments, M is selected from a group consisting of Ag, Al, As Au, B, Ba, Bi, Ca, Cd, Ce, Co, Cr, Cu, Eu, Fe, Ga, Gd, Ge, Hf, Hg, In, La, Li, Mg, Mn, Mo, Na, Nb, Nd, Ni, P, Pb, Pd, Pr, Sb, Se, Si, Sn, Sr, Ta, Ti, Tl, V, W, Y, Yb, Zn and Zr. In some embodiments, R is selected from a group consisting of C, N, and S. In some embodiments, x ranges between about 1 and about 30. In some embodiments, y ranges between about 1 and about 10.

In some embodiments, the present invention features a sulfur epoxy resin comprising at least one branched or cross-linked sulfur chain, wherein at least one branch or cross-link of the sulfur chain comprises an ether bond, wherein the sulfur content ranges from about 5-15 wt %, or from about 15-25 wt %, or from about 25-35 wt %, or from about 35-45 wt %, or from about 45-55 wt %, or from about 55-65 wt %, or from about 65-75 wt %, or from about 75-85 wt %, or from about 85-95 wt %, or from about 5-95 wt % of the epoxy resin.

In some embodiments, the present invention features a sulfur epoxy resin comprising a portion comprising —$R_1$—S—$(S)_n$—S—$R_2$—, wherein n ranges from 0 to 6; and at least one cross-link of the epoxy resin comprising an ether bond, wherein the sulfur content ranges from about 5-15 wt %, or from about 15-25 wt %, or from about 25-35 wt %, or from about 35-45 wt %, or from about 45-55 wt %, or from about 55-65 wt %, or from about 65-75 wt %, or from about 75-85 wt %, or from about 85-95 wt %, or from about 5-95 wt % of the epoxy resin.

In some embodiments, R, may be any of the aforementioned amine monomers, thiol monomers, sulfide monomers, alkynylly unsaturated monomers, nitrone monomers, aldehyde monomers, ketone monomers, epoxide monomers, thiirane monomers, and ethylenically unsaturated monomers bonded to the S moiety by the monomer's appropriate reactive functional group. In some embodiments, $R_2$ may be any of the aforementioned amine monomers, thiol monomers, sulfide monomers, alkynylly unsaturated monomers, nitrone monomers, aldehyde monomers, ketone monomers, epoxide monomers, thiirane monomers, and ethylenically unsaturated monomers bonded to the S moiety via the monomer's appropriate reactive functional group.

In some embodiments, the sulfur chain comprises at least one branch or cross-link arm. In some embodiments, the branch or cross-link arm may be any of the aforementioned amine monomers, thiol monomers, sulfide monomers, alkynylly unsaturated monomers, nitrone monomers, aldehyde monomers, ketone monomers, epoxide monomers, thiirane monomers, and ethylenically unsaturated monomers bonded to the S moiety of the sulfur chain via the monomer's appropriate reactive functional group.

In some embodiments, the present invention features a sulfur composite material comprising a plurality of metal or ceramic composite particles having a formula $M_xR_y$ dispersed in a polymeric sulfur, wherein a sulfur content of the sulfur composite material is at least 50 wt %.

In some embodiments, the present invention features a sulfur composite material comprising a plurality of metal or ceramic composite particles having a formula $P_xM_yR_z$ dispersed in a polymeric sulfur, wherein a sulfur content of the sulfur composite material is at least 50 wt %.

In some embodiments, the present invention features a copolymer material comprising one or more sulfur monomers at a level in the range of about 5 wt % to about 95 wt % of the copolymer material, one or more comonomers each selected from a group consisting of amine monomers, thiol monomers, sulfide monomers, alkynylly unsaturated monomers, nitrone monomers, aldehyde monomers, ketone monomers, thiirane monomers, and ethylenically unsaturated monomers at a level in the range of about 5 wt % to about 50 wt % of the copolymer material, and one or more epoxide monomers at a level in the range of about 5 wt % to about 95 wt % of the copolymer material. In some embodiments, at least one epoxy functional group of the epoxide monomers is bonded to a functional group of the comonomer, a sulfur moiety of the sulfur monomer, or a combination thereof.

High Refractive Index Polymers for IR Optical Materials

Figure 33:
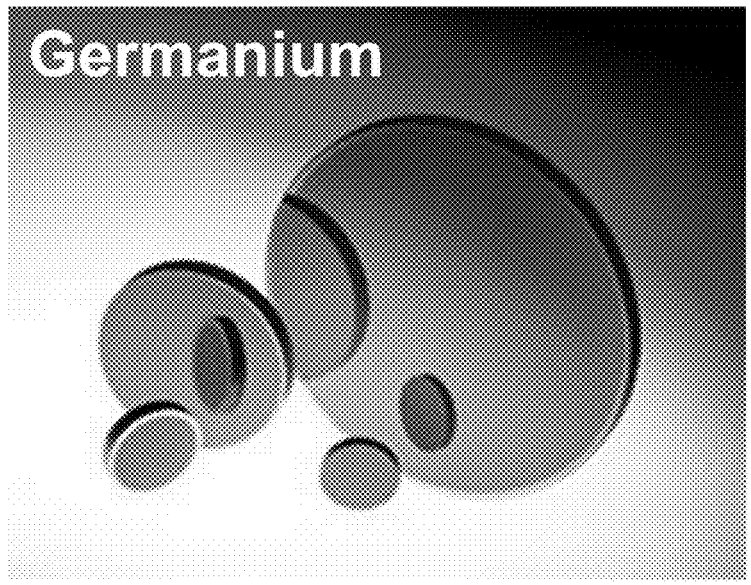
FIG. 33 shows typical materials for infrared thermal imaging lens.
Figure 33:
Figure 34:
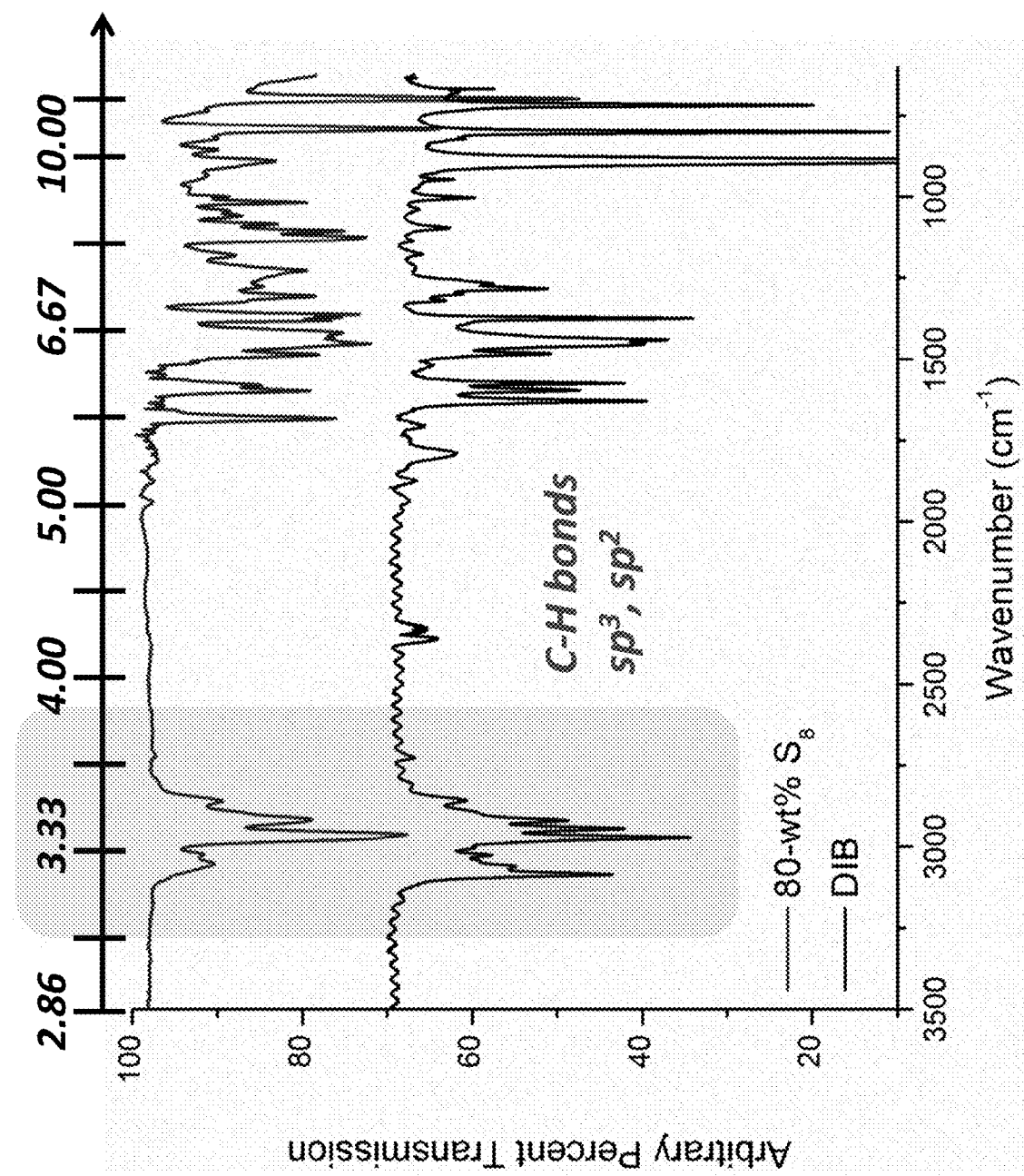
FIG. 34 shows a non-limiting example of infrared lens constructed from a sulfur copolymer of the present invention

As shown in FIGS. 33 and 34, the development of polymeric materials for infrared (IR) optical applications has not been achieved due to challenges in designing systems with sufficiently high refractive index (n) and transparency in the IR spectral regime. IR optical technology has numerous potential applications in the civil, medical, and military areas, where inorganic semiconductors (e.g., Ge, Si) and chalcogenide glasses have been widely used as materials for device components due to their high refractive index (n~2.0-4.0) and low losses from 1-10 μm. Other examples of glass materials currently in use are InSb, InGaAs, HgCdTe, ArSe, and ArS. While such materials are well suited for these applications, they are inherently more expensive, toxic, and difficult to process in comparison to organic polymeric materials.

Figure 35:
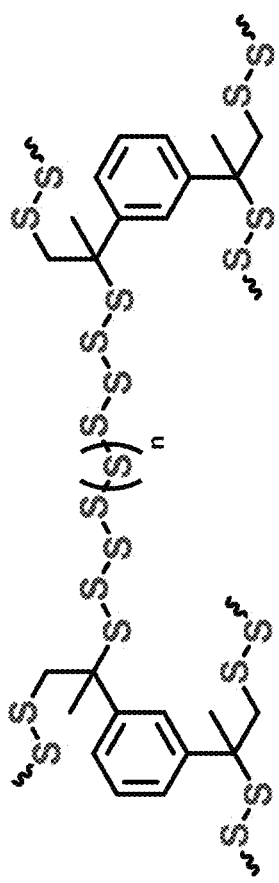
FIG. 35 shows a graph of transparency for 80%-wt $S_8$ and DIB.
Figure 35:
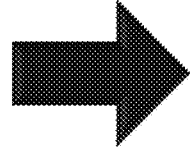
Figure 35:
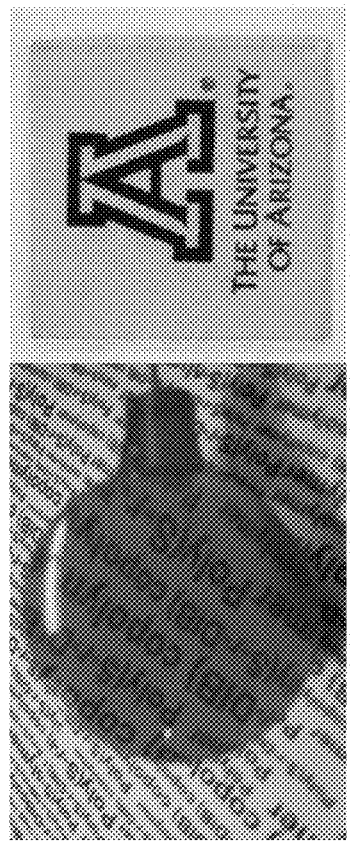

As shown in FIG. 35, the sulfur copolymers that have been described herein are the first class of polymeric materials that exhibit high transparency in the short-wave and mid-IR regimes due to the presence of largely IR inactive S—S bonds. Furthermore, since these sulfur copolymers are readily melt, or solution processed, fabrication of free standing films, windows, or lenses can be easily conducted. Access to these kinds of high quality and inexpensive lenses are anticipated to open new opportunities in low cost IR optical devices and technologies including IR thermal imaging rifle scopes and home monitoring.

Figure 36A:
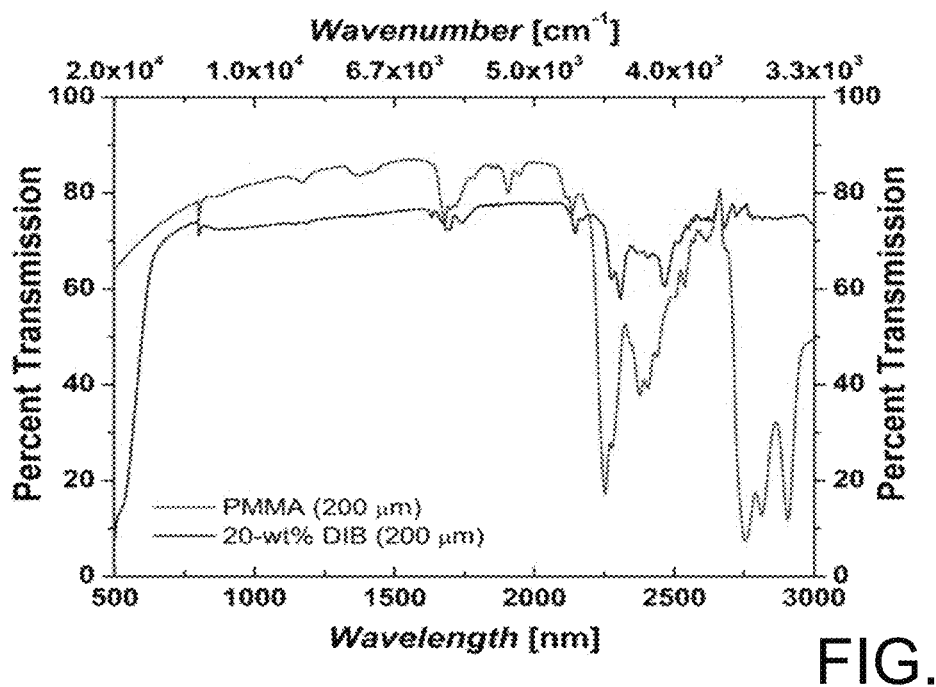
FIG. 36a shows a graph of transparency for a sulfur copolymer and PMMA.
Figure 36B:
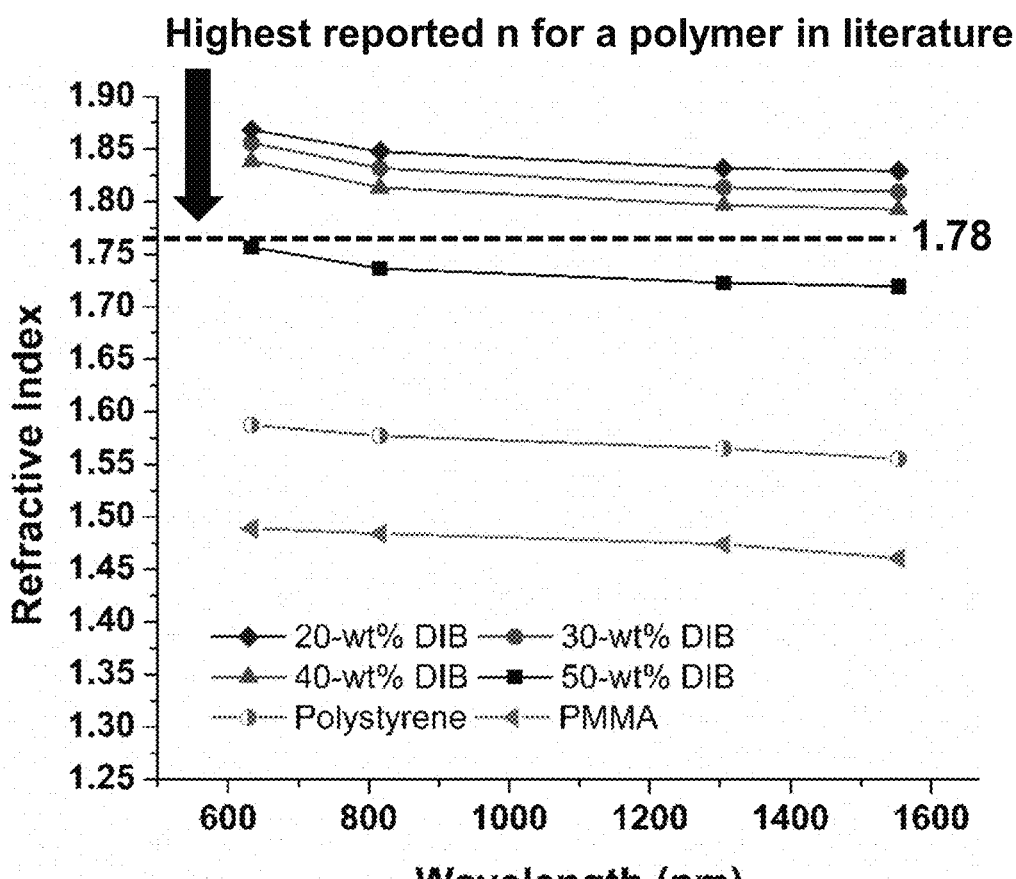
FIG. 36b shows a graph of refractive indexes for various polymers and sulfur copolymers.
Figure 37:
FIG. 37 shows mid-IR imaging with a sulfur copolymer lens.
Figure 38:
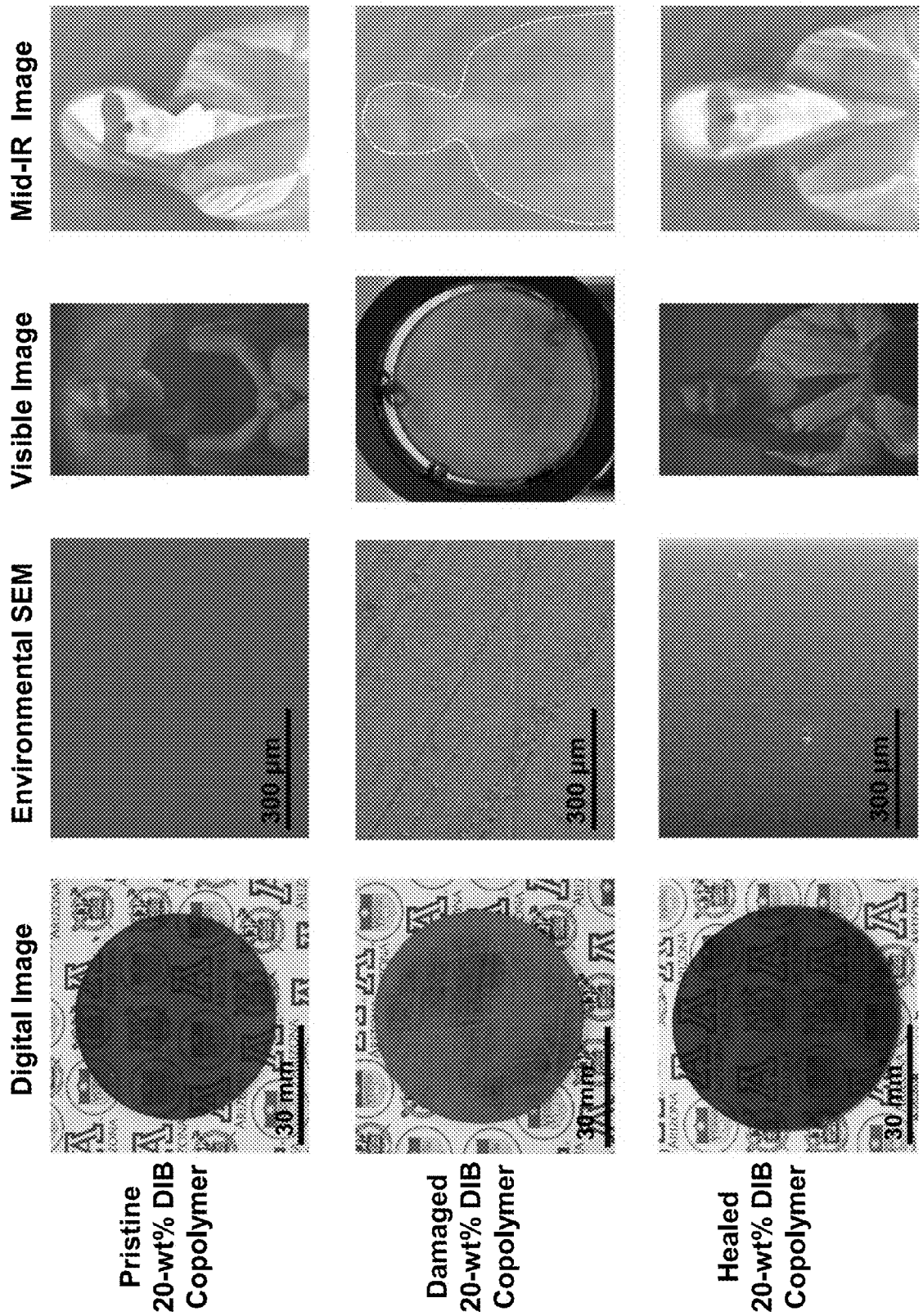
FIG. 38 shows comparisons of pristine, damaged, and self-healed sulfur copolymer lenses for visible and mid-IR imaging.

As shown in FIGS. 36a,b, the refractive index of poly(S-r-DIB) film is >22% higher than PMMA, and the transparency of poly(S-r-DIB) film is 6× higher at 2900 nm. As shown in FIGS. 36-38, sulfur-rich copolymers were synthesized via inverse vulcanization to create novel copolymers with high refractive indices and optical transparency in the near to mid-infrared (1.5 μm and 3-5 μm) regions. By directly varying the feed ratio of comonomers during inverse vulcanization, the content of S—S bonds in these materials was controlled, thereby enabling correlation of optical properties with copolymer composition. All copolymer compositions possess a refractive index above n=1.7 at 1550 nm. Furthermore, these sulfur copolymers were readily solution, or melt processed into thin films, or free standing lenses for IR imaging.

In other embodiments, an optical element comprising the polymeric composition is formed as a substantially optically transparent body having an optical transparency in the visible and infrared spectrum. The polymeric composition has a refractive index in the range of about 1.7 to about 2.2 and at least one wavelength in the range of about 300 nm to about 10 μm.

Electrochemical Cells

The use of a new electroactive cathode material for an Li—S battery, which can be a sulfur based material, or polymer that, upon discharge, generates soluble additive species in situ that co-deposit onto the cathode with lower sulfide discharge products. These additive species may be introduced into the electroactive material during the synthesis of the material, or added to the electrolyte or battery separator as a soluble species. These additive species are able to co-deposit with sulfide-containing discharge products via active electrochemical reactions, or passive non-electrochemical processes. Co-deposition of these additive species with sulfide discharge products onto the Li—S cathode plasticizes the electrode against mechanical fracture during battery charge-discharge cycling. Plasticization enables retention of charge capacity and improve cycle lifetime beyond 100 cycles.

The electroactive material in this case is best embodied by a copolymer material comprising elemental sulfur and an organic comonomer. Upon discharge of this copolymer, soluble organosulfur species are formed which function to improve Li—S batteries as described above.

In some embodiments, the present invention features an electrochemical cell comprising an anode comprising metallic lithium, a cathode comprising the composite material of any of the aforementioned embodiments, and a non-aqueous electrolyte disposed between the cathode and the anode. In some embodiments, the electrochemical cell has a capacity of between about 200 and about 1,400 mAh/g. The cathode may be flexible. The electrochemical cell may have a capacity in the range of about 200 to about 1400 mAh/g. In another embodiment, the electrochemical cell may have a capacity in the range of about 600 to about 1000 mAh/g.

In another embodiment, an electrochemical cell comprises an anode comprising metallic lithium, a cathode comprising a sulfur containing polymer which generates soluble additive species in situ upon discharge and the soluble additive species co-deposit with lower sulfide discharge products onto the cathode, and a non-aqueous electrolyte interposed between the cathode and the anode. In some embodiments, the lower sulfide discharge products are $Li_2S_3$, $Li_2S_2$, or $Li_2S$.

In some embodiments, the electrolyte and/or a separator comprises a sulfur containing polymer according to any of the aforementioned polymeric compositions. The copolymer generates soluble organosulfur species upon discharge. The soluble additive species are co-deposited with the lower sulfide discharge products by an electrochemical reaction or a non-electrochemical reaction.

Any embodiment of the electrochemical cells may be used in electric vehicle applications, portable consumer devices portable consumer devices (e.g., Personal electronics, cameras, electronic cigarettes, handheld game consoles, and flashlights), motorized wheelchairs, golf carts, electric bicycles, electric forklifts, tools, automobile starters, and uninterruptible power supplies.

EXAMPLES

Example 7

Figure 5:
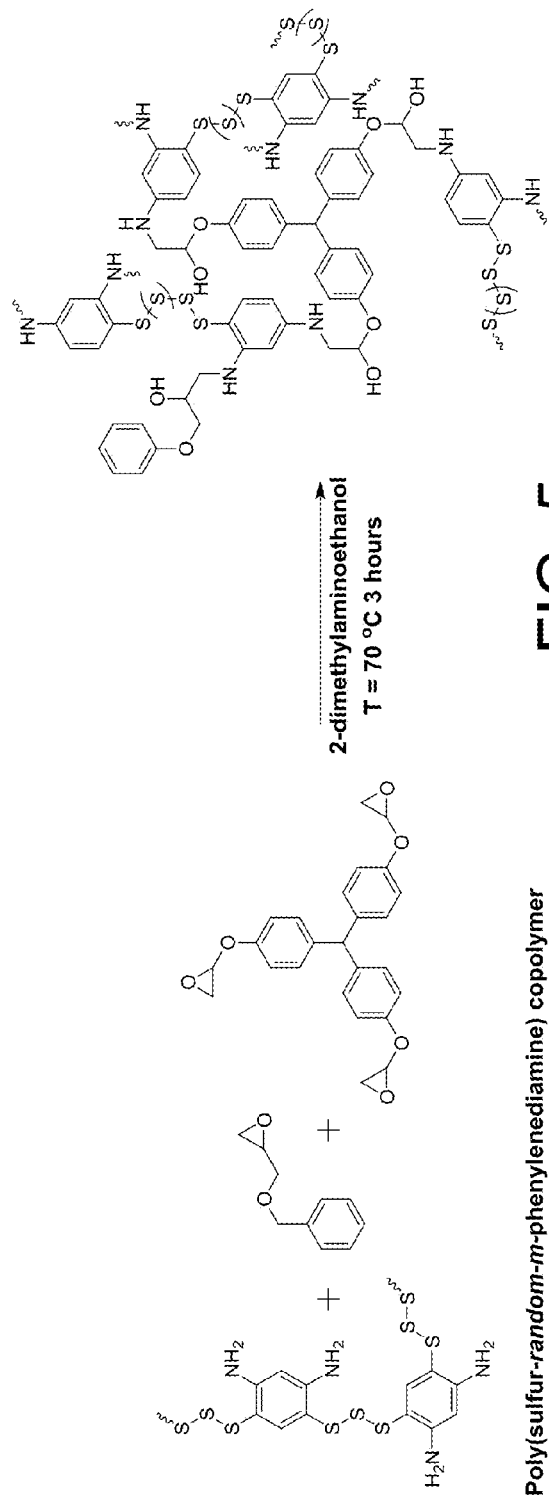
FIG. 5 shows a reaction schematic of a sulfur copolymer and epoxide polymerization.
Figure 6:
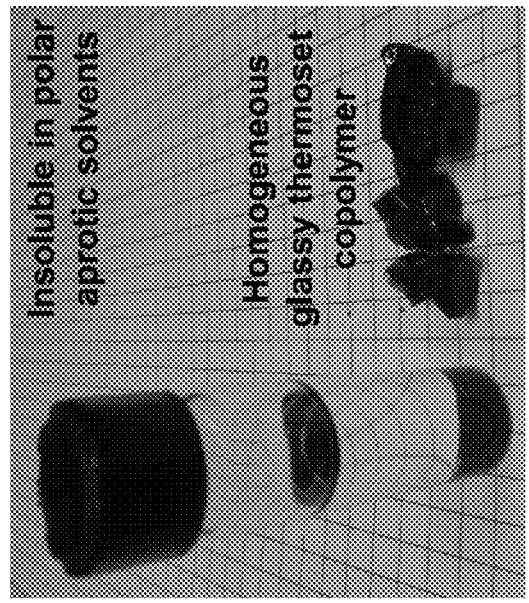
FIG. 6 shows a non-limiting sample of a sulfur copolymer and epoxide thermoset.
Figure 7:
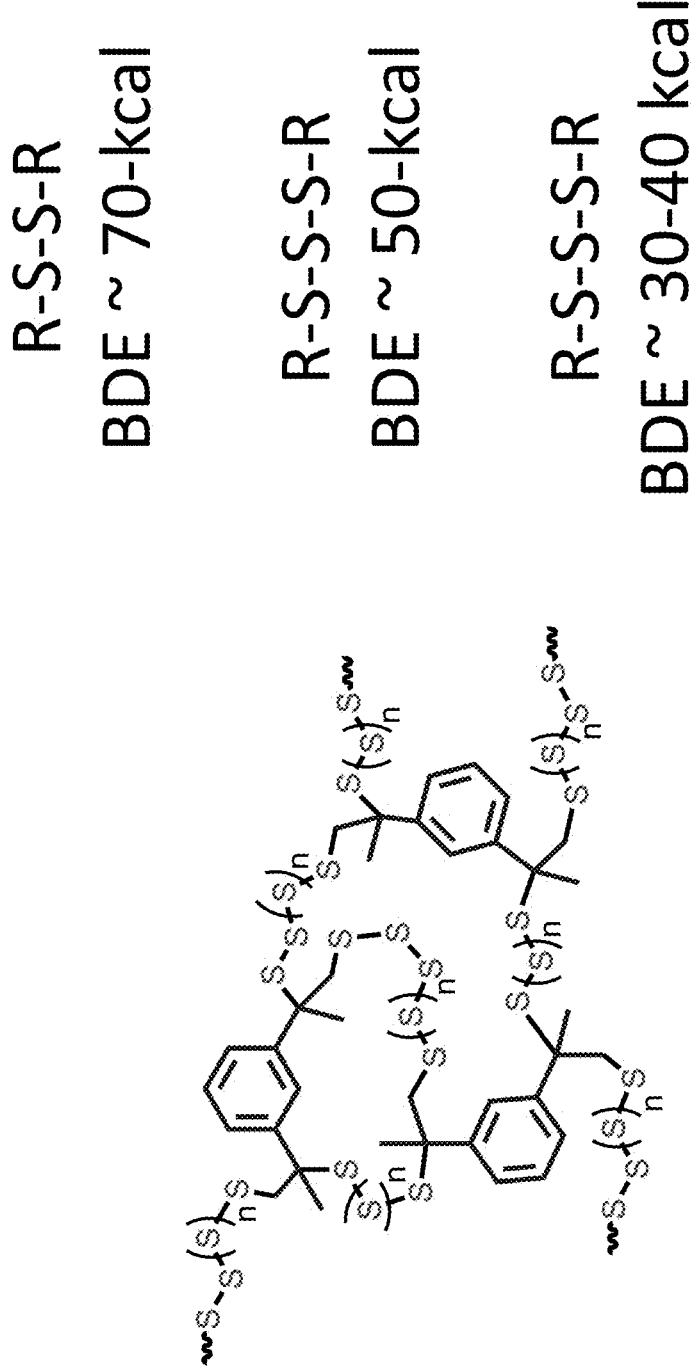
FIG. 7 shows non-limiting examples of S—S chains and bond dissociation energies (BDE) of the S—S chains.
Figure 8:
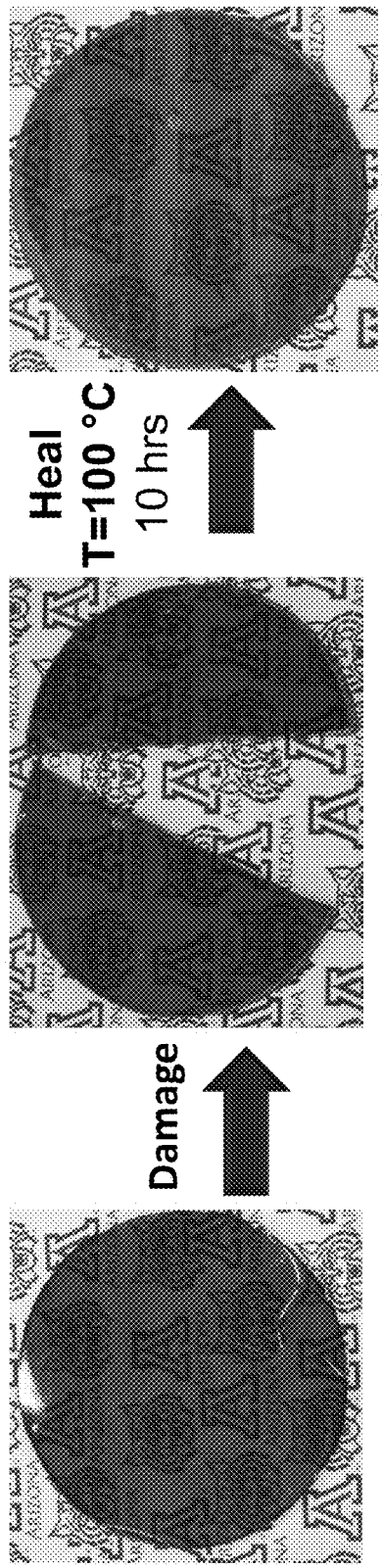
FIG. 8 shows a self-healing sulfur copolymer sample.
Figure 10:
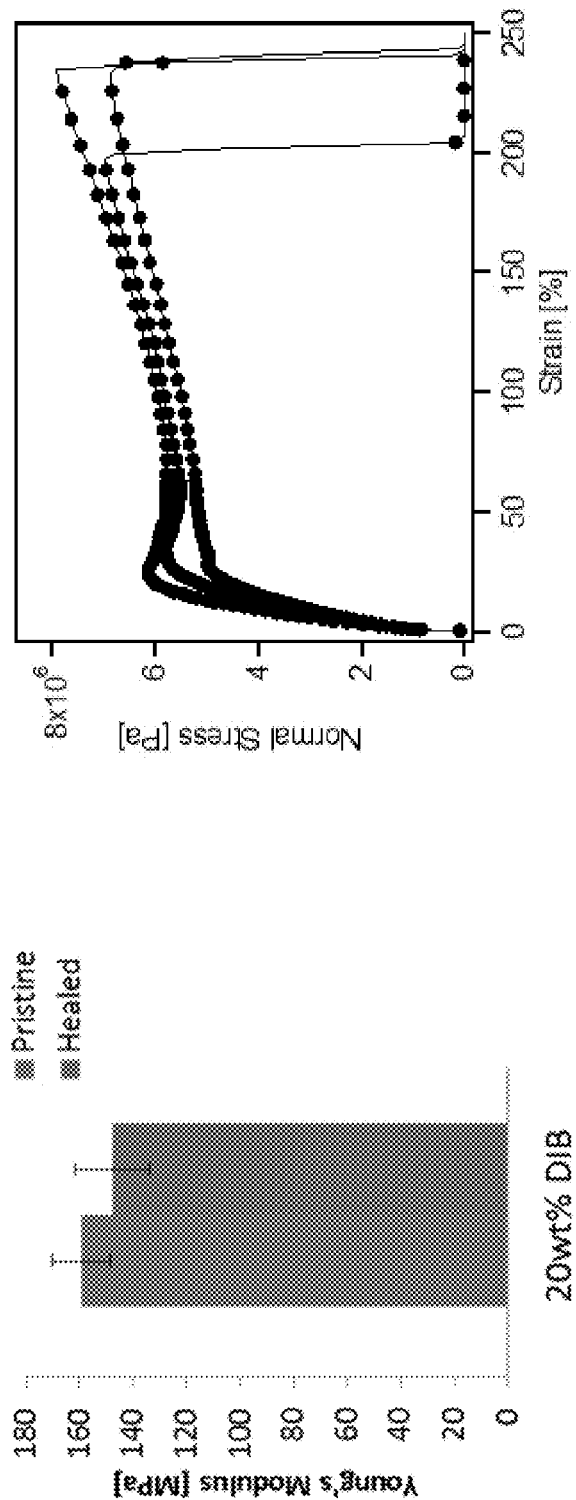
FIG. 10 shows a non-limiting example of a stress-strain curve for sulfur copolymers.
Figure 9:
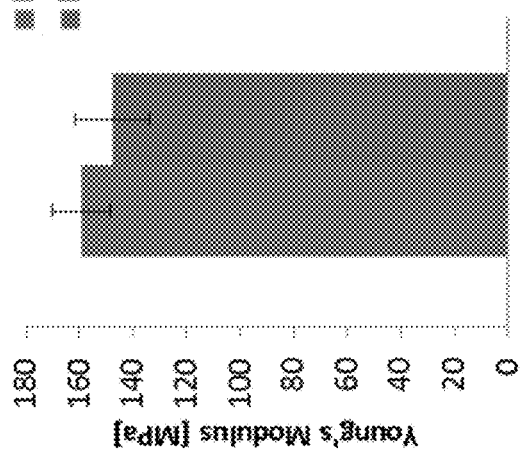
FIG. 9 shows a non-limiting example of Young's Modulus for a pristine and a self-healed sulfur copolymers having 20 wt % diisopropenylbenzene (DIB).

Referring now to FIG. 5, The following is a non-limiting example of a procedure for the preparation of sulfur epoxy materials:

1. To an 11 mL glass scintillation vial equipped with a ½ inch magnetic stir bar were added the poly(sulfur-random-m-phenylenediamine) copolymer (about 50-wt % $S_8$) (about 0.5 g), benzyl glycidyl ether (about 0.634 mL, about 0.683 g, about 4.162 mmol), and the solid tris(4-hydroxyphenyl) methane triglycidyl ether (about 1.916 g, about 4.162 mmol).

2. The vial was capped and placed in a thermostat controlled oven held at about T=65° C. for about 30 minutes to allow the melting of the tris(4-hydroxyphenyl) methane triglycidyl ether and the dissolution of a large portion of the copolymer before magnetically mixing.

3. After about 30 minutes, the vial is placed in a thermostat controlled oil bath held at about T=70° C. The mixture was stirred to homogenize prior to the injection of the 2-dimethylaminoethanol (about 0.025 mL, about 0.0222 g, about 0.08445 mmol).

4. The reaction was stirred and allowed to cure for about 3 hours before cooling and removing from the vial (yield: about 98.0%)

Example 8

Figure 11:
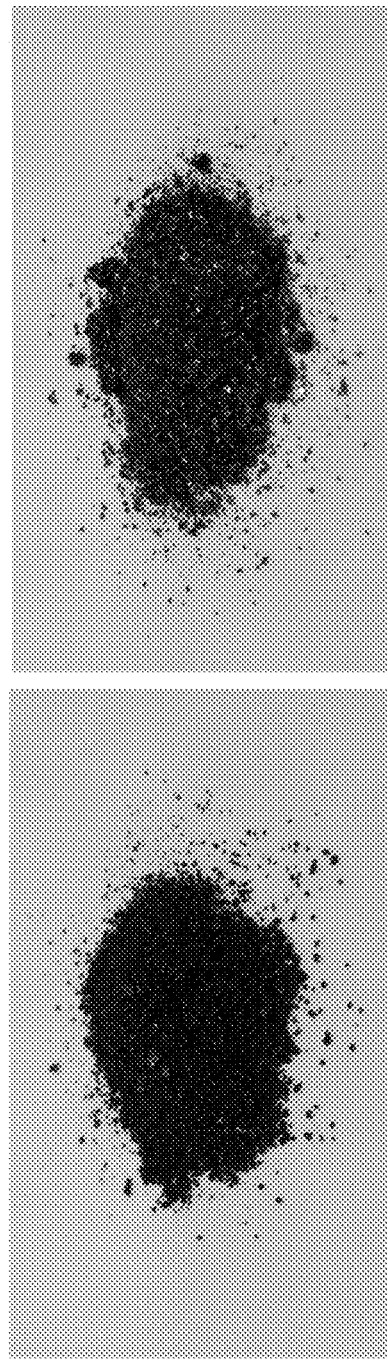
FIG. 11 shows non-limiting examples of sulfur/metal composite materials.
Figure 12:
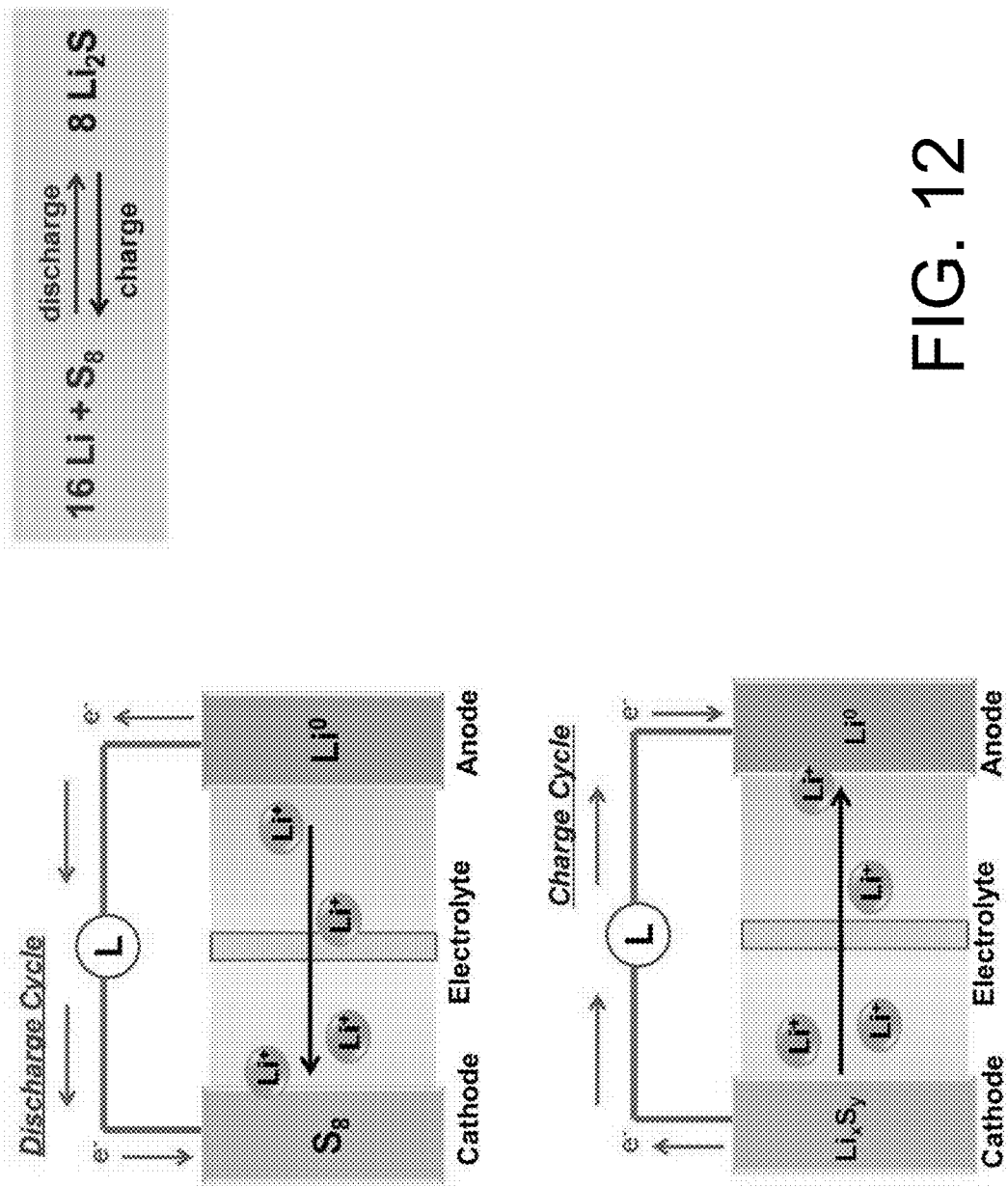
FIG. 12 shows a schematic view of charge and discharge cycles of an electrochemical cell.
Figure 13:
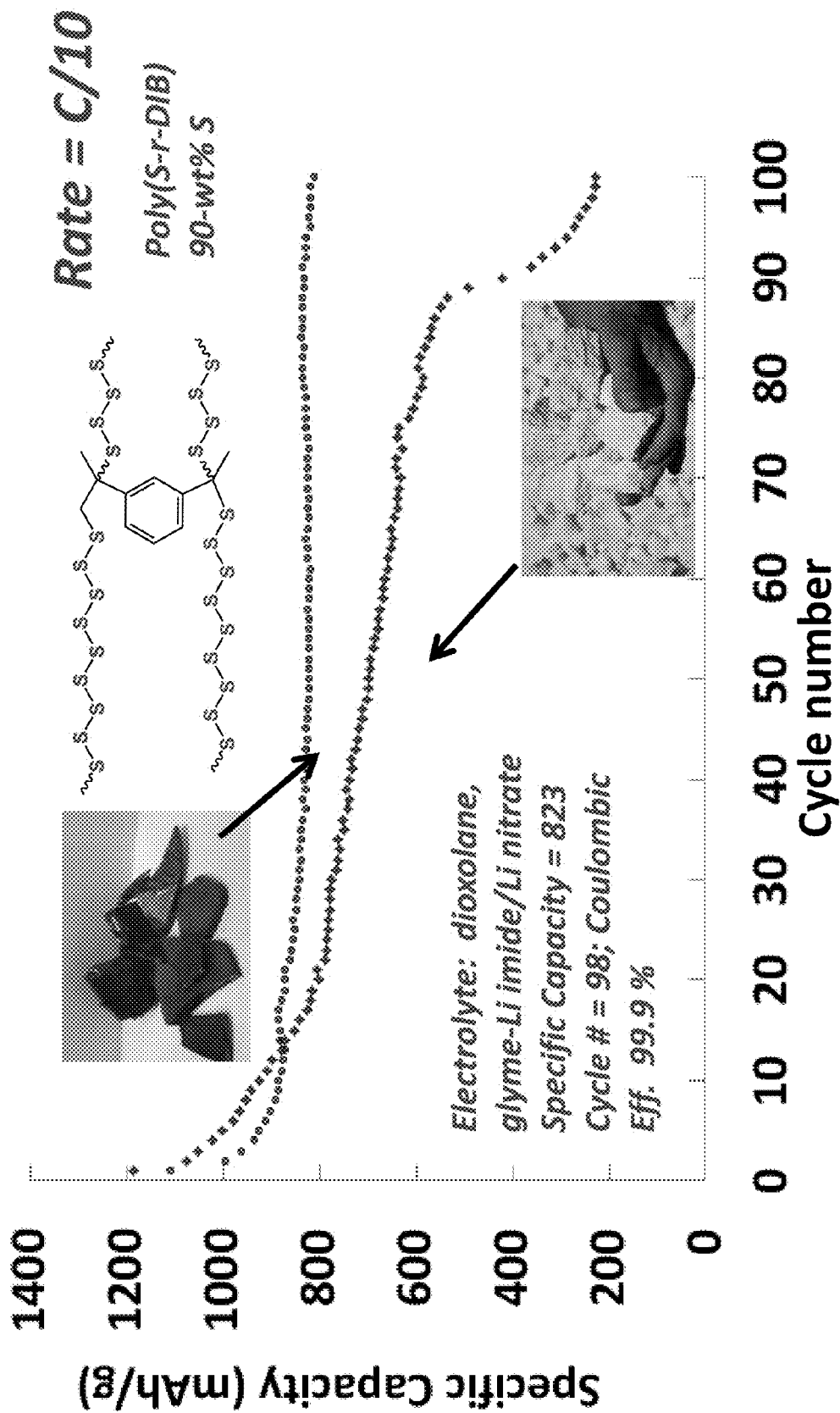
FIG. 13 shows data from a cycling experiment (C/10) comparing sulfur copolymers and elemental sulfur as cathodes for electrochemical cells.
Figure 14:
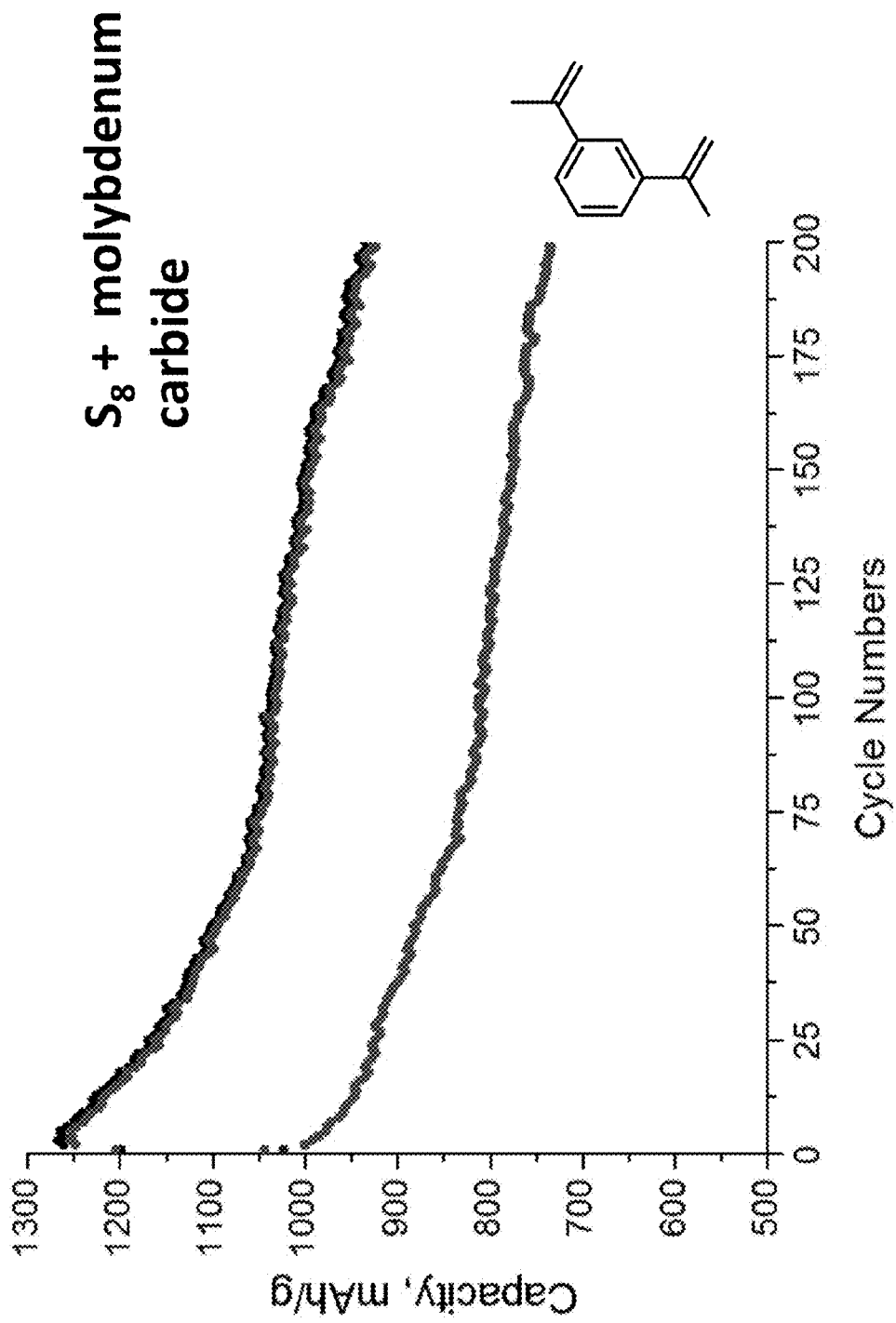
FIG. 14 shows data from a cycling experiment (C/5) comparing sulfur copolymers and sulfur composite materials as cathodes for electrochemical cells.
Figure 15:
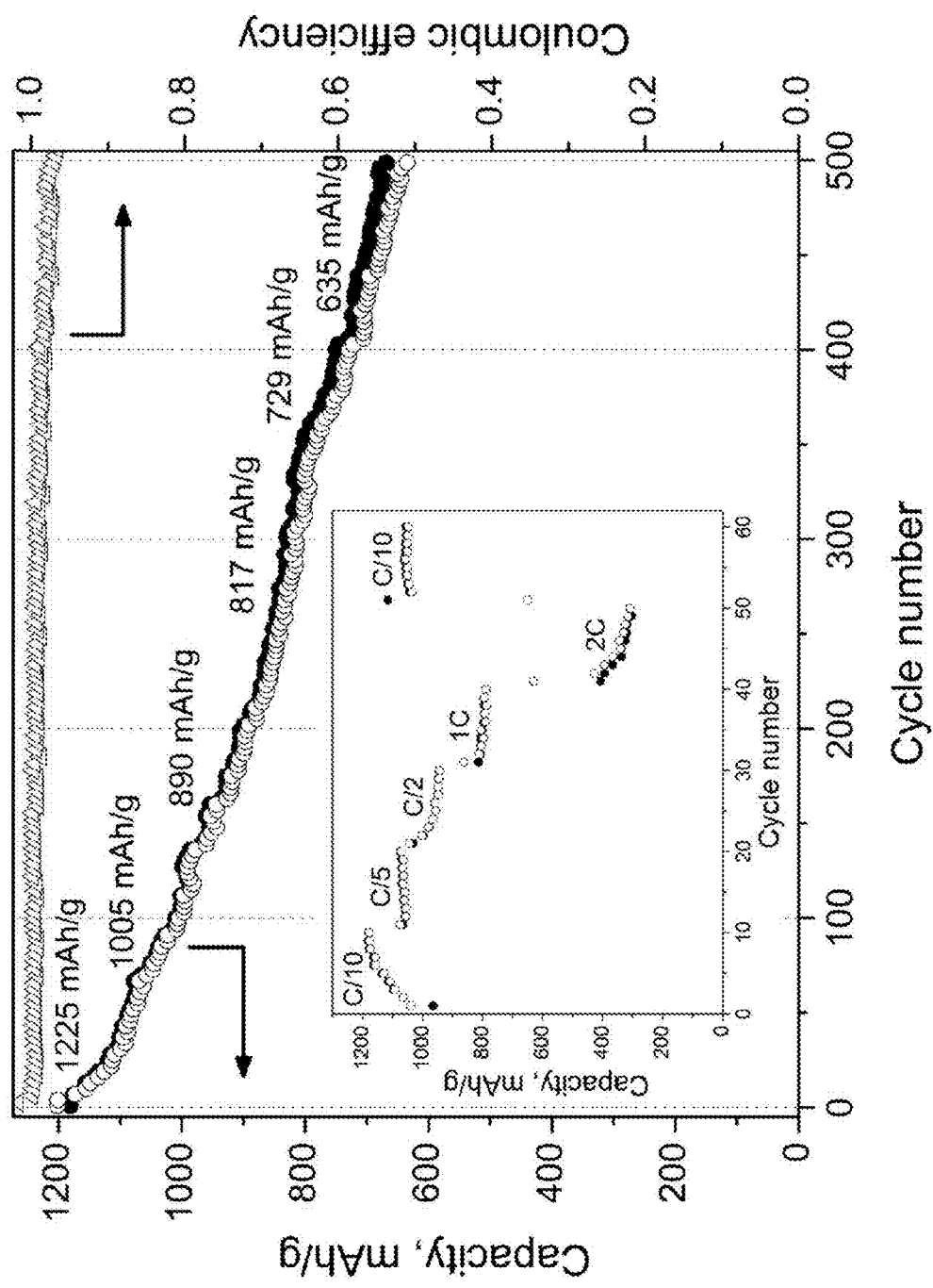
FIG. 15 shows data from a long-term cycling experiment for various C-rates of Li—S batteries utilizing sulfur copolymers.
Figure 16A:
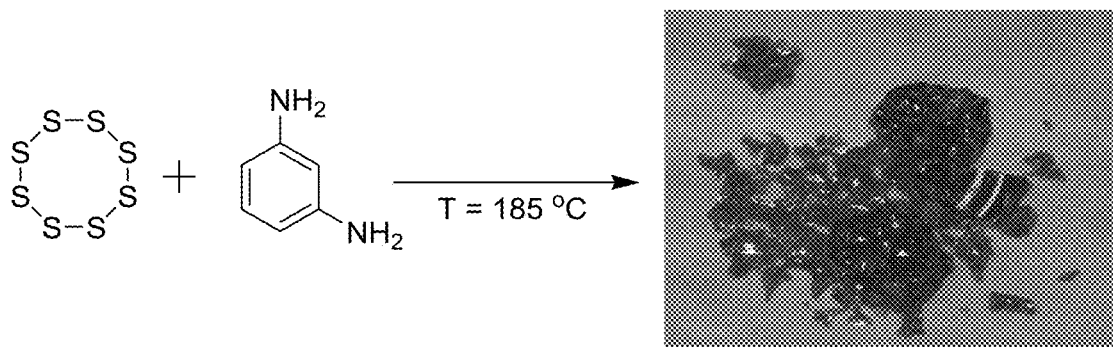
FIG. 16a-16d shows various copolymers made from $S_8$ and 1,3-phenylenediamine
Figure 16B:
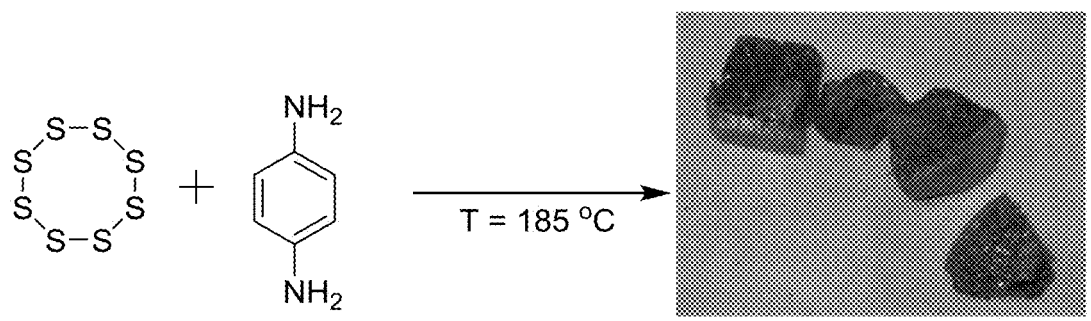
Figure 16C:
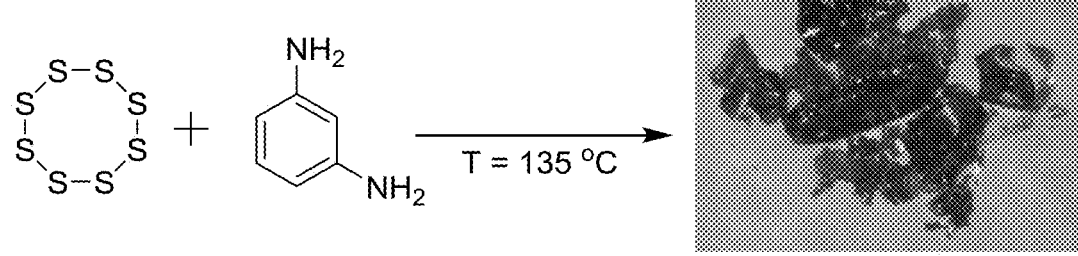
Figure 16D:
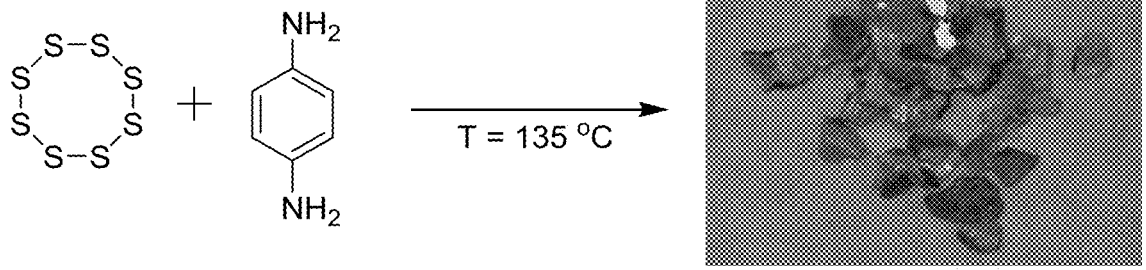

Referring now to FIG. 11, the following is a non-limiting example of a procedure for the preparation of a sulfur/metal sulfide composite material:

1. To 5 mL vial equipped with a magnetic stir bar was added sulfur (about 1.00 g, about 3.87 mmol as $S_8$) and molybdenum sulfide (about 1.00 g, about 6.25 mmol as $Mo_2S$).

2. The mixture was heated at about 180° C. while stirring until vitrification.

3. The vitreous product was then cooled in a dry ice/acetone bath for about 2 min and the product was recovered by breaking the vial yielding an opaque grey-black solid in quantitative yield.

Example 9

The following is a non-limiting example of a thermal reforming procedure of a self-healing polymer substrate:
1. The polymeric substrate having a crack is placed in an oven.
2. The polymeric substrate is heated at a temperature of about 100° C. for about 3 hours.
3. The polymeric substrate is inspected to ensure that it is completely self-healed.

Photoactive Sulfur Polymers

Figure 18:
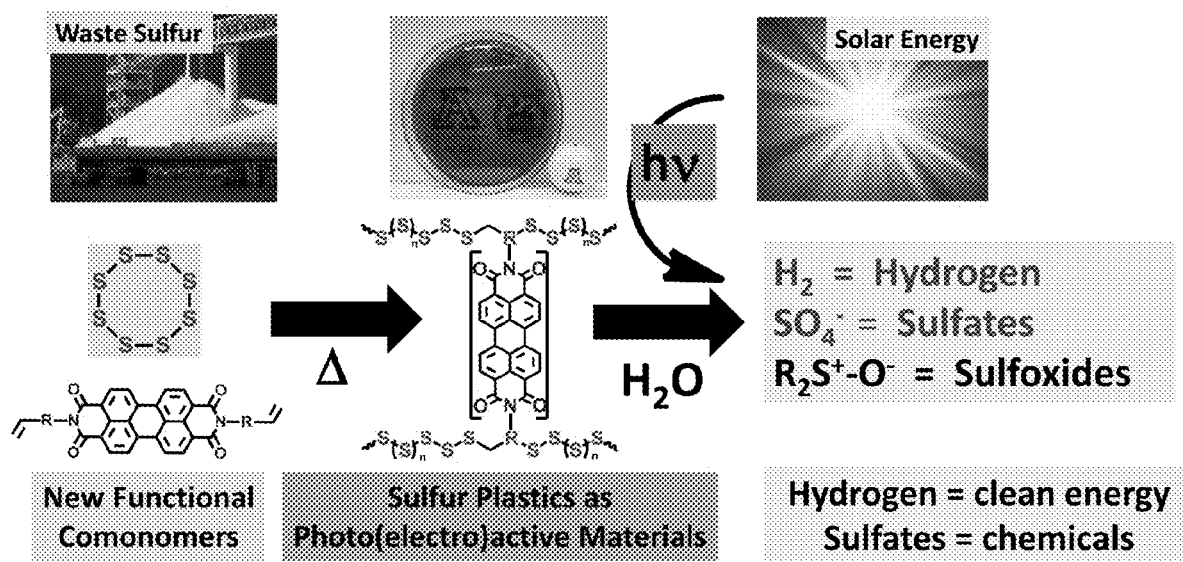
FIG. 18 shows photochemical processes to generate chemicals for energy and commodity chemicals.

Referring to FIG. 18, another aspect of the present invention relates to the use of sulfur to make a new class of photoactive sulfur polymers. The polymers can be used as a new solar fuel in which photochemical processes generate useful chemicals for clean energy and commodity chemicals. Without wishing to limit the present invention to a particular theory or mechanism, the chemical synthetic methodologies presented herein have the ability to change elemental sulfur into a polymeric material with photoactive properties that upon solar irradiation can photochemically react with water to generate molecular hydrogen ($H_2$), and oxidized sulfur species such as sulfates ($SO_4^{2-}$), sulfonates ($RSO_3^-$) and organosulfoxides ($R_2$—$S^+$—$O^-$). This new sulfur-based polymer would contain (either by copolymerization, blending, dispersion or other forms of mixing) a fraction of photoactive compounds that can absorb light and produce reactive intermediates. These reactive intermediates promote the photoelectrochemical degradation of the sulfur polymer in the presence of water into useful small molecules for clean energy (e.g. $H_2$) and commodity chemicals such as sulfonates and sulfates that are important for fertilizers, sulfate salts, detergents.

In certain embodiments, a photoactive monomer is based on styrenic perylene diimides using established synthetic methods, such as those described in Wurther, which is hereby incorporated herein by reference in its entirety. It has been determined that these types of perylene diimides exhibit excellent solubility in liquid sulfur, which is a desirable feature in the inverse vulcanization process. Accordingly, in certain embodiments, the synthesis of perylene-containing sulfur polymers can be achieved by simple dissolution of these photoactive monomers in liquid sulfur and heating the solution to T=185° C. For example, sulfur polymers with 1-5% of the photoactive perylene units can be made. The copolymers can include a variety of other additional monomers such as 1,3-diisopropylenebenzene (DIB). Non-limiting examples of other monomers are described in WO2013/023216 and U.S. Provisional Patent Application No. 61/940,102, which are incorporated herein by reference. A person of ordinary skill in the art can use such additional monomers, for example, to modulate the thermomechanical properties of the final sulfur polymer. Characterization of this copolymer can be performed using conventional spectroscopic and chromatographic methods such as NMR and SEC. To confirm photoactivity of the polymers, thin films can be cast onto transparent electrodes, such as ITO, to enable photoelectrochemical degradation of the thin film upon visible excitation and monitoring the evolution of $H_2$. The present invention thus, in certain aspects, allows for production of hydrogen for use as a fuel.

In some embodiments, a polymeric composition comprises a sulfur copolymer, the sulfur copolymer comprising one or more sulfur monomers, at a level in the range of at least about 50 wt % of the copolymer, and one or more photoactive monomers at a level in the range of about 0.1 wt % to about 50 wt % of the copolymer. Each photoactive monomer can have the structure:

The "A" may be a ring system. The "A" may also be a photoactive chromophore. In some embodiments, the "A" may be selected from a group consisting of perylenes, pyrenes, couramins, cyanine dyes, fluoresceins, and derivatives thereof, polythiophenes, polyanilines, $TiO_2$, CdSe, CdS, CdSe—CdS, natural and synthetic dyes, aromatics, heterocycles, conjugated organic polymers, inorganic chromophores, nanocomposite chromophores, organic chromophores, photoactive agents, and semiconductor nanoparticles. In some embodiments, the "B" comprises a polymerizable moiety, wherein the polymerizable moiety is selected from a group consisting of a carboxylate moiety, an ethylenically unsaturated moiety, an epoxide moiety, a thiirane moiety, an amine moiety, a thiol moiety, a sulfide moiety, an alkynylly unsaturated moiety, a nitrone moiety, an aldehyde moiety and a ketone moiety. In some embodiments, n is 1, 2, 3, 4, 5, 6, 7 or 8.

In some embodiments, the sulfur copolymer further comprises one or more monomers selected from a group consisting of ethylenically unsaturated monomers, epoxide monomers, thiirane monomers, amine monomers, thiol monomers, sulfide monomers, alkynylly unsaturated monomers, nitrone monomers, aldehyde monomers and ketone monomers, at a level up to about 50 wt % of the sulfur copolymer. Such sulphur copolymers can be as generally described in WO2013/023216 and U.S. Provisional Patent Application No. 61/940,102, filed Feb. 14, 2014, with the addition of one or more photoactive monomers as described herein. Accordingly, in certain embodiments, the sulfur copolymer is further described with respect to any embodiment or claim of WO2013/023216 and U.S. Provisional Patent Application No. 61/940,102, each of which is hereby incorporated herein by reference for all purposes. Non-limiting examples of other monomers are described in U.S. Provisional Patent Application No. 62/017,750, filed Jun. 26, 2014, which are incorporated herein by reference.

In some embodiments, each B includes the polymerizable moiety and a 1-6 atom long linker. Each linker is selected from a group consisting of an alkylene linker and a mono, di- or tri(ethylene glycol) linker. In some embodiments, each B includes an ethylenically unsaturated moiety, an epoxide moiety, a thiirane moiety, or one or more carboxylic anhydrides.

In some embodiments, each photoactive monomer is a photosensitizer. Each photoactive monomer may be a perylene diimide or a perylene bisimide. IN some embodiments, each photoactive monomer is a polycyclic organic chromophore. The photoactive monomer is capable of absorbing visible radiation, infrared radiation, and/or solar radiation. In some embodiments, the one or more photoactive monomers are present at a level of about 0.1 wt % to about 10 wt % of the sulfur copolymer, or 10 wt % to about 20 wt %, or 20 wt % to about 30 wt %, or 30 wt % to 40 wt %, or 40 wt % to about 50 wt %, or 1 wt % to about 5 wt %, or 5 wt % to about 15 wt %, or 15 wt % to 25 wt % of the polymeric composition.

In some embodiments, the one or more additional monomers are one or more ethylenically unsaturated monomers. In other embodiments, the one or more monomers are one or more epoxide monomers. In still other embodiments, the one or more monomers are a combination of one or more ethylenically unsaturated monomers and one or more epoxide monomers. In further embodiments, the one or more monomers are a combination of one or more thiirane monomers and one or more epoxide monomers.

In some embodiments, the sulfur copolymer comprises one or more sulfur monomers at a level in the range of about 50 to about 60 wt %, or about 60 to 70 wt %, or about 70 to 80 wt %, or about 80 to 90 wt %, or about 90 to 99.9 wt %, of the copolymer, and the other monomers at a total level in the range of about 0.01 to 1 wt %, or about 1 to 5 wt %, or about 5 to 10 wt %, or about 10 to 20 wt %, or about 20 to 30 wt %, or about 30 to 40 wt %, or about 40 to 50 wt % of the copolymer. In other embodiments, the sulfur copolymer comprises one or more sulfur monomers at a level in the range of about 50 to about 99 wt % of the copolymer, and the other monomers at a total level in the range of about 1 wt % to about 50 wt % of the copolymer. In still other embodiments, the sulfur copolymer comprises one or more sulfur monomers at a level in the range of about 50 to about 97.5 wt % of the copolymer, and the one or more monomers at a level in the range of about 2.5 wt % to about 50 wt % of the copolymer. In further embodiments, the sulfur copolymer comprises one or more sulfur monomers at a level in the range of about 50 to about 95 wt % of the copolymer, and the other monomers at a level in the range of about 5 wt % to about 50 wt % of the copolymer.

In some embodiments, the sulfur copolymer comprises one or more sulfur monomers at a level of at least about 60 wt % of the copolymer. In other embodiments, the sulfur copolymer comprises one or more sulfur monomers at a level in the range of about 70 to about 92 wt % of the copolymer. In still other embodiments, the sulfur copolymer comprises the other monomers at a level in the range of about 8 wt % to about 30 wt % of the copolymer.

Alternative embodiments of the sulfur copolymers may include sulfur copolymers further comprising one or more polyfunctional monomers (e.g., difunctional or trifunctional). The one or more polyfunctional monomers is selected from a group consisting of a polyvinyl monomer (e.g., divinyl, trivinyl), a polyisopropenyl monomer (e.g., diisoprenyl, triisoprenyl), a polyacryl monomer (e.g., diacryl, triacryl), a polymethacryl monomer (e.g., dimethacryl, trimethacryl), a polyunsaturated hydrocarbon monomer (e.g., diunsaturated, triunsaturated), a polyepoxide monomer (e.g., diepoxide, triepoxide), a polythiirane monomer (e.g., dithiirane, trithiirane), a polyalkynyl monomer, a polydiene monomer, a polybutadiene monomer, a polyisoprene monomer, a polynorbornene monomer, a polyamine monomer, a polythiol monomer, a polysulfide monomer, a polyalkynylly unsaturated monomers, a polynitrone monomers, a polyaldehyde monomers, a polyketone monomers, and a polyethylenically unsaturated monomers.

In some embodiments, the one or more polyfunctional monomers is selected from a group consisting of a divinylbenzene, a diisopropenylbenzene, an alkylene di(meth)acrylate, a bisphenol A di(meth)acrylate, a terpene, a carotene, a divinyl (hetero)aromatic compound and a diisopropenyl (hetero)aromatic compound.

In other embodiments, the sulfur copolymer further comprises a nucleophilic viscosity modifier at a level up to about 10 wt % of the sulfur copolymer.

In one embodiment, the sulfur copolymer comprises one or more sulfur monomers, at a level of about 50 to about 98 wt % of the sulfur copolymer, one or more polyfunctional monomers, at a level of about 2 to about 50 wt % of the sulfur copolymer, and one or more monofunctional monomers, at a level up to about 10 wt % of the sulfur copolymer. The monofunctional and polyfunctional monomers can be photoactive monomers or additional monomers. The one or more sulfur monomers, the one or more polyfunctional monomers, and the one or more monofunctional monomers are present at a level of at least about 70 wt % of the sulfur copolymer. Alternatively the one or more sulfur monomers, the one or more polyfunctional monomers and the optional one or more monofunctional monomers are present at a level of at least about 85 wt % of the sulfur copolymer.

In some embodiments, the one or more polyfunctional monomers are at a level of about 2 to about 50 wt %, or about 2 to about 10 wt %, or about 10 to about 20 wt %, or about 20 to about 30 wt %, or about 30 to about 40 wt %, or about 40 to about 50 wt % of the sulfur copolymer. In some embodiments, the one or more monofunctional monomers are at a level up to about 5 wt %, or about 10 wt %, or about 15 wt % of the sulfur copolymer.

In another embodiment, the sulfur copolymer comprises one or more sulfur monomers, at a level in the range of about 70 to about 92 wt % of the sulfur copolymer, one or more polyfunctional monomers selected from a group consisting of a divinylbenzene, a diisopropenylbenzene and an alkylene di(meth)acrylate, at a level in the range of about 8 to about 30 wt % of the sulfur copolymer, one or more monofunctional monomers, at a level up to about 1.5 wt % of the sulfur copolymer, and triphenylphosphine at a level up to about 20 wt % of the sulfur. The monofunctional monomers and the polyfunctional monomers are photoactive monomers or additional monomers.

In some embodiments, the polymeric composition is a photosentizable material. The polymeric composition is in a photosensitized state. In some embodiments, the polymeric composition is photosensitizable by visible or near-infrared radiation. In other embodiments, the polymeric composition may also be photosensitizable by solar radiation.

The polymeric composition may be processable via solution or melt processing methods. In some embodiments, the polymeric composition is in the form of a thin film. In other embodiments, the polymeric composition is in the form of a three-dimensional solid having a smallest dimension at least 1 mm in size.

In some embodiments, the polymeric composition is contacted with an aqueous medium and irradiated with radiation that is at least partially absorbed by the one or more photoactive chromophores. The irradiation may form photoactive species. The irradiation may cause the formation of hydrogen from the aqueous medium. The irradiation may also the formation of oxidized sulfur species from the sulfur of the polymeric composition. In some embodiments, the oxidized sulfur species is one or more of sulfates, sulfonates, sulfites, sulfoxides and sulfones. In other embodiments, the irradiation causes the formation of a sulfur radical cation or polaron in the polymeric composition.

In some embodiments, the above-method done on the polymeric composition is performed at a temperature in the range of about 0° C. to about 100° C., or about 5° C. to about 70° C., or about 5° C. to about 55° C., or about 25° C. to about 70° C.

In some embodiments, the aqueous solution and the polymeric material are present in a weight ratio in the range of about 100:1 to about 1:10, or about 100:1 to about 1:10, or about 100:1 to about 1:1, or about 100:1 to about 5:1.

In some embodiments, the radiation is solar radiation. In other embodiments, the radiation is visible radiation. In still other embodiments, the radiation is near-infrared radiation.

The following are non-limiting examples of materials that have been synthesized.

Example 10

Preparation of 3,4,9,10-Perylene-tetracarboxylic dianhydride with $S_8$

Experimental

Figure 19A:
FIG. 19a-19c shows various copolymers from the reactions of 3,4,9,10-Perylene-tetracarboxylic dianhydride and $S_8$ with other components.

A mixture of 3,4,9,10-Perylene-tetracarboxylic dianhydride (1 mg) and $S_8$ (1.01 g) was heated at 170° C. and stirred for 30 min. After allowing to cool to room temperature, a red solid was afforded, as shown in FIG. 19a. (Yield: 97%)

Preparation of 3,4,9,10-Perylene-tetracarboxylic dianhydride with $S_8$-10% DIB

Experimental

Figure 19B:
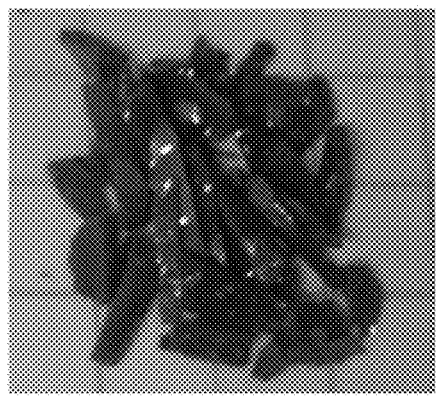

A mixture of 3,4,9,10-Perylene-tetracarboxylic dianhydride (1 mg) and $S_8$ (1.01 g) was heated at 170° C. and stirred for 15 min. 0.1236 g of 1,3-diisopropenylbenzene was added and stirred for another 30 min. After allowing to cool to room temperature, a red solid was afforded, as shown in FIG. 19b. (Yield: >99%)

Preparation of 3,4,9,10-Perylene-tetracarboxylic dianhydride with $S_8$-10% Styrene (ST)

Experimental

Figure 19C:
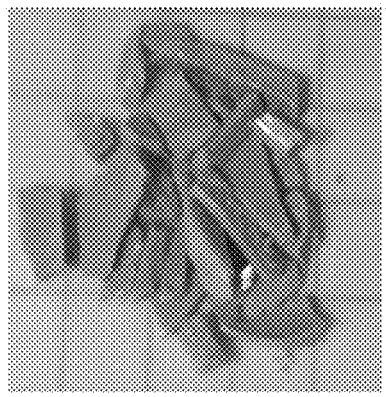

A mixture of 3,4,9,10-Perylene-tetracarboxylic dianhydride (1 mg) and $S_8$ (1.01 g) was heated at 170° C. and stirred for 15 min. 0.1249 g of styrene was added and stirred for another 30 min. After allowing to cool to room temperature, a light red solid was afforded, as shown in FIG. 19c. (Yield: 96%)

Example 11

Preparation of N,N'-dibutyl perylenecarboxydiimide wih $S_8$

Figure 20A:
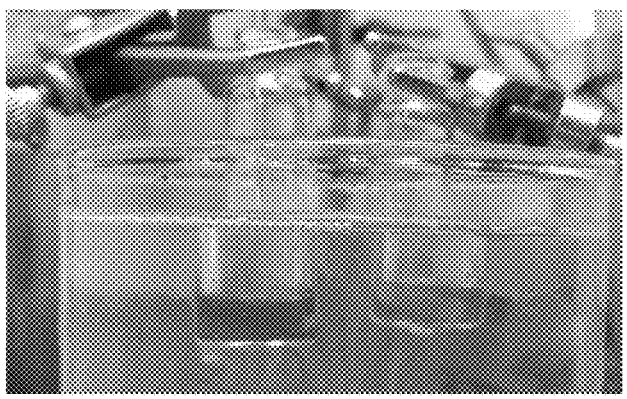
FIG. 20a-20e shows various copolymers from the reactions of N,N'-dibutyl perylenecarboxydiimide and $S_8$ with other components.
Figure 20B:
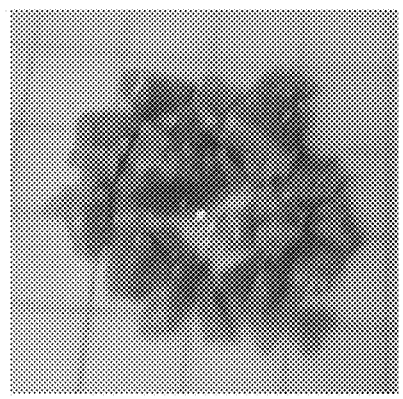

Experimental: A mixture of N,N'-dibutyl perylenecarboxydiimide (1 mg) and $S_8$ (1.01 g) was heated at 170° C. and stirred for 30 min, as shown in FIG. 20a. The product was allowed to cool to room temperature, as shown in FIG. 20b. (Yield: >99%)

Preparation of N,N'-dibutyl perylenecarboxydiimide with $S_8$ and 1,3-diisopropenylbenzene (DIB)

Experimental

Figure 20C:
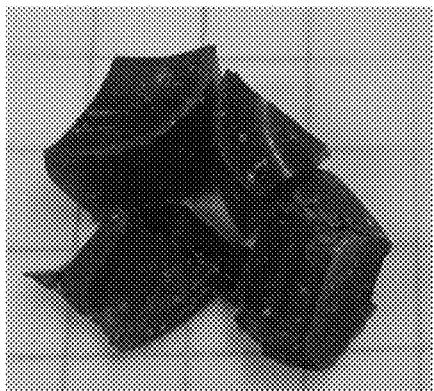

A mixture of N,N'-dibutyl perylenecarboxydiimide (1 mg) and $S_8$ (1.01 g) was heated at 170° C. and stirred for 30 min. 0.12 g of 1,3-diisopropenylbenzene was added and the mixture was stirred for another 30 min. After allowing to cool to room temperature, a red solid was afforded, as shown in FIG. 20c. (Yield: 98%)

Preparation of N,N'-dibutyl perylenecarboxydiimide with $S_8$-10% ST Copolymer

Experimental

Figure 20D:
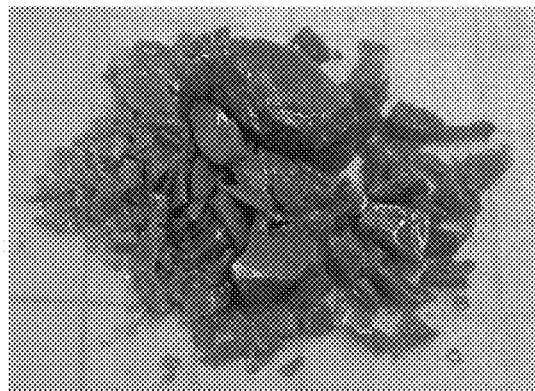

A mixture of N,N'-dibutyl perylenecarboxydiimide (1 mg) and $S_8$ (1.01 g) was heated at 170° C. and stirred for 30 min. 0.11 g of 1,3-diisopropenylbenzene was added and the mixture was stirred for another 30 min. After allowing to cool to room temperature, a dark yellow, beige solid was afforded, as shown in FIG. 20d. (Yield: 96%)

Figure 20E:
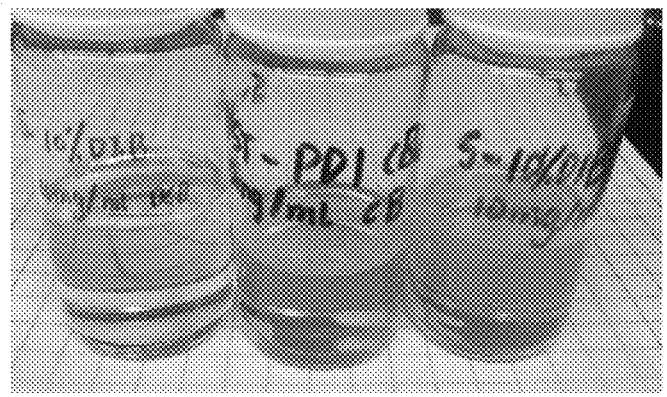

1,2-dichlorobenzene (DCB) or chlorobenzene (CB) solution of N,N'-dibutyl perylenecarboxydilmide with Sulfur Copolymer Referring now to FIG. 20e, the first vial from the left shows a mixture of 0.1 g of $S_8$-10% DIB copolymer dissolved in 10 mL of 1,2-dichlorobenzene. The second vial shows a mixture of 0.1 g of $S_8$-10% ST copolymer and 0.5 mg of N,N'-dibutyl perylenecarboxydiimide dissolved in 10 mL of chlorobenzene. The third vial shows a mixture of 0.1 g of $S_8$-10% DIB copolymer and 0.5 mg of N,N'-dibutyl perylenecarboxydiimide dissolved in 10 mL of 1,2-dichlorobenzene.

Additional aspects of the polymers are described below. The polymers described below do not generally include a photoactive chromophore; the person of ordinary skill in the art can adapt any such polymers for use with photoactive chromophores as described herein.

The sulfur can be provided as elemental sulfur, for example, in powdered form. Under ambient conditions, elemental sulfur primarily exists in an eight-membered ring form (Sa) which melts at temperatures in the range of 120-124° C. and undergoes an equilibrium ring-opening polymerization (ROP) of the $S_8$ monomer into a linear polysulfane with diradical chain ends, above 159° C., as shown in schematic view in FIG. 1.

As the person of skill in the art will appreciate, while Sa is generally the most stable, most accessible and cheapest feedstock, many other allotropes of sulfur can be used (such as other cyclic allotropes, derivable by melt-thermal processing of $S_8$). Any sulfur species that yield diradical or anionic polymerizing species when heated as described herein can be used in practicing the present invention.

Because both anionic and radical polymerization can occur in the polymerization reaction mixtures, any desirable combination of amine monomers, thiol monomers, sulfide monomers, alkynylly unsaturated monomers, nitrone and/or nitroso monomers, aldehyde monomers, ketone monomers, thiirane monomers, ethylenically unsaturated monomers, and/or epoxide monomers can be used in the copolymers. As a non-limiting example, in certain embodiments, one or more monomers are one or more ethylenically unsaturated monomers.

Because both radical and anionic species can be generated during the same polymerization, it is possible to incorporate both amine monomers, thiol monomers, sulfide monomers, alkynylly unsaturated monomers, nitrone and/or nitroso monomers, aldehyde monomers, ketone monomers, thiirane monomers, ethylenically unsaturated monomers, and/or epoxide monomers into the same copolymer. As non-limiting examples, in one embodiment of the invention, the one or more monomers are a combination of one or more amine monomers and one or more thiol monomers. In other embodiments of the invention, the one or more monomers are a combination of one or more amine monomers, thiol monomers, sulfide monomers, alkynylly unsaturated monomers, nitrone and/or nitroso monomers, aldehyde monomers, ketone monomers, thiirane monomers, ethylenically unsaturated monomers, and/or epoxide monomers; and one or more amine monomers, thiol monomers, sulfide monomers, alkynylly unsaturated monomers, nitrone and/or nitroso monomers, aldehyde monomers, ketone monomers, thiirane monomers, ethylenically unsaturated monomers, and/or epoxide monomers.

In still other embodiments of the invention, the one or more monomers are a combination of one or more amine monomers, thiol monomers, sulfide monomers, alkynylly unsaturated monomers, nitrone and/or nitroso monomers, aldehyde monomers, ketone monomers, thiirane monomers, and ethylenically unsaturated, and/or epoxide monomers; and one or more amine monomers, thiol monomers, sulfide monomers, alkynylly unsaturated monomers, nitrone and/or nitroso monomers, aldehyde monomers, ketone monomers, thiirane monomers, ethylenically unsaturated monomers, and/or epoxide monomers; and one or more amine monomers, thiol monomers, sulfide monomers, alkynylly unsaturated monomers, nitrone and/or nitroso monomers, aldehyde monomers, ketone monomers, thiirane monomers, ethylenically unsaturated monomers, and/or epoxide monomers.

The person of skill in the art will select monomers and relative ratios thereof in order to provide the desired properties to the polymer. In certain embodiments, the one or more monomers include one or more polyfunctional monomers, optionally in combination with one or more monofunctional monomers. A polyfunctional monomer is one that includes more than one (e.g., 2, or 3) polymerizable amine, thiol, sulfide, alkynylly unsaturated, nitrone and/or nitroso, aldehyde, ketone, thiirane, ethylenically unsaturated, and/or epoxide moieties. Polyfunctional monomers can be used to cross-link sulfur chains to adjust the properties of the polymer, as would be understood by the person of skill in the art. The multiple polymerizable groups of a polyfunctional monomer can be the same or different. For example, a polyfunctional monomer can be a polyvinyl monomer, a polyisopropenyl monomer, a polyacryl monomer, a polymethacryl monomer, a polyunsaturated hydrocarbon monomer, a polyepoxide monomer, a polythiirane monomer, a polyalkynyl monomer, a polydiene monomer, a polybutadiene monomer, a polyisoprene monomer, a polynorbornene monomer, a polyamine monomer, a polythiol monomer, a polysulfide monomer, a polyalkynylly unsaturated monomers, a polynitrone monomers, a polyaldehyde monomers, a polyketone monomers, and a polyethylenically unsaturated monomers In other embodiments, a polyfunctional monomer can be a polyepoxide monomer or a polythiirane monomer.

Fréchet-type benzyl ether dendrimers bearing styrenic terminal groups are miscible with liquid sulfur and can be used as polyfunctional cross-linkers. In certain embodiments, the one or more polyfunctional monomers include one or more of a divinylbenzene, a diisopropenylbenzene, an alkylene di(meth)acrylate, a bisphenol A di(meth)acrylate, a terpene, a carotene, a divinyl (hetero)aromatic compound, and a diisopropenyl (hetero)aromatic compound. In other embodiments, a polyfunctional monomer can have one or more amine, thiol, sulfide, alkynylly unsaturated, nitrone and/or nitroso, aldehyde, ketone, thiirane, ethylenically unsaturated, and/or epoxide moieties moieties; and one or more amine, thiol, sulfide, alkynylly unsaturated, nitrone and/or nitroso, aldehyde, ketone, thiirane, ethylenically unsaturated, and/or epoxide moieties, wherein the first and second moieties are different. A non-limiting example is a divinylbenzene monoxide.

The polymeric materials can be made, for example, by polymerization of molten sulfur with the monomers. Thus, in one aspect, the invention provides a method for making a polymeric composition as described above. The method includes heating a mixture including sulfur and the one or more monomers together at a temperature sufficient to initiate polymerization (i.e., through free radical polymerization, through anionic polymerization, or through both, depending on the monomers used). For example, in one embodiment, the method includes heating a mixture including sulfur and the one or more monomers together at a temperature in the range of about 120° C. to about 230° C., e.g., in the range of about 160° C. to about 230° C. The person of skill in the art will select conditions that provide the desired level of polymerization, using, in part, information provided in the Examples, below. In one embodiment, the mixture comprising sulfur and one or more monomers is formed by first heating a mixture comprising sulfur to form a molten sulfur, then adding one or more monomers to the molten sulfur. In certain embodiments, the polymerization reaction is performed under ambient pressure. However, in other embodiments, the polymerization reaction can be performed at elevated pressure (e.g., in a bomb or an autoclave). Elevated pressures can be used to polymerize more volatile monomers, so that they do not vaporize under the elevated temperature reaction conditions.

In certain embodiments, it can be desirable to use a nucleophilic viscosity modifier in liquefying the sulfur, for example, before adding one or more of the monomers (e.g., before adding any polyfunctional monomer). For example, in certain embodiments, the sulfur is first heated with a viscosity modifier, then the viscosity-modified sulfur is heated with one or more monomers (e.g., with one or more polyfunctional monomers). The nucleophilic viscosity modifier can be, for example, a phosphorus nucleophile (e.g., a phosphine), a sulfur nucleophile (e.g., a thiol) or an amine nucleophile (e.g., a primary or secondary amine). When sulfur is heated in the absence of a nudeophilic viscosity modifier, the sulfur rings can open to form, e.g., diradicals, which can combine to form linear polysulfide chains which can provide a relatively high overall viscosity to the molten material. Nucleophilic viscosity modifiers can break these linear chains into shorter lengths, thereby making shorter polysulfides that lower the overall viscosity of the molten material, making the sulfur mixture easier to mix with and other species, and easier to stir for efficient processing. Some of the nucleophilic viscosity modifier will react to be retained as a covalently bound part of the copolymer, and some will react to form separate molecular species, with the relative amounts depending on nucleophile identity and reaction conditions. For example, triphenylphosphine can react with $S_8$ to form triphenylphosphonium-terminated linear sulfides (which can go on to form copolymer) together with triphenylphosphine sulfide (unbound). While some of the nucleophilic viscosity modifier may end up as a separate molecular species from the polymer chain, as used herein, nucleophilic viscosity modifiers are considered to be part of the copolymer. Non-limiting examples of nucleophilic viscosity modifiers include triphenylphosphine, aniline, benzenethiol, and N,N-dimethylaminopyridine. Nucleophilic viscosity modifiers can be used, for example, in an amount up to about 10 wt %, or even up to about 5 wt % of the copolymer. When a nucleophilic viscosity modifier is used, in certain embodiments it can be used in the range of about 5 wt % to about 15 wt % of the sulfur.

In certain embodiments, a monofunctional monomer can be used to reduce the viscosity of the sulfur, for example, before adding other of the monomers (e.g., before adding any polyfunctional monomer). For example, in certain embodiments, the sulfur is first heated with one or more monofunctional monomers, then the resulting mixture is heated with one or more other monomers (e.g., with one or more polyfunctional monomers). While not intending to be bound by theory, the inventors surmise that inclusion of monofunctional monomers into the polysulfide chains disrupts intermolecular associations of polysulfides and thus decreases the viscosity. The monofunctional monomer can be, for example, a mono(meth)acrylate such as benzyl methacrylate, a mono(oxirane) such as a styrene oxide or a glycidyl phenyl ether, or a mono(thiirane) such as t-butyl thiirane or phenoxymethylthiirane. A monofunctional monomer can be used to modify the viscosity of the sulfur, for example, in an amount up to about 10 wt %, up to about 5 wt %, or even up to about 2 wt % of the copolymer. When a monofunctional monomer can be used to modify the viscosity of the sulfur, in certain embodiments it can be used in the range of about 0.5 wt % to about 5 wt %, or even about 0.5 wt % to about 3 wt % of the sulfur.

Of course, viscosity modification is not required, so in other embodiments the sulfur is heated together with the one or more monomers (and particularly with one or more polyfunctional monomers) without viscosity modification. In other embodiments, a solvent, e.g., a halobenzene such as 1,2,4-trichlorobenzene, a benzyl ether, or a phenyl ether, can be used to modify the viscosity of the materials for ease of handling. The solvent can be added, for example, to the sulfur before reaction with a monomer in order to reduce its viscosity, or to the polymerized material in order to aid in processing into a desired form factor.

The one or more thiirane monomers can include polyfunctional and/or monofunctional monomers as described elsewhere herein. Non-limiting examples of monomers include propylene sulfide, t-butyl thiirane, phenoxymethyl thiirane, vinylthiirane, and 2-((allyloxy)methyl)thiirane. For example, in one embodiment, the copolymer is a copolymer of sulfur and an alkylene sulfide such as propylene sulfide. Other characteristics of these copolymers can be as defined for other materials described herein. Such materials can be made into polymeric compositions, composites and devices as otherwise described herein. Advantageously, sulfur/thiirane copolymers of up to about 80 wt % sulfur can be soluble in a variety of solvents, such as N-methylpyrrolidinone, toluene, $CS_2$ and tetrahydrofuran.

Another aspect of the invention is a method for making a sulfur/thiirane copolymer as described above. The method includes allowing the thiirane monomer(s) to react with the sulfur—in the amounts appropriate to provide the desired copolymer composition as described above—with a thioester (—C(S)—S—) or trithiocarbonyl (—S—C(S)—S—) based RAFT polymerization agent in a solvent. Suitable RAFT polymerization agents include, for example, benzyl dithiobenzoate. The polymerization can be performed, for example, at a temperature in the range of about 20° C. to about 120° C., for example, from about 20° C. to about 90° C. The solvent can be selected by the person of skill in the art in view of the particular materials used; examples include N-methylpyrrolidinone and toluene. A catalyst, such as tetraphenylphosphonium chloride can optionally be used. The person of skill in the art can adapt known RAFT polymerization techniques for use in making the copolymers described herein. For example, chain transfer agents based on dithioesters, trithiocarbonyls, dithiocarbamates, and xanthates can generally be adapted by the person of skill in the art for use in making the copolymers described herein, as can-onium salts (e.g., those based on phosphonium halides, imidazolium halides and ammonium halides).

The polymers described herein can be partially cured to provide a more easily processable material, which can be processed into a desired form (e.g., into a desired shape, such as in the form of a free-standing shape or a device), then fully cured in a later operation. For example, one embodiment of the invention is a method of making an article formed from a polymeric composition as described herein. The method includes heating a mixture comprising sulfur and one or more monomers at a temperature in the range of about 160° C. to about 230° C. to form a prepolymer; forming the prepolymer into the shape of the article, to yield a formed prepolymer shape; and further heating the formed prepolymer shape to yield the article. The prepolymer can be formed, for example, by conversion of the one or more monomers at a level in the range of about 20 to about 50 mol %. For example, the heating of the sulfur and the one or more monomers to form the prepolymer can be performed for a time in the range of about 20 seconds to about five minutes, for example, at a temperature in the range of about 175° C. to about 195° C. In one embodiment, the heating is performed for less than about 2 minutes at about 185° C. The person of skill in the art will determine the desired level of monomer conversion in the prepolymer stage to yield a processable prepolymer material, and will determine process conditions that can result in the desired level of monomer conversion.

In one embodiment, the prepolymer can be provided as a mixture with a solvent for forming, e.g., via casting, molding or printing. The prepolymers described herein can form miscible mixtures or solutions with a variety of nonpolar high-boiling aromatic solvents, including, for example, haloarene solvents such as di- and trichlorobenzene (e.g., 1,2,4-trichlorobenzene). The solvent can be added, for example, after the prepolymer is prepared, to provide a softened or flowable material suitable for a desired forming step (e.g., casting, molding, or spin-, dip- or spray-coating.) In some embodiments, the prepolymer/solvent mixture can be used at elevated temperatures (e.g., above about 100° C., above about 120° C. or above about 140° C.) to improve flow at relatively low solvent levels (e.g., for use in casting or molding processes). In other embodiments, the prepolymer/solvent mixture can be used at a lower temperature, for example, at ambient temperatures (e.g., for use in spin-coating processes); unlike molten sulfur, the prepolymers described herein can remain soluble even after the solvent cools.

In one embodiment, the prepolymer is coated and cured as a film on a substrate. While $S_8$ is typically intractable due to its crystallinity, the materials described herein can be formed as to be amenable to solution processing (e.g., in molten or solvent-admixed form) to fabricate thin film materials. Mixtures of molten prepolymer and solvent can be diluted to the concentration desired for a given spin-coating process.

When forming thin films of the materials described herein on substrates, it can often be desirable to use a polyimide primer layer. Thus, a solution of a polyamic precursor (e.g., polypyromellitamic acid-4,4'-dianiline, or compounds with oxyaniline linkages), or similar copolymer derivatives can be deposited onto a substrate and cured (e.g., by heating at a temperature in the range of about 120 to about 200° C.) to form a thin polyimide layer (e.g., as thin as 2 nm), upon which the materials described herein can be formed. Moreover, in many embodiments, even fully cured polymers as described herein can be melt processed or suspended or dissolved in solvent and deposited on to substrates in a manner similar to those described for prepolymeric materials.

In certain embodiments, the prepolymer can be shaped and cured using a mold. For example, in one embodiment, the prepolymer (i.e., in molten or solvent-admixed form) can be deposited (e.g., by pouring) into a TEFLON or silicone (e.g., polydimethylsiloxane (PDMS)) mold, then cured to form a desired shape. In another embodiment, a softened prepolymer material (e.g., swollen with solvent and/or softened by heat) can be imprinted by stamping with a mold bearing the desired inverse surface relief, then cured and allowed to cool. Moreover, in many embodiments, even fully cured polymers as described herein can be shaped with a mold in a manner similar to those described for prepolymeric materials.

As described above, soluble copolymers can be made by the person of skill in the art, for example, using relatively higher fractions of organic comonomer(s). Such polymers can be solution processed to fabricate articles. For example, another aspect of the invention is a method of forming an article formed from a polymeric composition as described herein, the method comprising admixing the polymeric composition with a nonpolar organic solvent (e.g., to make a suspension or solution), forming the admixed polymeric composition into the shape of the article,] and removing the solvent from the polymeric composition to yield the article. The admixture with solvent can, for example, dissolve the copolymer. Various process steps can be performed at elevated temperatures, for example, to decrease viscosity of the admixed polymeric composition and to aid in evaporation of solvent.

For example, in one embodiment, a room temperature solution (e.g., in a dichlorobenzene or a trichlorobenzene) of a random copolymer (e.g., in prepolymeric form) prepared via the thermal free radical copolymerization of $S_8$ and 1,3-diisopropenylbenzene (poly(S-r-DIB)) (72.5 wt % sulfur, 27.5 wt % DIB) is poured into a TEFLON or PDMS mold. A decrease in viscosity at elevated temperatures (e.g., >about 140° C.) can allow sufficient flow into even intricate mold shapes. Once the mold is filled, it can be placed in a vacuum oven at increased temperature (e.g., about 210° C.) under ambient pressure to cure and to drive off solvent. For thicker molded samples, vacuum can be pulled on the solution when it is in a low viscosity state in order to ensure the removal of bubbles. The mold is then removed from the oven and allowed to cool before removal from the mold.

As the polymeric materials described herein can be effectively thermoplastic in nature, the person of skill in the art will understand that other methods familiar in the thermoplastic industries, such as injection molding, compression molding, and melt casting, can be used in forming articles from the materials described herein.

Example 12. Viscosity Modification of Elemental Sulfur

In one experiment, mixtures of sulfur (provided as $S_8$ herein unless otherwise described, 600 mg) with various weight percents of triphenylphosphine (TPP) (2.5, 5, 7.5 and 10 wt % TPP with respect to sulfur) were prepared in 4 mL vials each equipped with a stir bar. The mixtures were heated at 185° C. and stirred at 550 rpm. Their viscosities were assessed qualitatively, and the mixtures containing 7.5 wt % and 10 wt % TPP had markedly lowered viscosities, and remained stirable.

In another experiment, powdered sulfur (0.700 g, 2.19× $10^{-2}$ mol) and benzyl methacrylate (0.0105 g, 10.1 µL, 5.96×$10^{-5}$ mol, 1.5 wt % with respect to total mass) were combined in a 4 mL vial equipped with a stir bar. The vial was sealed and heated at 185° C. while stirring at 550 rpm. The viscosity was assessed visually to be less than that of powdered sulfur alone treated under the same conditions.

Example 13. Copolymerization of Viscosity-Modified Sulfur with Divinylbenzene

In a 4 mL vial equipped with a stir bar were combined powdered sulfur (0.360 g, 1.13×$10^{-2}$ mol) and TPP (0.40 g, 1.53×$10^{-4}$ mol). The vial was loosely capped and then heated at 185° C. with stirring at 550 rpm. The solids were allowed to melt and form a homogeneous liquid. The cap was then removed and divinylbenzene (commercial grade, mixture of 1,3- and 1,4-isomers) (0.198 g, 0.217 mL, 1.52×$10^{0.3}$ mol) was injected. The cap was then quickly replaced and secured tightly. [try reading this out loud and see how many "ands" and verbs are used] The reaction mixture was allowed to stir until gelation prevented further stirring, then the vial was cooled to room temperature.

Example 14. Copolymerization of Viscosity-Modified Sulfur with 1,3-dilsopropenylbenzene In a 4 mL vial equipped with a stir bar were combined powdered sulfur (0.360 g, 1.13×$10^{-2}$ mol) and TPP (0.40 g, 1.53×$10^{-4}$ mol). The vial was loosely capped and heated at 185° C. with stirring at 550 rpm. The solids were allowed to melt and form a homogeneous liquid. The cap was then removed and 1,3-diisopropenylbenzene (DIB) (0.198 g, 0.217 mL, 1.25×$10^3$ mol) was injected and the cap quickly replaced and secured tightly. The mixture was allowed to stir until gelation prevented further stirring, then the vial was cooled to room temperature.

Example 15. Copolymerization of Viscosity-Modified Sulfur with 1,3-diisopropenylbenzene and 1,10-decanediol dimethacrylate In a 4 mL vial equipped with a stir bar were combined powdered sulfur (0.390 g, 1.22×$10^{-2}$ mol) and TPP (0.060 g, 2.29×$10^{-4}$ mol). The vial was loosely capped and heated at 185 C with stirring at 550 rpm. The solids were allowed to melt and form a homogeneous liquid. The cap was then removed and DIB (0.075 g, 81.1 µL, 2.86×$10^{-4}$ mol) and 1,10-decanediol dimethacrylate (0.075 g, 2.42×$10^4$ mol) were simultaneously injected and the cap quickly replaced and secured tightly. The mixture was allowed to stir until gelation prevented further stirring, then the vial was cooled to room temperature.

Figure 21A:
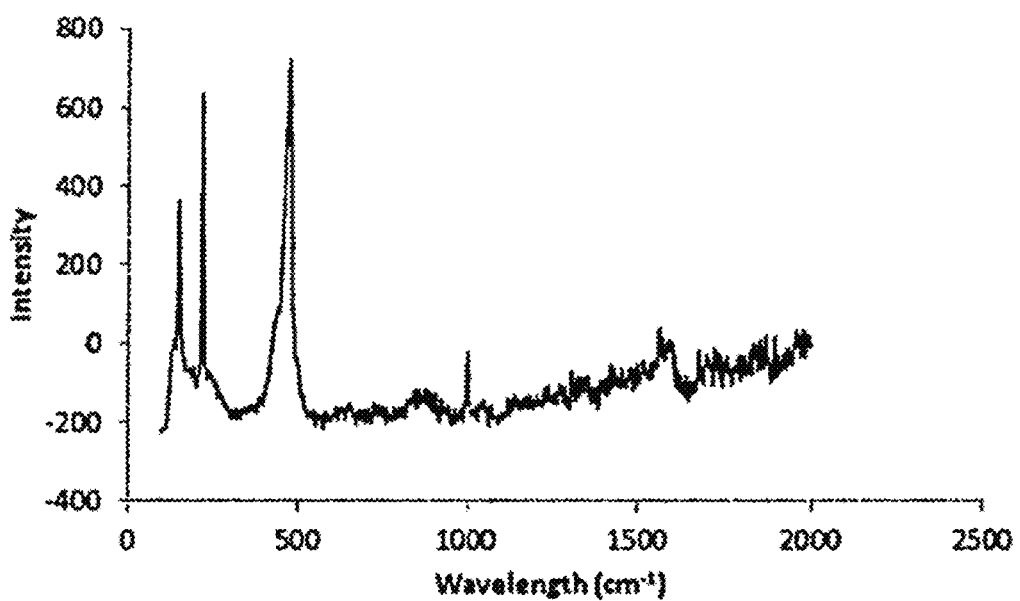
FIG. 21a-21b shows Raman data for copolymers.
Figure 21B:
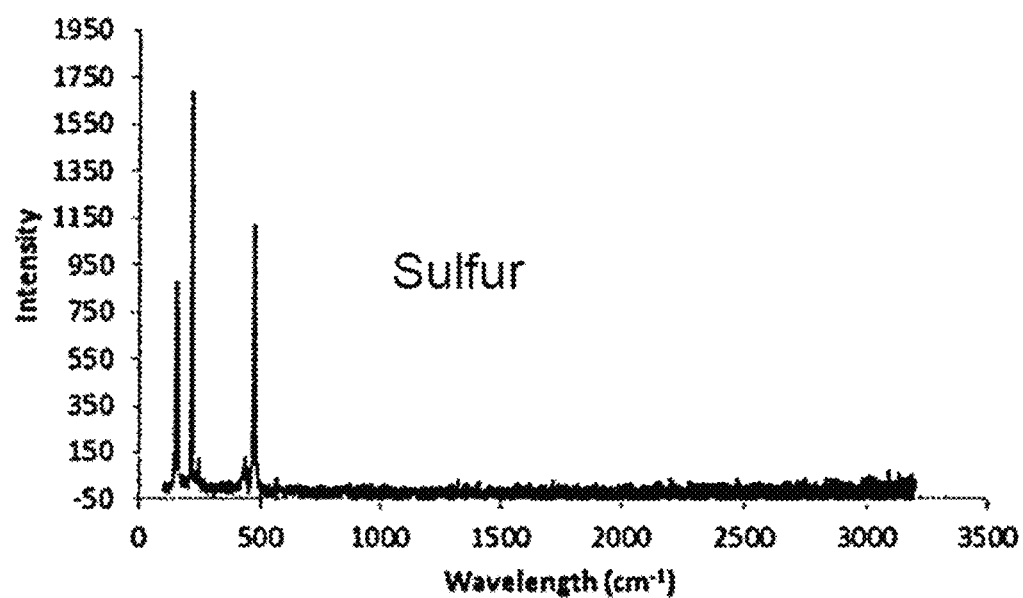
Figure 22A:
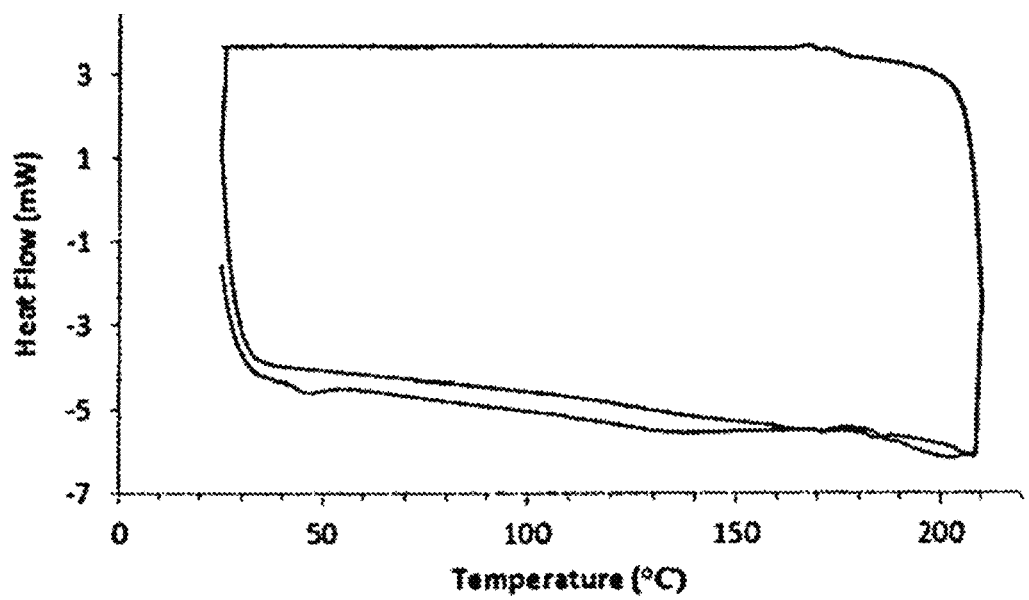
FIG. 22a-22b shows thermograms from DSC data of copolymers.
Figure 22B:
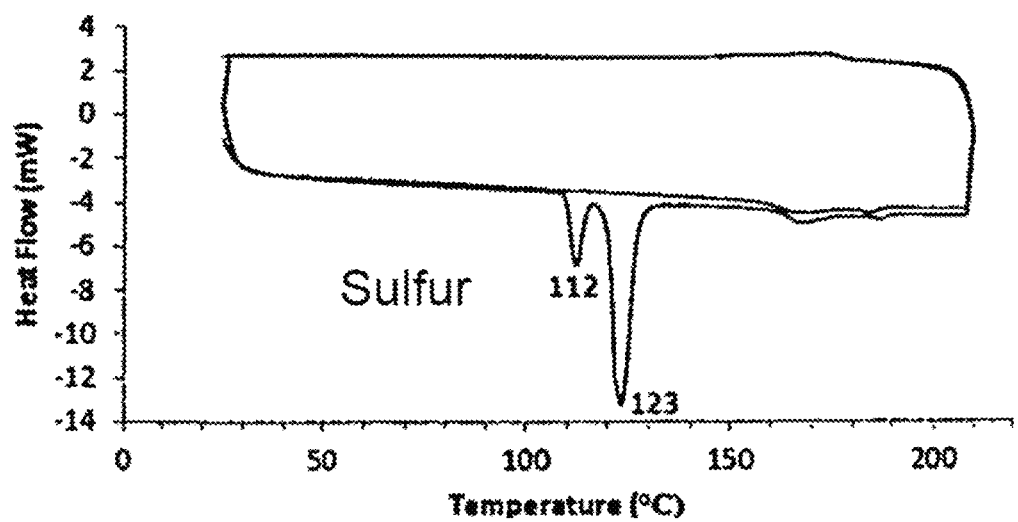

Example 16. Copolymerization of Sulfur with 1,3-diisopropenylbenzene and Benzyl Methacrylate To a 4 mL vial equipped with a stir bar was added powdered sulfur (0.54 g, 2.10×$10^{-3}$ mol). The vial was heated at 185° C. until a clear orange-colored molten phase was formed. Benzyl methacrylate (0.063 g, 60.6 µL, 0.357× $10^{-3}$ mol) was then directly added to the molten sulfur via syringe. The sulfur and benzyl methacrylate were allowed to homogenize, then DIB (0.297 g, 0.321 mL, 1.88×10$^{-3}$ mol) was directly added to the molten mixture via syringe. The resulting mixture was stirred at 185° C. until a deep cherry-red solution resulted and the entire reaction vitrified. Once vitrified the reaction was cooled to room temperature. The resulting copolymer had a sulfur level of 60%, a DIB level of 33%, and a benzyl methacrylate level of 7 wt %. Raman spectra and Differential scanning calorimetry (DSC) thermograms of the resulting copolymer and of elemental sulfur are provided in FIGS. 21a,b and 22a,b, respectively. The Raman and DSC data indicate substantially complete copolymerization.

Example 17. DSC, Kinetics, and Thermal and Rheological Properties

Figure 23A:
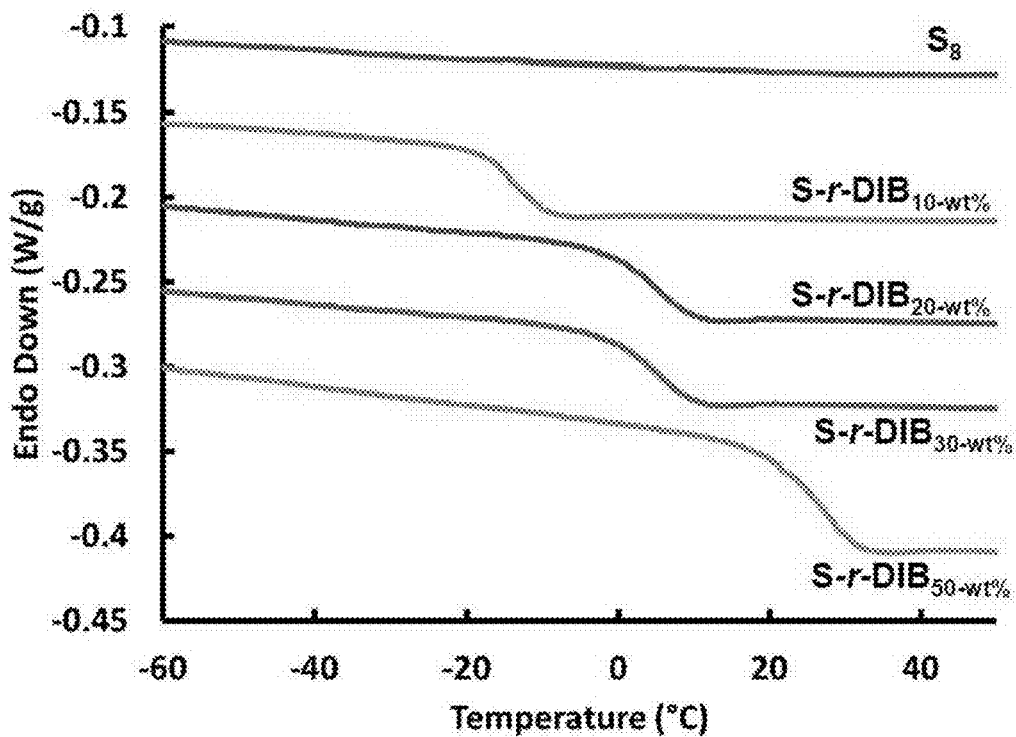
FIG. 23a-23b shows thermograms from DSC data of copolymers.
Figure 23B:
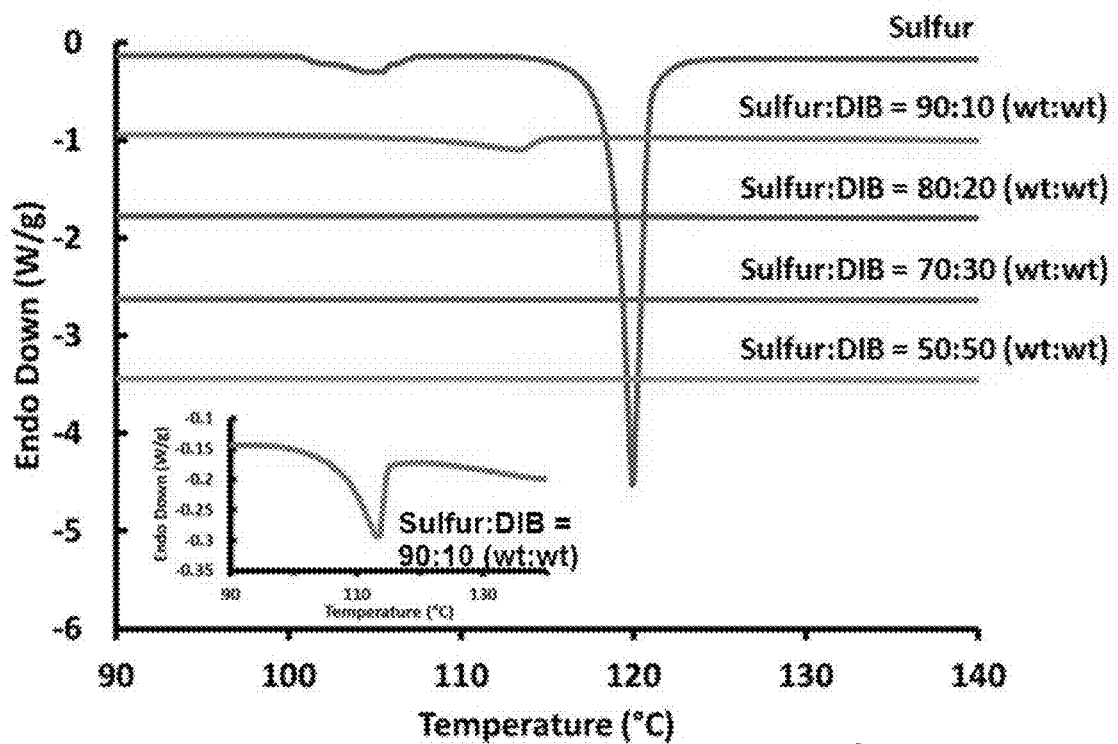

Sulfur-DIB polymers of varying sulfur content were made by heating mixtures of sulfur and DIB at 185° C. The resulting polymers were studied by DSC, along with sulfur; thermograms are provided in FIG. 23a. The sulfur melting endotherm was not present in any of the polymerized material. The 90 wt % sulfur material also did not have residual unreacted $S_8$ monomer, but due to the high sulfur content in the sulfur copolymer exhibited a weak endotherm corresponding to melting of semi-crystalline domains present in sulfur rich polymers. DSC data in the range of −60° C. to 40° C. are provided in FIG. 23b. The glass transition temperature increased with increasing DIB content.

Figure 24:
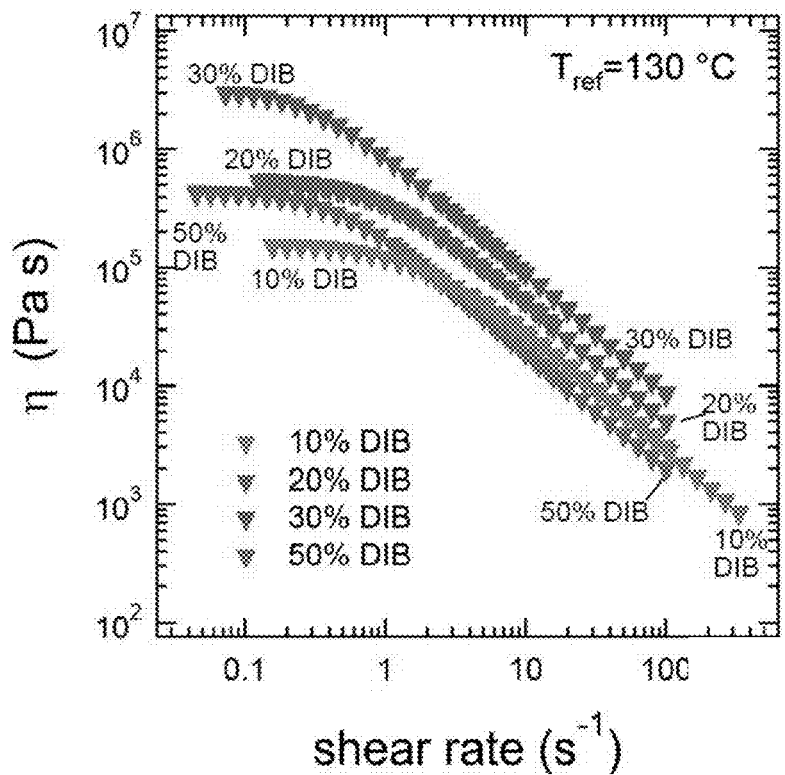
FIG. 24 shows shear viscosity data for copolymers with increasing DIB.
Figure 25:
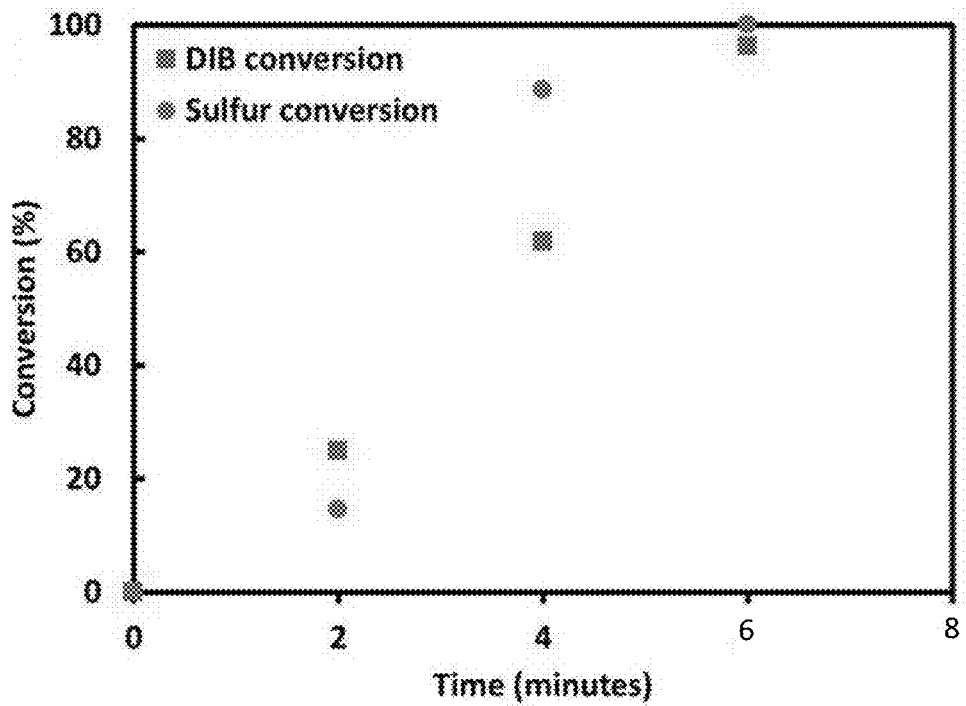
FIG. 25 shows a sulfur and DIB percent conversion.

Shear viscosity data are provided in FIG. 24. Increasing DIB increased zero-shear viscosity until between 30 wt % and 50 wt %, where the zero-shear viscosity increased. While not intending to be bound by theory, the inventors surmise that hyperbranching results in lower viscosity around 50 wt % DIB. A 50:50 mixture of $S_8$ and DIB was heated at 185° C., and samples were obtained every two minutes, cooled quickly, and analyzed via Raman spectroscopy and DSC for sulfur conversion, and $^1$H NMR for DIB vinyl group conversion. Results are shown in FIG. 25, and demonstrate complete reaction within 6 minutes.

Example 18. Preparation of Sulfur/Propylene Sulfide Copolymers

Polymerizations of sulfur and propylene sulfide can be performed using a procedure similar to that described below. Polymerizations were carried out with benzyl dithiobenzoate (BDB) as an initiator in a degassed sealed Schlenk flask. Propylene sulfide (0.88 mL, 11.232×10$^{-3}$ mol), sulfur (0.7188 g, 2.808×10$^{-3}$ mol), BDB (34.2 mg, 0.1404×10$^{0.3}$ mol), tetraphenylphosphonium chloride (10.53 mg, 0.02808×10$^{-3}$ mol), and 10 mL toluene were placed in a Schlenk flask to ensure exclusion of adventitious water, or oxygen, and degassed by three freeze-pump-thaw cycles, then the mixture was stirred at 80° C. for 8 h under argon. The polymer obtained was purified by precipitation from toluene into a large excess of methanol, and dried in vacuum to give a pale red oil polymer.

Figure 26:
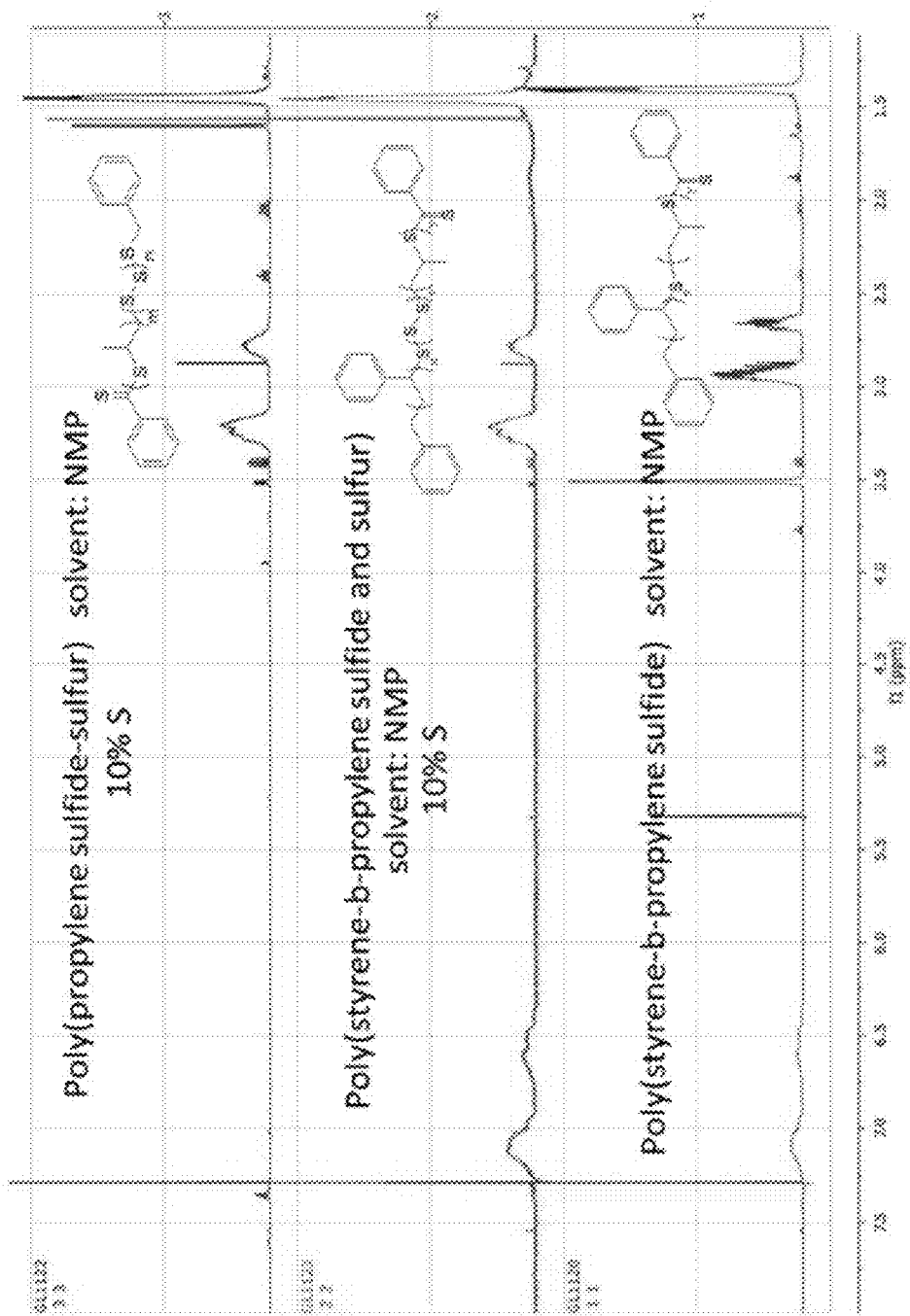
FIG. 26 provides NMR spectra of two sulfur/thiirane copolymers and that of a copolymer not containing sulfur.

FIG. 26 provides NMR spectra of two sulfur/thiirane copolymers and that of a copolymer not containing sulfur. The resonances at 2.5-3.0 ppm shift with increased sulfur content. Similarly, size exclusion chromatography measurements demonstrated sulfur incorporation into the polypropylene backbone, with a broad range of apparent molecular weights (1,000-100,000 g/mol).

Example 19. Formation of Sulfur/DIB Prepolymer Solution

In a 20 mL vial equipped with a stir bar were added powdered sulfur (1.2 g, 3.75×10$^{-2}$ mol) and triphenylphosphine (0.140 g, 5.34×10$^{-4}$ mol). The vial was loosely capped and heated at 185° C. with stirring at 550 rpm. The solids were allowed to melt and form a homogeneous liquid. The cap was then removed and DIB (0.660 g, 0.714 mL, 3.64×10$^{-3}$ mol) was injected and the cap quickly replaced and secured tightly. Once the mixture began to darken to an amber color (after about 2-3 minutes) the cap was removed and 1,2,4-trichlorobenzene (TCB) (0.660 g, 0.714 mL) was injected. The vial was sealed and the mixture was stirred for 2-3 minutes until bright red in color, then cooled to room temperature to form a viscous prepolymer solution.

Example 20. Formation of Polymer Structures

Figure 27:
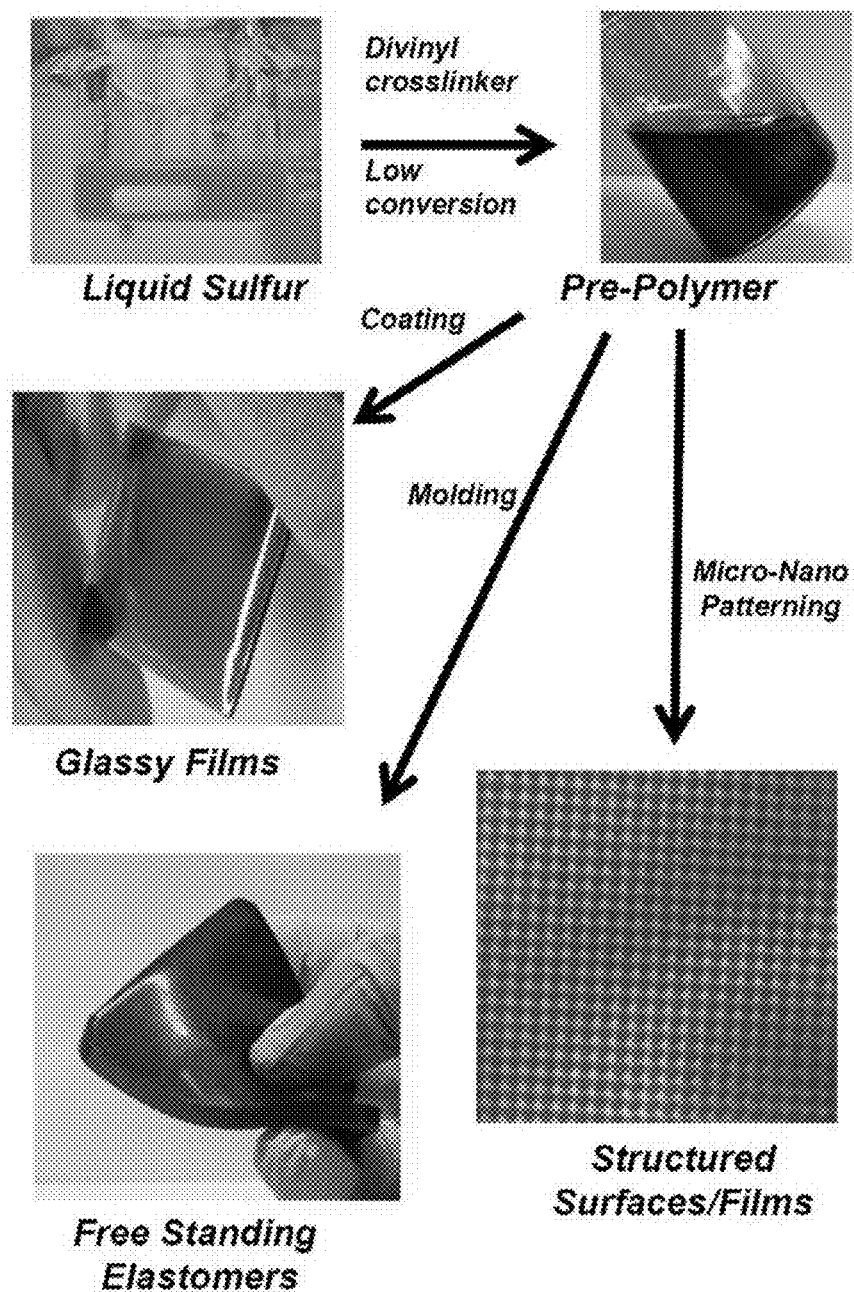
FIG. 27 shows various products prepared from a sulfur prepolymer solution.

Hot prepolymer solutions as described above in Example 19 were poured into Teflon molds of various geometries and cured at 200° C. to form free-standing elastomer structures, an example of which is shown in FIG. 27. Glassy thin films were prepared by drop casting the prepolymer solution as described above onto a glass slide and curing at 200° C. An example is shown in FIG. 27. Microstructures were formed by pouring the prepolymer solution as described above into PDMS molds having pillared features (having micrometer periodicity) and curing at 200° C. An example is shown in FIG. 27.

Figure 28:
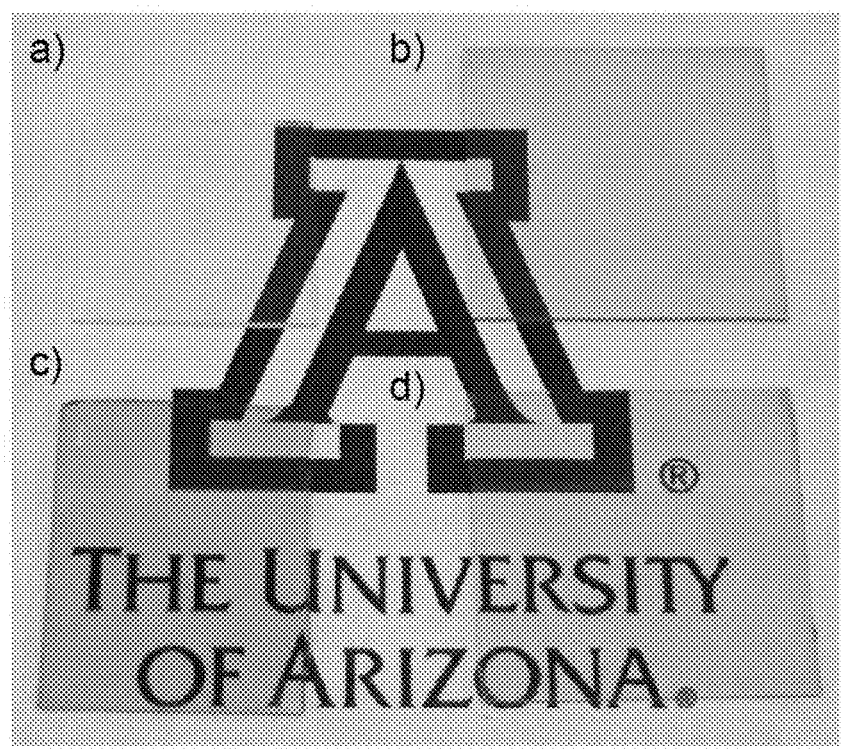
FIG. 28 is a picture of a set of spin-coated films.
Figure 29:
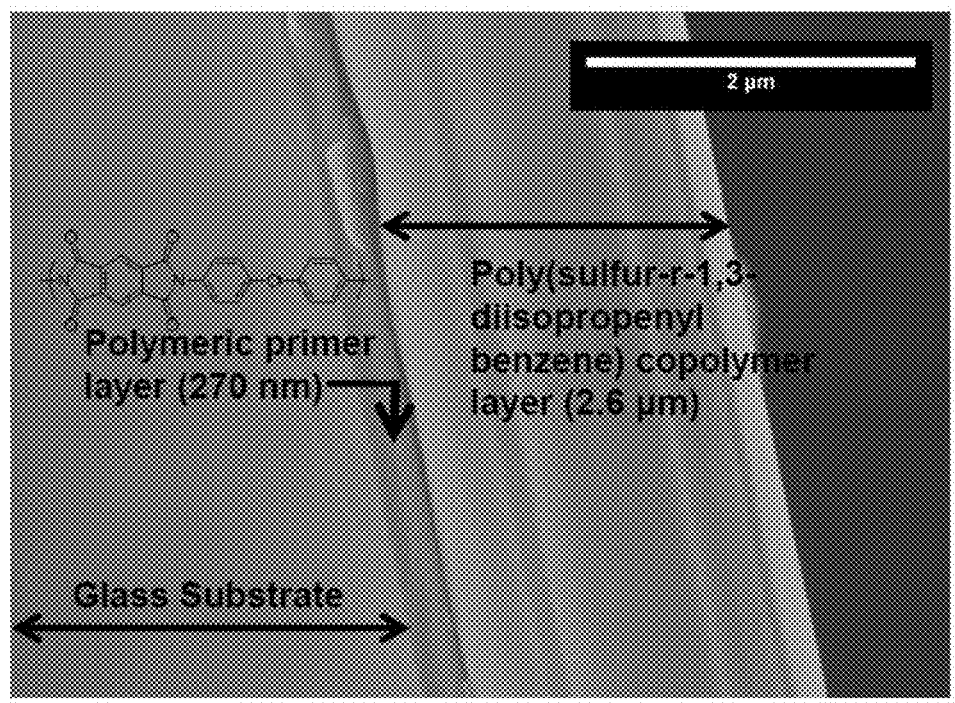
FIG. 29 is a cross-sectional micrograph of a poly(S-r-DIB) copolymer layer (2.6 μm in thickness) formed on a polyimide layer (270 nm) on a glass substrate.
Figure 30:
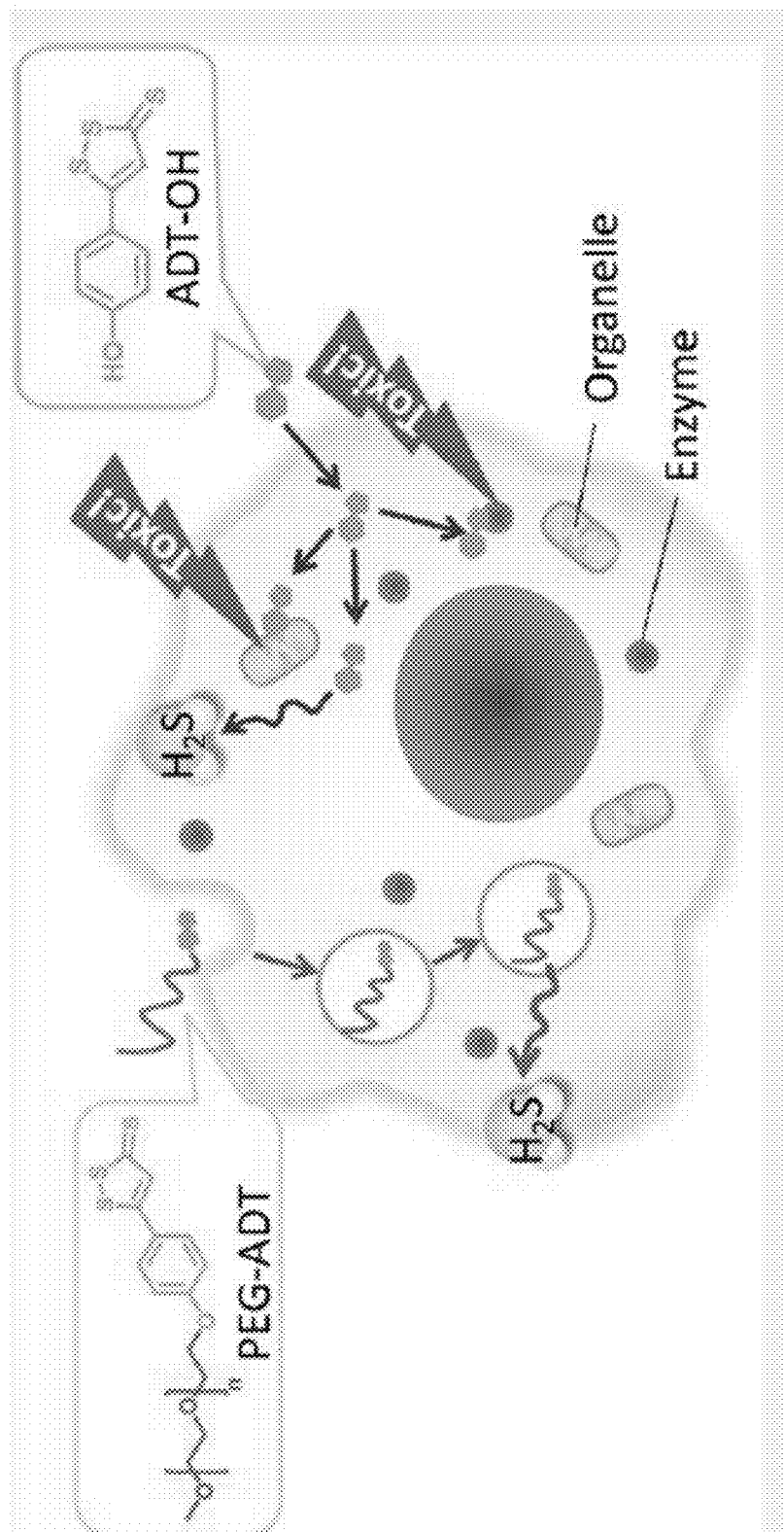
FIG. 30 shows a representation of $H_2S$ synthesis and signaling inside a biological cell (Hasegawa).
Figure 31:
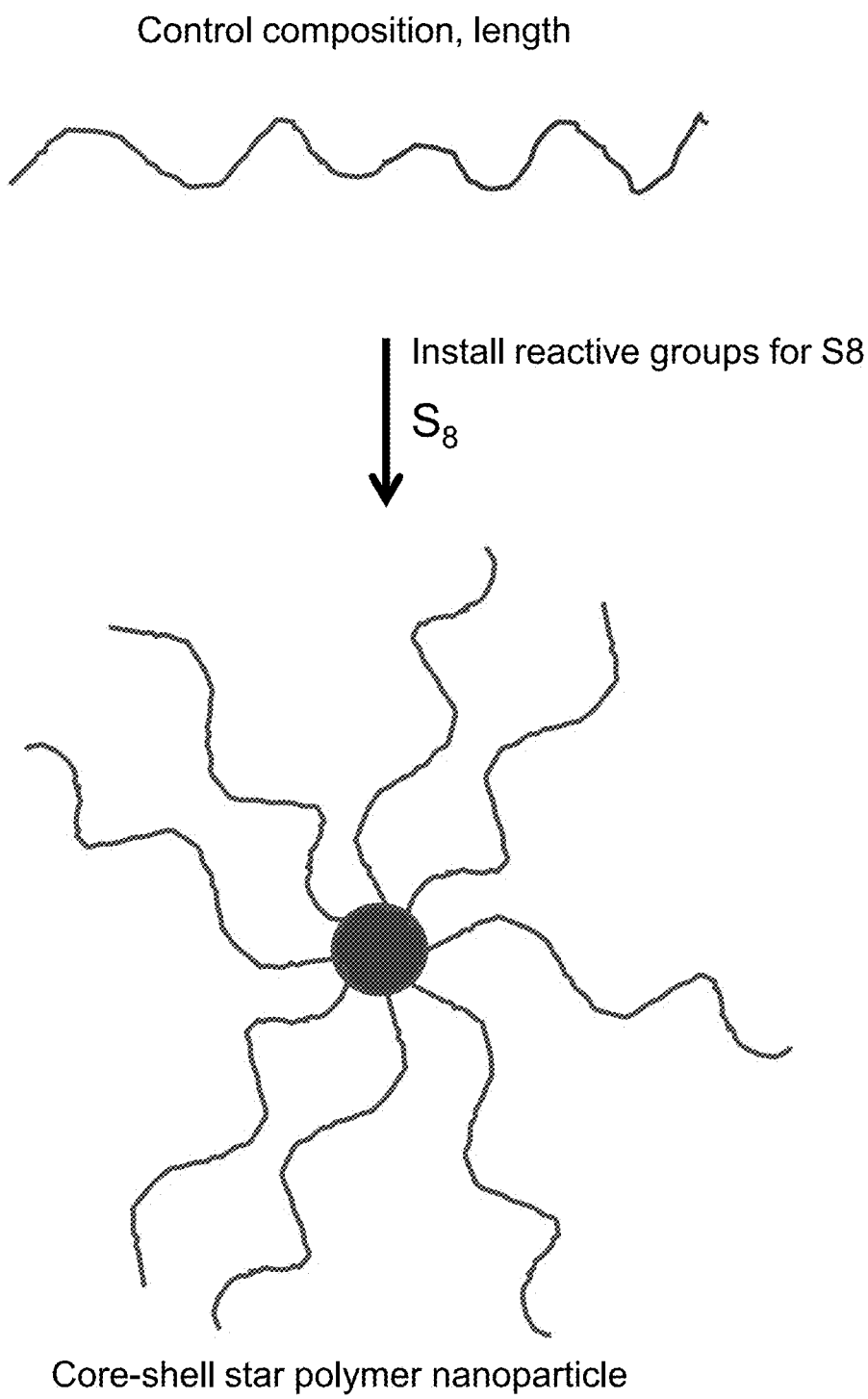
FIG. 31 shows a non-limiting example of a $H_2S$ donor polymer nanoparticle.

FIG. 28 is a picture of a set of spin-coated films. Film (a) was spun from 10× diluted poly(pyromellitic dianhydride-co-4,4'-oxodianiline) amic acid solution in N-methyl pyrrolidinone (NMP), and film (b) was spun from neat poly (pyromellitic dianhydride-co-4,4'-oxodianiline) amic acid solution. Film (c) is 17.5-wt % DIB poly(S-r-DIB) film spun onto film (a); and film (d) is 20-wt % DIB poly(S-r-DIB) film spun onto film (b). Samples a) and b) were cured at 190° C. under vacuum for 2 hours. Samples c) and d) were cured at 180° C. under vacuum for 10 minutes and then at the same temperature without vacuum for an additional 10 minutes. FIG. 29 is a cross-sectional micrograph of a poly(S-r-DIB) copolymer layer (2.6 μm in thickness) formed on a polyimide layer (270 nm) on a glass substrate.

H$_2$S Donors

In addition, the present invention features hydrogen sulfide donating sulfur containing polymers and methods of preparing said polymers. The present invention also features methods of treating biological conditions and inhibiting microbial growth using H$_2$S gas. In some embodiments, the present invention utilizes sulfur containing polymers prepared via a variety of synthetic processes, such as inverse vulcanization and other existing synthetic chemical methods to prepare molecules, polymers, nanomaterials, and nanocomposites that can deliver H2S under biological conditions.

In some embodiments, the present invention features a hydrogen sulfide (H$_2$S) donating polymer conjugate comprising a sulfur copolymer and one or more carrier polymers, wherein the carrier polymer is bonded to the sulfur copolymer. In some embodiments, the sulfur copolymer comprises one or more sulfur monomers at a level between about 5 to 95 wt % of the sulfur copolymer, and one or more comonomers each selected from a group consisting of amine monomers, thiol monomers, sulfide monomers, alkynylly unsaturated monomers, nitrone monomers, aldehyde monomers, ketone monomers, epoxide monomers, thiirane monomers, and ethylenically unsaturated monomers at a level between about 5 to 95 wt % sulfur copolymer. In some embodiments, at least one sulfur moiety of the sulfur monomer is bonded to at least one reactive functional group of the comonomers. Non-limiting examples of other monomers are described in U.S. Provisional Patent Application No. 62/039,588, filed Aug. 20, 2014, which are incorporated herein by reference.

In some embodiments, the sulfur copolymer of the polymeric conjugate comprises one or more sulfur monomers at a level in the range of about 5 to about 10 wt % of the sulfur copolymer. The sulfur copolymer may comprise one or more sulfur monomers at a level in the range of about 10 to 20 wt %, or about 20 to 30 wt %, or about 30 to 40 wt %, or about 40 to 50 wt %, or about 50 to 60 wt %, or about 60 to 70 wt %, or about 70 to 80 wt %, or about 80 to 90 wt %, or about 90 to 95 wt % of the sulfur copolymer.

In some embodiments, the sulfur copolymer of the polymeric conjugate comprises one or more monomers at a level in the range of about 5 wt % to 15 wt % of the sulfur copolymer. The sulfur copolymer may comprise one or more monomers at a level in the range of about 15 wt % to 25 wt %, or about 25 wt % to 35 wt %, or about 35 wt % to 45 wt %, or about 45 wt % to 55 wt %, or about 55 wt % to 65 wt %, or about 65 wt % to 75 wt %, or about 75 wt % to 85 wt %, or about 85 wt % to 95 wt % of the sulfur copolymer.

In some embodiments, the carrier polymer is selected from a group consisting of: N-(2-hydroxylpropyl)methacrylamide (HPMA) copolymer, a poly-L-glutamic acid, a poly(ethylene glycol) (PEG), Dextran, vinyls, alkynyls, epoxides, thiiranes, amines, sulfides, ethers, norbornenes, amides, peptides, polyesters, polyamides, polyethers, and sugars.

In some embodiments, the one or more comonomers are one or more amine monomers. In some embodiments, the amine monomer is m-phenylenediamine or p-phenylenediamine. In some embodiments, the one or more comonomers are one or more thiol monomers. In some embodiments, the thiol monomer is 4,4'-thiobis(benzenethiol). In some embodiments, the one or more comonomers are a combination of one or more amine monomers and one or more thiol monomers. In some embodiments, the one or more comonomers are one or more alkynylly unsaturated monomers. In some embodiments, the alkynylly unsaturated monomer is 1-phenylpropyne. In some embodiments, the one or more comonomers are one or more thiirane monomers. In some embodiments, the thiirane monomer is propylene sulfide. In some embodiments, the one or more comonomers are one or more epoxide monomers. In some embodiments, the one or more of the epoxide monomers are benzyl glycidyl ether, tris(4-hydroxyphenyl)methane triglycidyl ether, or a combination thereof.

In some embodiments, the sulfur monomer is at a level of at least about 20 wt % of the sulfur copolymer. In some embodiments, the sulfur monomer is at a level of at least about 50 wt % of the sulfur copolymer. In some embodiments, the sulfur monomer is at a level between about 60 and 80 wt % of the sulfur copolymer. In some embodiments, the sulfur monomer is at a level between about 70 and 95 wt % of the sulfur copolymer.

In some embodiments, the present invention features a hydrogen sulfide ($H_2S$) donating sulfur copolymer comprising one or more sulfur monomers at a level between about 5 to 95 wt % of the sulfur copolymer and one or more comonomers each selected from a group consisting of amine monomers, thiol monomers, sulfide monomers, alkynylly unsaturated monomers, nitrone monomers, aldehyde monomers, ketone monomers, epoxide monomers, thiirane monomers, and ethylenically unsaturated monomers at a level between about 5 to 95 wt % of the sulfur copolymer. In some embodiments, at least one sulfur moiety of the sulfur monomer is bonded to at least one reactive functional group of the comonomers.

In some embodiments, the sulfur monomers form a sulfur containing core of the sulfur copolymer. In some embodiments, the comonomers extend outwardly from the sulfur containing core. In some embodiments, the sulfur copolymer is linear.

In some embodiments, the present invention features a hydrogen sulfide ($H_2S$) donating sulfur copolymer comprising one or more sulfur monomers at a level of at a level between about 5 to 95 wt % of the sulfur copolymer and one or more comonomers each selected from a group consisting of amine monomers, thiol monomers, sulfide monomers, alkynylly unsaturated monomers, nitrone monomers, aldehyde monomers, ketone monomers, epoxide monomers, thiirane monomers, and ethylenically unsaturated monomers at a level between about 5 to 95 wt % of the sulfur copolymer. In some embodiments, at least one sulfur moiety of the sulfur monomer is bonded to at least one reactive functional group of the comonomers. In some embodiments, the sulfur monomers form a sulfur containing core of the sulfur copolymer. In some embodiments, the comonomers extend outwardly from the sulfur containing core.

In some embodiments, the one or more comonomers are one or more amine monomers. In some embodiments, amine monomer is m-phenylenediamine or p-phenylenediamine. In some embodiments, the one or more comonomers are one or more thiol monomers. In some embodiments, the thiol monomer is 4,4'-thiobis(benzenethiol). In some embodiments, the one or more comonomers are a combination of one or more amine monomers and one or more thiol monomers. In some embodiments, the one or more comonomers are one or more alkynylly unsaturated monomers. In some embodiments, the alkynylly unsaturated monomer is 1-phenylpropyne. In some embodiments, the one or more comonomers are one or more thiirane monomers. In some embodiments, the thiirane monomer is propylene sulfide. In some embodiments, the one or more comonomers are one or more epoxide monomers. In some embodiments, one or more of the epoxide monomers are benzyl glycidyl ether, tris(4-hydroxyphenyl)methane triglycidyl ether, or a combination thereof.

In some embodiments, the sulfur monomer is at a level of at least about 20 wt % of the sulfur copolymer. In some embodiments, the sulfur monomer is at a level of at least about 50 wt % of the sulfur copolymer. In some embodiments, the sulfur monomer is at a level between about 60 and 80 wt % of the sulfur copolymer. In some embodiments, the sulfur monomer is at a level between about 70 and 95 wt % of the sulfur copolymer.

In some embodiments, at least one functional group of the comonomers solubilizes the sulfur copolymer. In some embodiments, at least one functional group of the comonomers is biocompatible.

In some embodiments, the sulfur copolymer further comprises a one or more carrier polymers, wherein the carrier polymer is bonded to the sulfur copolymer. In some embodiments, the carrier moiety is selected from a group consisting of: an N-(2-hydroxylpropyl)methacrylamide (HPMA) copolymer, a poly-L-glutamic acid, a poly(ethylene glycol) (PEG), and Dextran, vinyls, alkynyls, epoxides, thiiranes, amines, sulfides, ethers, norbornenes, amides, peptides, polyesters, polyamides, polyethers, and sugars.

In some embodiments, the present invention features a method of treating a biological condition in a mammal in need thereof. In some embodiments, the method comprises administering a therapeutically effective amount of a hydrogen sulfide ($H_2S$) donating polymer conjugate according to any of the aforementioned polymer conjugates. In some embodiments, the polymer conjugate releases a slow and continuous amount of $H_2S$ gas, wherein the $H_2S$ triggers a biological response.

In some embodiments, the biological condition is inflammation. In some embodiments, the biological condition is heart disease. In some embodiments, the biological condition is inflammation. In some embodiments, the biological condition is hypertension. In some embodiments, the biological condition is ischemia reperfusion. In some embodiments, the polymer conjugate is administered dermally, orally, transmucosally, subcutaneously or intravenously. In some embodiments, the polymer conjugate is localized at or near an area affected by the biological condition. In some embodiments, the mammal is a human.

In another embodiment, the present invention features a method of treating a biological condition in a mammal in need thereof. In some embodiments, the method comprises administering a therapeutically effective amount of a hydrogen sulfide ($H_2S$) donating sulfur copolymer according to any of the aforementioned sulfur copolymer. In some embodiments, the sulfur copolymer releases a slow and continuous amount of $H_2S$ gas, wherein the $H_2S$ triggers a biological response. In some embodiments, modulation of the $H_2S$ release can be achieved by controlling the sulfur composition in the sulfur copolymer or polymer conjugate and the design and incorporation of the functional organic comonomers.

In some embodiments, the biological condition is inflammation. In some embodiments, the biological condition is heart disease. In some embodiments, the biological condition is inflammation. In some embodiments, the biological condition is hypertension. In some embodiments, the biological condition is ischemia reperfusion. In some embodiments, the sulfur copolymer is administered dermally, orally, transmucosally, subcutaneously or intravenously. In some embodiments, the sulfur copolymer is localized at or near an area affected by the biological condition. In some embodiments, the mammal is a human.

In some embodiments, the method further comprises administering an $H_2S$ catalyst, wherein the catalyst promotes the release of $H_2S$ gas. In some embodiments, the catalyst is cysteine or glutathione, or other thiol-containing compounds.

In some embodiments, the present invention features a method of producing an $H_2S$ donating polymer conjugate according to any of the aforementioned polymer conjugates. In some embodiments, the method comprises providing a sulfur copolymer and attaching a carrier polymer to the sulfur copolymer. In some embodiments, the step of providing a sulfur copolymer comprises providing elemental sulfur, heating the elemental sulfur into molten sulfur, and polymerizing one or more comonomers with the molten sulfur, thereby forming the sulfur copolymer. In some embodiments, a technique of polymerizing is selected from a group consisting of: free radical polymerization, controlled radical polymerization, ring-opening polymerization, ring-opening metathesis polymerization, step-growth polymerization, or chain-growth polymerization.

In some embodiments, the present invention features a method of producing an $H_2S$ donating sulfur copolymer according to any of the aforementioned sulfur copolymers. In some embodiments, the method comprises providing elemental sulfur, heating the elemental sulfur into a molten sulfur, and polymerizing one or more comonomers with the molten sulfur, thereby forming the sulfur copolymer. In some embodiments, a technique of polymerizing is selected from a group consisting of free radical polymerization, controlled radical polymerization, ring-opening polymerization, ring-opening metathesis polymerization, step-growth polymerization, or chain-growth polymerization. In some embodiments, the technique can be conducted in bulk liquid sulfur, organic solvents, water, or other solvent systems to prepare the branched copolymers containing a controllable amount of S—S bonds.

The following reaction scheme is a non-limiting example of ring-opening polymerization to form the sulfur copolymer:

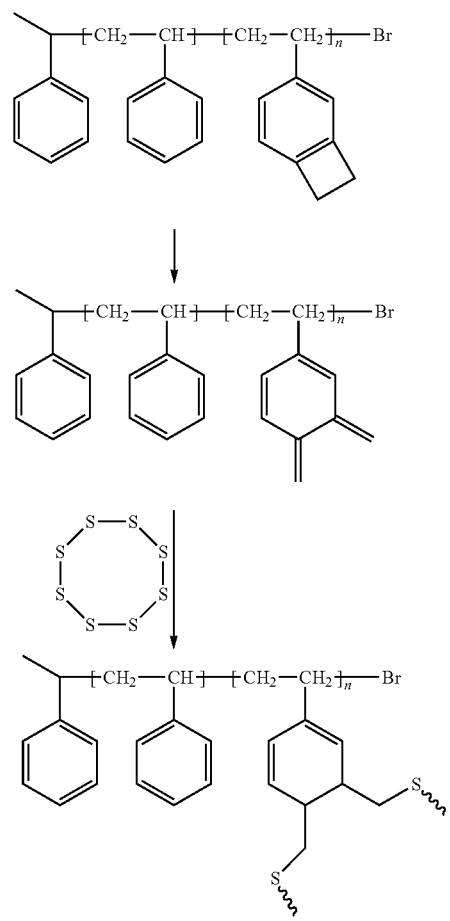

In some embodiments, the present invention features an $H_2S$ donating sulfur polymer conjugate comprising a sulfur copolymer linked to a carrier polymer, wherein the sulfur copolymer comprises at least one branched or cross-linked sulfur chain, wherein the sulfur content of the sulfur polymer conjugate ranges from about 5-95 wt %.

In other embodiments, the present invention features an $H_2S$ donating sulfur polymer conjugate comprising a sulfur copolymer linked to a carrier polymer, the sulfur copolymer having a portion comprising: —$R_1$—S—$(S)_n$—S—$R_2$—, wherein n ranges from 0 to 6, wherein the sulfur content of the sulfur polymer conjugate ranges from about 5-95 wt %.

In some embodiments, the present invention features an $H_2S$ donating sulfur copolymer comprising at least one branched or cross-linked sulfur chain, wherein the sulfur content of the sulfur copolymer ranges from about 5-95 wt %.

In some embodiments, the present invention features an $H_2S$ donating sulfur copolymer having a portion comprising: $-R_1-S-(S)_n-S-R_2-$, wherein n ranges from 0 to 6, wherein the sulfur content of the sulfur copolymer ranges from about 5-95 wt %.

In some embodiments, $R_1$ may be any of the aforementioned amine monomers, thiol monomers, sulfide monomers, alkynylly unsaturated monomers, nitrone monomers, aldehyde monomers, ketone monomers, epoxide monomers, thiirane monomers, and ethylenically unsaturated monomers bonded to the S moiety by the monomer's appropriate reactive functional group. In some embodiments, $R_2$ may be any of the aforementioned amine monomers, thiol monomers, sulfide monomers, alkynylly unsaturated monomers, nitrone monomers, aldehyde monomers, ketone monomers, epoxide monomers, thiirane monomers, and ethylenically unsaturated monomers bonded to the S moiety via the monomer's appropriate reactive functional group.

In some embodiments, the sulfur chain comprises at least one branch or cross-link arm. In some embodiments, the branch or cross-link arm may be any of the aforementioned amine monomers, thiol monomers, sulfide monomers, alkynylly unsaturated monomers, nitrone monomers, aldehyde monomers, ketone monomers, epoxide monomers, thiirane monomers, and ethylenically unsaturated monomers bonded to the S moiety of the sulfur chain via the monomer's appropriate reactive functional group.

In some embodiments, the present invention features a method of inhibiting microbial growth, said method comprising impregnating a microbial film with an $H_2S$ donating sulfur copolymer according to any of the aforementioned sulfur copolymers.

In some embodiments, the sulfur copolymer releases $H_2S$ gas thereby killing a microbe of the microbial film.

Example 21. $H_2S$ Evolution

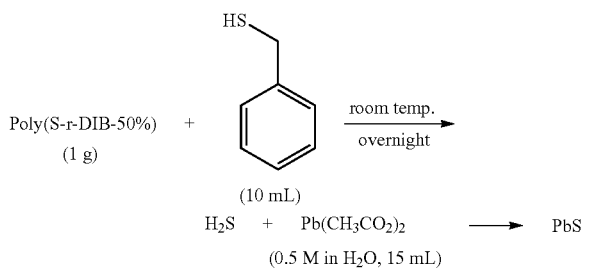

Experimental

Figure 32:
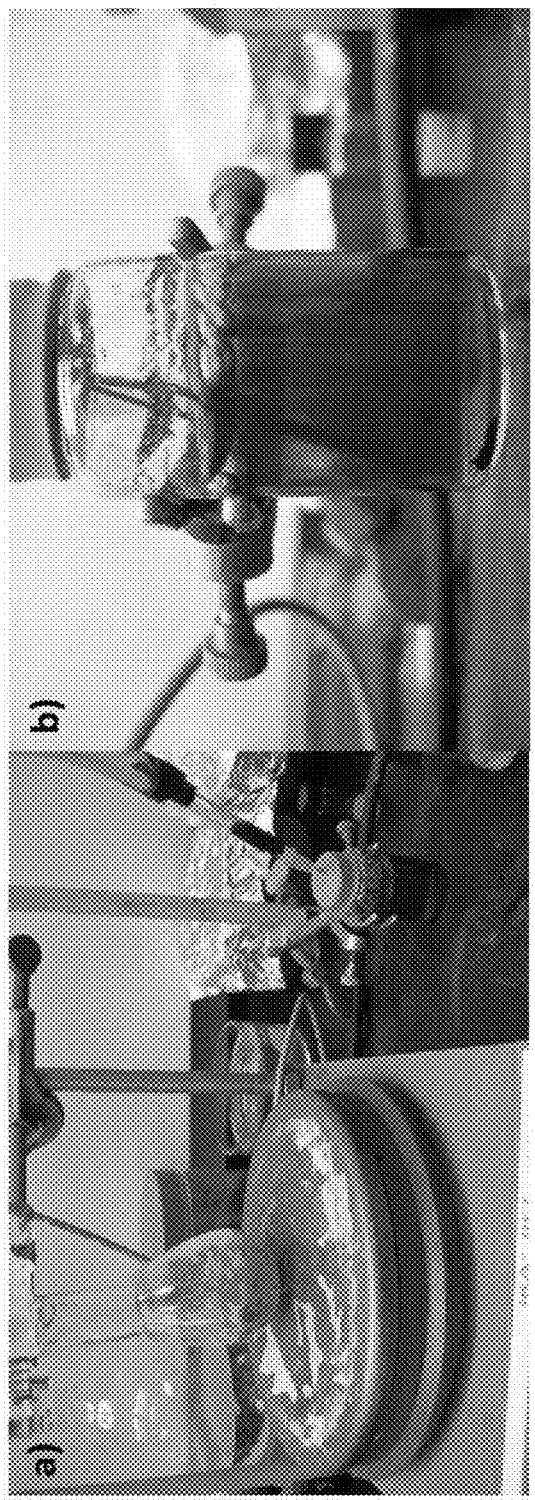
FIG. 32a-32b show a laboratory reaction set up.

As shown in FIG. 32, the following is a non-limiting example of a procedure for $H_2S$ Evolution 1. To a 25 mL Schlenk flask along with a magnetic stir bar was added a powder of poly(S-r-DIB-50%, 1.0 g).
2. Tygon tube was attached at the gas outlet of the Schlenk flask and a needle attached at the end of tygon tube was submerged into a 0.5 M aqueous solution of lead(II) acetate (15 mL) contained in 24 mL vial.
3. The Schlenk flask and vial were sealed with rubber septum and then the needle was attached on top of the rubber septum used for sealing the vial.
4. A positive argon flow was maintained and then benzyl mercaptan (10 mL, 85.2 mmol) was added.
5. The resulting mixture was stirred at room temperature for overnight under positive argon flow.
6. $H_2S$ evolution was monitored by the formation of lead(II) sulfide in 0.5 M aqueous solution of lead(II) acetate.
7. The 05.M aqueous solution was centrifuged at 10,000 rpm for 10 minutes, followed by drying under vacuum at 50° C. for overnight, and 11 mg of resulting lead(II) sulfide was isolated from the 0.5 M aqueous solution of lead(II) acetate.

Non-Limiting Preferred Embodiments

In one preferred embodiment, "Embodiment 1" as used herein, the copolymer material comprises a sulfur copolymer at a level in the range of about 5 wt % to about 95 wt % of the copolymer material. The sulfur copolymer comprises one or more sulfur monomers, at a level at least about 50 wt % of the sulfur copolymer, and one or more comonomers each selected from a group consisting of amine monomers, thiol monomers, sulfide monomers, alkynylly unsaturated monomers, epoxide monomers, nitrone monomers, aldehyde monomers, ketone monomers, thiirane monomers, and ethylenically unsaturated monomers at a level in the range of about 0.1 wt % to about 50 wt % of the sulfur copolymer.

The copolymer material of Embodiment 1 may further comprise one or more epoxide monomers at a level in the range of about 5 wt % to about 95 wt % of the copolymer material. At least one epoxy functional group of the epoxide monomers is bonded to a functional group of the sulfur copolymer. When one or more S—S bonds of the sulfur copolymer are broken, the S—S bonds are reconnected by thermal reforming.

The sulfur copolymer of Embodiment 1 may further comprise an elemental carbon material dispersed in the sulfur copolymer at a level in the range of up to about 50 wt % of the sulfur copolymer.

The sulfur copolymer of Embodiment 1 may further comprise one or more photoactive monomers at a level in the range of about 0.1 wt % to about 50 wt % of the sulfur copolymer. Each photoactive monomer may have the structure:

$$\boxed{A} - (B)_n$$

The "A" of each photoactive monomer is a ring system. "A" may be a photoactive chromophore, and is selected from a group consisting of perylenes, pyrenes, couramins, cyanine dyes, fluorescents, and derivatives thereof, polythiophenes, polyanilines, TiO2, CdSe, CdS, CdSe—CdS, natural and synthetic dyes, aromatics, heterocycles, conjugated organic polymers, inorganic chromophores, nanocomposite chromophores, organic chromophores, photoactive agents, and semiconductor nanoparticles. The "B" of each photoactive monomer comprises a polymerizable moiety selected from a group consisting of a carboxylate moiety, an ethylenically unsaturated moiety, an epoxide moiety, a thiirane moiety, an amine moiety, a thiol moiety, a sulfide moiety, an alkynylly unsaturated moiety, a nitrone moiety, an aldehyde moiety and a ketone moiety. The "n" of each photoactive monomer may be 1, 2, 3, 4, 5, 6, 7 or 8. The photoactive monomer can absorb visible radiation, infrared radiation, or solar radiation. Each B can include the polymerizable moiety and a 1-6 atom long linker, wherein each linker is selected from a group consisting of an alkylene linker and a mono, di- or tri(ethylene glycol) linker.

Photoactive species from the copolymer material of Embodiment 1 may be formed by a method comprising contacting the copolymer material with an aqueous medium, and irradiating the copolymer material in the aqueous medium with radiation that is at least partially absorbed by the one or more photoactive chromophores. The radiation is infrared, visible, or solar radiation. The irradiation causes the formation of hydrogen from the aqueous medium and a sulfur radical cation, polaron, or oxidized sulfur species from a sulfur of the copolymer material. The oxidized sulfur species is one or more of sulfate, sulfonates, sulfite, sulfoxides and sulfones.

The sulfur copolymer of Embodiment 1 may further comprise one or more polyfunctional monomers selected from a group consisting of a polyvinyl monomer, a polyisopropenyl monomer, a polyacryl monomer, a polymethacryl monomer, a polyunsaturated hydrocarbon monomer, a polyepoxide monomer, a polythiirane monomer, a polyalkynyl monomer, a polydiene monomer, a polybutadiene monomer, a polyisoprene monomer, a polynorbonene monomer, a polyamine monomer, a polythiol monomer, a polysulfide monomer, a polyalkynylly unsaturated monomers, a polynitrone monomers, a polyaldehyde monomers, a polyketone monomers, and a polyethylenically unsaturated monomers.

The copolymer material of Embodiment 1 may further comprise a nucleophilic viscosity modifier at a level up to about 10 wt % of the copolymer material.

The copolymer material of Embodiment 1 may further comprise one or more carrier polymers bonded to the sulfur copolymer to form a hydrogen sulfide donating polymer conjugate. The carrier polymer may be selected from a group consisting of an N-(2-hydroxylpropyl)methacrylamide (HPMA) copolymer, a poly-L-glutamic acid, a poly (ethylene glycol) (PEG), Dextran, vinyls, alkynyls, epoxides, thiiranes, amines, sulfides, ethers, norbomenes, amides, peptides, polyesters, polyamides, polyethers, and sugars.

At least one sulfur moiety of the sulfur monomer is bonded to at least one reactive functional group of the comonomers. The sulfur monomers form a sulfur containing core of the sulfur copolymer with the comonomers extending outwardly from the sulfur containing core. At least one functional group of the comonomers solubilizes the sulfur copolymer and at least one functional group of the comonomers is biocompatible.

The copolymer material of Embodiment 1 may be used to treat a biological condition in a mammal in need thereof. The method of treatment may comprise administering a therapeutically effective amount of the copolymer material according to Embodiment 1 or alternate embodiments of Embodiment 1. The sulfur copolymer may be administered dermally, orally, subcutaneously or intravenously. Without wishing to limit the present invention to a particular theory or mechanism, it is believed that the sulfur copolymer releases a slow and continuous amount of $H_2S$ gas that triggers a biological response. Biological conditions that are treated may be inflammation, heart disease, hypertension, and ischemia reperfusion.

An $H_2S$ catalyst may be further administered to promote the release of the slow and continuous amount of $H_2S$ gas. The catalyst may be a cysteine, a glutathione, or any other thiol-containing compounds. Alternatively, the release of the slow and continuous amount of $H_2S$ gas may be triggered by other chemical means, mechanical means, or photoirradiation.

The copolymer material of Embodiment 1 may be used for inhibiting microbial growth. The copolymer material of Embodiment 1 can be impregnated into a microbial film and the sulfur copolymer releases $H_2S$ gas that kills the microbes in the microbial film.

The copolymer material of Embodiment 1 may be produced by providing elemental sulfur, heating the elemental sulfur into a molten sulfur, and polymerizing one or more comonomers of Embodiment 1 with the molten sulfur, thereby forming the sulfur copolymer. The technique of polymerizing may be free radical polymerization, controlled radical polymerization, ring-opening polymerization, ring-opening metathesis polymerization, step-growth polymerization, or chain-growth polymerization.

The copolymer material of Embodiment 1 may further comprise a second comonomer to form a terpolymer material. The second comonomer is selected from a group consisting of one or more monomers of epoxides, isocyanates, acid chlorides, carboxylic acids, esters, and alkyl halides. The terpolymer material may be produced by providing elemental sulfur, heating the elemental sulfur into a molten sulfur, polymerizing one or more comonomers of Embodiment 1 with the molten sulfur to form a sulfur copolymer, and reacting an available reactive functional group on the sulfur copolymer with one or more monomers of the second comonomer to form the terpolymer material. The technique of reacting is selected from a group consisting of: oxidative coupling, polymerization, or copolymerization.

An article may be formed from the copolymer material of Embodiment 1 by heating the copolymer material at a temperature in the range of about 160° C. to about 230° C., forming the copolymer material into a shape of the article, and heating the formed copolymer material to yield the article. Alternatively, the article may be formed from the copolymer material of Embodiment 1 by admixing the copolymer material in a solvent, forming the admixed copolymer material into a shape of the article, and removing the solvent from the copolymer material to yield the article.

In an oil-in-water emulsion, the copolymer material of Embodiment 1 may be as a colloidal phase suspended in the aqueous solution. A surfactant may or may not be present in the aqueous solution.

The copolymer material of Embodiment 1 may be formed as an optical element of a substantially optically transparent body. The copolymer material has a refractive index in the range of about 1.7 to about 2.2 and at least one wavelength in the range of about 300 nm to about 10 µm.

The copolymer material of Embodiment 1 may be used in an electrochemical cell. The electrochemical cell may comprise an anode comprising metallic lithium, a cathode comprising the copolymer material of Embodiment 1, and a non-aqueous electrolyte interposed between the cathode and the anode. The copolymer generates soluble additive species in situ upon discharge, and the soluble additive species are co-deposited with lower sulfide discharge products onto the cathode by an electrochemical reaction or a non-electrochemical reaction.

The chemistry via the copolymerization of the one or more monomers of amine monomers, thiol monomers, sulfide monomers, alkynylly unsaturated monomers, nitrone monomers, aldehyde monomers, and ketone monomers in liquid as used herein produce these advantageous sulfur copolymer compositions.

For example, the amine monomer, such as those on aromatic compounds, results in direct C—S bond formation and copolymerization with sulfur concurrently.

For example, the thiol monomers from a wide range of comonomer precursors widely used in the preparation of condensation polymers can be dissolved and copolymerization with liquid sulfur to afford high sulfur content copolymers. Unexpectedly, the thiol derived copolymer was solution processable despite the high content of sulfur and rigid aromatic moieties.

For example, the sulfide monomer can copolymerize with sulfur via either ionic, or free radical processes. Unexpectedly, the sulfide monomer was able to afford both low glass transition polymers, or higher glass transition polymers.

For example, the alkynylly unsaturated monomer is expected to react via known thiol-yne processes, however, unexpectedly, the alkynylly unsaturated monomer was able to afford polythiophene and other heterocyles.

For example, the nitrone monomer is expected to react via free radical polymerizations with sulfur radicals. Unexpectedly, the nitrone monomer was designed to afford polymeric materials when copolymerized with elemental sulfur.

Aldehyde based monomers are not expected to react with sulfur radicals, however, the formation of polymers was observed when the appropriate di-, or multifunctional aldehydes are copolymerized with sulfur.

Ketone based monomers are not expected to react with sulfur radicals, however, the formation of polymers was observed when the appropriate di-, or multifunctional ketones are copolymerized with sulfur.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

REFERENCES

1. Chung, W. J. et al., Angew. Chem. Int. Ed., 2011, 50, 11409-11412.
2. Colquhoun, Howard M., "Materials that heal themselves", *Nature Chemistry*, June 2012, Vol. 4, 435-436.
3. Yang, Ying and Urban Marek W., "Self-healing polymeric materials", *Chem. Soc. Rev.*, 2013, 42, 7446-7467.
4. Hasegawa, Urara and van der Vlies, André J., "Design and Synthesis of Polymeric Hydrogen Sulfide Donors", *Bioconjugate Chemistry*, 2014, 25 (7), 1290-1300.
5. Foster, Jeffrey C., et al., "S-Aroylthiooximes: A Facile Route to Hydrogen Sulfide Releasing Compounds with Structure-Dependent Release Kinetics", *Organic Letters*. 2014, 16, 1558-1561.
6. Wurther, F. Chem. Commun. 2004, 1564-1579.

What is claimed:
1. A composite material comprising:
   a) a sulfur at a level at least about 50 wt % of the composite material; and
   b) a metal or ceramic composite having a formula $M_xR_y$, and at a level from about 0.1 to about 50 wt % of the composite material;
      wherein M is selected from a group consisting of Ag, Al, As Au, B, Ba, Bi, Ca, Cd, Ce, Co, Cr, Cu, Eu, Fe, Ga, Gd, Ge, Hf, Hg, In, La, Li, Mg, Mn, Mo, Na, Nb, Nd, Ni, P, Pb, Pd, Pr, Sb, Se, Si, Sn, Sr, Ta, Ti, Tl, V, W, Y, Yb, Zn and Zr;
      wherein R is selected from a group consisting of C, N, and S;
      wherein x ranges from about 1 to about 30, and wherein y ranges from about 1 to about 10; and
      wherein the composite material is a vitrified material.

2. The composite material of claim 1, wherein the metal or ceramic composite is dispersed in the sulfur.

3. The composite material of claim 1, wherein when R is C, M is selected from a group consisting of Al, B, Ca, Cr, Hf, Mo, Nb, Si, Ta, Ti, V, W, Y, and Zr.

4. The composite material of claim 1, wherein when R is N, M is selected from a group consisting of Al, B, Ba, Bi, Ca, Cr, Cu, Eu, Fe, Ga, Gd, La, Li, Mg, Mn, Nb, Nd, Pr, Si, Sr, Ta, Ti, V, Zn or Zr.

5. The composite material of claim 1, wherein when R is S, M is selected from a group consisting of Ag, Al, As, Au, Ba, Bi, Cd, Ce, Co, Cu, Fe, Ga, Ge, Hg, In, Li, Mn, Mo, Na, Ni, P, Pb, Pd, Sb, Se, Sn, Sr, Ti, Tl, W, Yb, and Zn.

6. The composite material of claim 1, wherein the composite material is copolymerized with a sulfur copolymer, wherein the sulfur copolymer comprises one or more sulfur monomers, at a level in the range of at least about 50 wt % of the sulfur copolymer, and one or more comonomers each selected from a group consisting of amine monomers, thiol monomers, sulfide monomers, alkynylly unsaturated monomers, nitrone monomers, aldehyde monomers, ketone monomers, epoxide monomers, thiirane monomers, and ethylenically unsaturated monomers at a level in the range of about 0.1 wt % to about 50 wt % of the sulfur copolymer.

7. A composite material comprising:
   a) a sulfur at a level at least about 50 wt % of the composite material; and
   b) a metal sulfur composite having a formula $P_xS_yM_z$ and at a level from about 0.1 to about 50 wt % of the composite material;
      wherein P is selected from a group consisting of Li and Na;
      wherein M is selected from a group consisting of Ag, Al, As Au, B, Ba, Bi, Ca, Cd, Ce, Co, Cr, Cu, Eu, Fe, Ga, Gd, Ge, Hf, Hg, In, La, Li, Mg, Mn, Mo, Na, Nb, Nd, Ni, P, Pb, Pd, Pr, Sb, Se, Si, Sn, Sr, Ta, Ti, Tl, V, W, Y, Yb, Zn and Zr;
      wherein P and M are different;
      wherein x ranges from about 1 to about 10, y ranges from about 1 and to about 10, and wherein z ranges from about 1 to about 30;
      wherein the metal sulfur composite is a uniform single phase; and
      wherein the composite material is a solid composite material,
      wherein the composite material is a vitrified material.

8. The composite material of claim 7, wherein the metal sulfur composite is dispersed in the sulfur.

9. The composite material of claim 7, wherein the composite material is copolymerized with a sulfur copolymer, wherein the sulfur copolymer comprises one or more sulfur monomers, at a level in the range of at least about 50 wt % of the sulfur copolymer, and one or more comonomers each selected from a group consisting of amine monomers, thiol monomers, sulfide monomers, alkynylly unsaturated monomers, nitrone monomers, aldehyde monomers, ketone monomers, epoxide monomers, thiirane monomers, and ethylenically unsaturated monomers, at a level in the range of about 0.1 wt % to about 50 wt % of the sulfur copolymer.

10. An electrochemical cell comprising:
    a. an anode comprising metallic lithium;
    b. a cathode comprising the composite material comprising:
        a sulfur at a level at least about 50 wt % of the composite material; and
        a metal or ceramic composite having a formula $M_xR_y$ and at a level from about 0.1 to about 50 wt % of the composite material;
        wherein M is selected from a group consisting of Ag, Al, As Au, B, Ba, Bi, Ca, Cd, Ce, Co, Cr, Cu, Eu, Fe, Ga, Gd, Ge, Hf, Hg, In, La, Li, Mg, Mn, Mo, Na, Nb, Nd, Ni, P, Pb, Pd, Pr, Sb, Se, Si, Sn, Sr, Ta, Ti, Tl, V, W, Y, Yb, Zn and Zr;
        wherein R is selected from a group consisting of C, N, and S;
        wherein x ranges from about 1 to about 30, and wherein y ranges from about 1 to about 10; and
        wherein the composite material is a vitrified material; and
    c. a non-aqueous electrolyte interposed between the cathode and the anode; wherein the composite material generates soluble additive species in situ upon discharge, wherein the soluble additive species are co-deposited with lower sulfide discharge products onto the cathode by an electrochemical reaction or a non-electrochemical reaction.

11. The electrochemical cell of claim 10, wherein the electrochemical cell has a capacity of between about 200 and about 1,400 mAh/g.

* * * * *